US008835423B2

(12) United States Patent
Arvanitis et al.

(10) Patent No.: US 8,835,423 B2
(45) Date of Patent: *Sep. 16, 2014

(54) AZEPINE INHIBITORS OF JANUS KINASES

(71) Applicant: Incyte Corporation, Wilmington, DE (US)

(72) Inventors: Argyrios G. Arvanitis, Kennett Square, PA (US); James D. Rodgers, Landenberg, PA (US); Andrew P. Combs, Kennett Square, PA (US); Richard B. Sparks, Wilmington, DE (US); Darius J. Robinson, Lafayette, NY (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/032,629

(22) Filed: Sep. 20, 2013

(65) Prior Publication Data

US 2014/0031344 A1    Jan. 30, 2014

Related U.S. Application Data

(63) Continuation of application No. 13/479,045, filed on May 23, 2012, now Pat. No. 8,563,541, which is a continuation of application No. 12/418,132, filed on Apr. 3, 2009, now abandoned, which is a continuation of application No. 11/524,641, filed on Sep. 21, 2006, now abandoned.

(60) Provisional application No. 60/810,490, filed on Jun. 2, 2006, provisional application No. 60/719,462, filed on Sep. 22, 2005.

(51) Int. Cl.
*A61K 31/55* (2006.01)
*C12N 9/99* (2006.01)

(52) U.S. Cl.
USPC .......................................... 514/215; 435/184

(58) Field of Classification Search
USPC ........................................ 514/215; 435/184
See application file for complete search history.

(56) References Cited

U.S. PATENT DOCUMENTS

| | | | |
|---|---|---|---|
| 5,521,184 A | 5/1996 | Zimmermann | |
| 5,919,779 A | 7/1999 | Proudfoot et al. | |
| 6,486,322 B1 | 11/2002 | Longo et al. | |
| 6,579,882 B2 | 6/2003 | Stewart et al. | |
| 6,852,727 B2 | 2/2005 | Goulet et al. | |
| 7,005,436 B2 | 2/2006 | Lloyd et al. | |
| 8,563,541 B2 * | 10/2013 | Arvanitis et al. ............ | 514/215 |
| 2003/0100756 A1 | 5/2003 | Adams et al. | |
| 2003/0165576 A1 | 9/2003 | Fujii et al. | |
| 2004/0009983 A1 | 1/2004 | Cox et al. | |
| 2004/0198737 A1 | 10/2004 | Cox et al. | |
| 2005/0153989 A1 | 7/2005 | Grotzfeld et al. | |
| 2006/0079511 A1 | 4/2006 | Liu et al. | |
| 2006/0106020 A1 | 5/2006 | Rodgers et al. | |
| 2006/0183761 A1 | 8/2006 | Ledeboer et al. | |
| 2006/0183906 A1 | 8/2006 | Rodgers et al. | |
| 2007/0135461 A1 | 6/2007 | Rodgers et al. | |
| 2007/0149506 A1 | 6/2007 | Arvanitis et al. | |
| 2009/0197869 A1 | 8/2009 | Arvanitis et al. | |

FOREIGN PATENT DOCUMENTS

| | | |
|---|---|---|
| DE | 30 36 390 | 5/1982 |
| WO | WO 97/02262 | 1/1997 |
| WO | WO 99/07379 | 2/1999 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/53595 | 9/2000 |
| WO | WO 01/07436 | 2/2001 |
| WO | WO 01/14402 | 3/2001 |
| WO | WO 01/42246 | 6/2001 |
| WO | WO 01/64655 | 9/2001 |
| WO | WO 02/00196 | 1/2002 |
| WO | WO 02/00661 | 1/2002 |
| WO | WO 02/055084 | 7/2002 |
| WO | WO 02/060492 | 8/2002 |
| WO | WO 02/096909 | 12/2002 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/099771 | 12/2003 |
| WO | WO 2004/005281 | 1/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |

(Continued)

OTHER PUBLICATIONS

International Preliminary Examination Report in PCT/US2006/036872, dated Apr. 3, 2008, an International Application corresponding to the present application (7 pages).

International Search Report and Written Opinion of the International Search Authority in PCT/US2006/036872, dated Mar. 6, 2007, an International Application corresponding to the present application (3 pages).

Office Action dated Mar. 9, 2009, received in corresponding Chilean Application No. 2510-2006.

Examination Report dated Jun. 13, 2008, received in corresponding European Application No. 06825052.1.

(Continued)

*Primary Examiner* — Charanjit Aulakh
(74) *Attorney, Agent, or Firm* — Fish & Richardson P.C.

(57) ABSTRACT

The present invention provides compounds that modulate the activity of Janus kinases and are useful in the treatment of diseases related to activity of Janus kinases including, for example, immune-related diseases, skin disorders, myeloid proliferative disorders, cancer, and other diseases.

33 Claims, No Drawings

(56) References Cited

FOREIGN PATENT DOCUMENTS

| | | |
|---|---|---|
| WO | WO 2004/099204 | 11/2004 |
| WO | WO 2004/099205 | 11/2004 |
| WO | WO 2005/013986 | 2/2005 |
| WO | WO 2005/028444 | 3/2005 |
| WO | WO 2005/037825 | 4/2005 |
| WO | WO 2005/051393 | 6/2005 |
| WO | WO 2005/060972 | 7/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/121130 | 12/2005 |
| WO | WO 2006/013114 | 2/2006 |
| WO | WO 2006/046023 | 5/2006 |
| WO | WO 2006/046024 | 5/2006 |
| WO | WO 2006/056399 | 6/2006 |
| WO | WO 2006/065703 | 6/2006 |
| WO | WO 2006/096270 | 9/2006 |
| WO | WO 2006/116733 | 11/2006 |
| WO | WO 2006/127587 | 11/2006 |
| WO | WO 2007/025090 | 3/2007 |
| WO | WO 2007/041130 | 4/2007 |
| WO | WO 2007/044779 | 4/2007 |
| WO | WO 2007/076423 | 7/2007 |
| WO | WO 2007/084557 | 7/2007 |
| WO | WO 2007/117494 | 10/2007 |

OTHER PUBLICATIONS

"INCB18424 Discussion" Presentation at the American Society of Hematology, 49th Annual Meeting and Exposition, Atlanta, GA. Abstract #558, Dec. 10, 2008.

26th Annual JPMorgan Healthcare Conference presentation dated Jan. 8, 2008.

Adv Pharmacol. 2000;47:113-74.

Agents Actions. Jan. 1993;38(1-2):116-21.

Bell, Malcolm, and Zalay, Andrew, "Synthesis of Substituted 3-Amino[6, 5-b] triazinoindoles." Journal of Heterocyclic Chemistry, 12(5):1001-1004, Oct. 1975.

Bioreversible Carriers in Drug Design, ed. Edward B. Roche, American Pharmaceutical Association and Pergamon Press, 1987*.

Blume-Jensen P et al, Nature 2001, 411(6835):355-365.

Bolen JB. Nonreceptor tyrosine protein kinases. Oncogene. 1993, 8(8):2025-31.

Borie, D.C. et al., Transplantation. Dec. 27, 2005;80(12):1756-64.

Boudny, V., and Kovarik, J., Neoplasm. 49:349-355, 2002.

Bowman, T., et al. Oncogene 19:2474-2488, 2000.

Burger, R., et al. Hematol J. 2:42-53, 2001.

Cetkovic-Cvrlje et al., "Targeting JAK3 with JANEX-1 for prevention of autoimmune type 1 diabetes in NOD mice", Clin. Immunol 106(3):213-25 (2003).

Chalandon et al. "Targeting mutated protein tyrosine kinases and their signaling pathways in hematologic malignancies." Hematologica, 2005, 90:949-968.

Changelian, P.S. et al. Science, 2003, 302, 875-878.

Chen, C.L. et al., "Stat3 Activation in Human Endometrial and Cervical Cancer", British Journal of Cancer, 96 591-599, 2007.

Conklyn, M. et al., Journal of Leukocyte Biology, 2004, 76, 1248-1255.

Current Protocols in Immnology, vol. 3., Coligan, J.E. et al, Wiley Press. (1998) *.

Daniels et al., "Imatinib mesylate inhibits the profibrogenic activity of TGF-β and prevents bleomycinmediated lung fibrosis." J. Clin. Invest., 114(9):1308-1316, Nov. 2004.

De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells", Br. J. Haematol. 109(4):823-8 (2000).

Deuse, T. et al., Transplantation, 2008, 85(6) 885-892.

Doleschall G., and Lempert, K. "Thermal and Acid Catalysed Degradations of 3-Alkylthio-6,7-Dihydro-[1.2.4]Triazino[1.6-c]Quinazolin-5-Ium- I-Olates." Tetrahedron, 30:3997-4012, 1974.

Dudley, A.C. et al. Biochem. J. 2005, 390(Pt 2):427-36.

E. Quesada et al, Tetrahedron, 62 (2006) 6673-6680.

Estel, L.; Marsais, F.; and Queguiner, G [Journal of Organic Chemistry (1988), 53(12), 2740-44.

Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007.

Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285.

Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007.

Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov 8-10, 2007. Poster 0009.

Gorre, M.E. et al., "Clinical Resistance to STI-571 Cancer Therapy Caused by BCR-ABL Gene Mutation or Amplification." Science, 293:876, 2001.

Gotlieb, Alice, Presentation at the 2008 American Academy of Dermatology, 66th Annual Meeting, San Antonio, TX. Feb. 1, 2008, symposium-303.

Gottlieb, A.B., et al, "Psoriasis: emergining therapeutic stragegies,", Nature Reviews, Jan. 2005, vol. 4, No. 1, 19-34.

Hubschwerlen, c. et al., "Piramido[1,6-a]benzimidazoles: A New Class of DNA Gurase Inhibitors", J. med. Chem., 35, 1385-1392, 1992. XP-002309406.

Immnol Today. Jan. 1998;19(1):37-44.

Ishizaki, T. et al. Molecular Pharmacology, 2000, 57, 976-983.

Itagaki, Noriaki; et al.,. Organic Letters 2005; 7(19); 4181-4183.

James, c., et al. "A unique clonal JAK2 mutation leading to constitutive signaling causes polycythaemia vera", Nature vol. 434, Apr. 2005, 1144-1148.

Journal of Organic Chemistry (1979), 44(9):1574.

Journal of Pharmaceutical Science, 66, 2 (1977).

Kharas, Michael, and Fruman, David, "ABL Oncogenes and Phosphoinositide 3-Kinase: Mechanism of Activation and Downstream Effectors." Cancer Res., 65(6):2047-2053, Mar. 15, 2005.

Kruh et al., "The complete coding sequence of arg defines the Abelson subfamily of cytoplasmic tyrosine kinases." Proc. Natl. Acad. Sci., 87:5802-5806, Aug. 1990.

Kubinyi, H. "QSAR: Hansch Analysis and Related Approaches," Methods and Principles in Medicinal Chemistry, Manhold, R. ed. Weinhein, NY, 1993.

Kudelacz, E. et al. European Journal of Pharmacology 582 (2008) 154-161.

Laufer et al., "Novel substituted pyridinyl imidazoles as potent anticytokine agents with low activity against hepatic cytochrome P450 enzymes", J. Med. Chem. 46:3230-44 (2003).

Letter dated May 12, 2008 from Clark Modet & Co. To the applicant's representatives describing the contents of an Official Action in Chilean Patent Application 2510-2006, a Chilean Patent Application corresponding to the present application.

Levine et al., "Activating mutation in the tyrosine kinase JAK2 in polycythemia vera, essential thrombocythemia, and myeloid metaplasia with myelofibrosis", Cancer Cell 7:387-97 (2005).

Madhusudan S, Ganesan TS. Tyrosine kinase inhibitors in cancer therapy. Clin Biochem. 2004, 37(7):618-35.

Manning, G. et al., Science. 2002, 298(5600):1912-1934.

Methods in Molecular Biology: vol. 225, Inflammation Protocols., Winyard, P.G. and Willoughby, D.A., Humana Press, 2003*.

(56) References Cited

OTHER PUBLICATIONS

Milici, A.J., et al., *Arthritis Research & Therapy* 2008, 10:R14 (http://arthritis-research.com/content/10/1/R14).
Nakagawara, Akira, "Trk receptor tyrosine kinases: A bridge between cancer and neural development." *Cancer Letters*, 169:107-114, 2001.
Neubauer, H., A. Cumano, et al. (1998). Cell 93(3): 397-409.
Nickoloff et al, "Recent insights into the immunopathogenesis of psoriasis provide new therapeutic opportunities", J Clin. Invest., vol. 113, No. 12, Jun. 2004, 1664-1675.
Nishio, M. et al. FEBS *Letters*, 1999, 445, 87-91.
Org. Lett. 2002, 4, 3013.
Organic Preparations & Procedures International, 1999, 31(6):693-4.
Palmer, Amparo, and Klein, Rudiger, "Multiple roles of ephrins in morphogenesis, neuronal networking, and brain function." *Genes & Dev.*, 17:1429-1450, 2003.
Park et al., Analytical Biochemistry 1999, 269, 94-104.
Patani, G.A. et al. *Chem. Rev.* 1996, 96, 3147-3176.
Pernis, A. B. and P. B. Rothman, "JAK-STAT signaling is Asthma", J Clin. Invest. vol. 109, No. 10, May 2002, 1279-1283.
Peters et al., "Functional Significance of Tie2 Signaling in the Adult Vasculature." *The Endocrine Society*, pp. 51-71, 2004.
Remington's Pharmaceutical Sciences, 17th ed., Mack Publishing Company, Easton, Pa., 1985, p. 1418.
Rodig, S. I, M. A. Meraz, et al., Disruption of the JAK1 Gene Demonstrates Obligatory and Nomedundent Roles of the Jaks in Cytokine-Induced Biologic Responses, Cell, vol. 93,373-383 (1998).
Rousvoal, G. et al. *Transpl Int.* Dec. 2006; 19(12):1014-21.
Saemann et al., "Prevention of CD40-triggered dendritic cell maturation and induction of T-cell hyporeactivity by targeting of Janus kinase 3", Am. J. Transplant 3(11):1341-9 (2003).
Scott, M. J, C. J Godshall, et al., "Jaks, STATs, Cytokines and Sepsis", Clinical and Diagnostic Laboratory Immunology, Nov. 2002, 99, 1153-1159, (2002).
Seto, Y., H. Nakajima, et al., "Enhanced Th2 Cell-Mediated Allergic Inflammation in Tyk2-Deficient Mice", The Journal of Immunology, vol. 170, 1077-1083, (2003).
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Sriram, K. et al. *J. Biol. Chem.* 2004, 279(19):19936-47. Epub Mar. 2, 2004.
Staerk, I, et al. "JAK1 and Tky2 Activation by the Homologous Polycythemia Vera JAK2 V617F Mutation", J Biol. Chem., 280:41893-41899 (2005).
T. Higuchi and V. Stella, "Pro-drugs as Novel Delivery Systems," vol. 14 of the A.C.S. Symposium Series (1975) *.
T.W. Green and P.G.M. Wuts, Protective Groups in Organic Synthesis, 3rd. Ed., Wiley & Sons, Inc., New York (1999)*.
Takemoto, S., et al. "Proliferation of adult T cell leukemia/lymphoma cells is associated with the constitutive activation of JAK1STAT proteins", Proc. Nat. Acad. Sci. USA, vol. 94, pp. 1389713902 (1997).
Thompson, J. et al., "Photochemical preparation of a pyridine containing tetracycle: a Jak protein kinase inhibitor", Bioorg. & Med. Chem. Lett. 12:1219-23 (2002).
Walters, D.K. et al. Cancer Cell, 2006, 10, 65.
Wu T.Y.H., et al. Organic Letters, 2003, 5(20), 3587-3590.
Zou, Xiaoming, and Calame, Kathryn, "Signaling Pathways Activated by Oncogenic Forms of Abl Tyrosine Kinase." Journal of Biological Chemistry, 274(26):18141-18144, 1999.
ADIS R&D Profile, "Tofacitinib", Drugs R D, vol. 10, No. 4, pp. 271-284, (2010).
Borie et al., "Combined use of the JAK3 inhibitor CP-690,550 with mycophenolate mofetil to prevent kidney allograft rejection in non-human primates," Transplantation, vol. 80, No. 12, Abstract 1 page, Dec. 27, 2005.
Boy et al., "Double-Blind, Placebo-Controlled, Dose-Escalation Study to Evaluate the Pharmacologic Effect of CP-690,550 in Patients With Psoriasis," Journal of Investigative Dermatoloty, vol. 129, pp. 299-2302, (2009).
Candotti et al., "Molecular aspects of primary immunodeficiencies: lessons from cytokine and other signaling pathways," The Journal of Clinical Investigation, vol. 109, No. 10, pp. 1261-1269, May 2002.
Candotti et al., "Structural and Functional Basis for JAK3-Deficient Severe Combined Immunodeficiency," Blood, vol. 90, No. 10, pp. 3996-4003, Nov. 15, 1997.
Changelian et al., "Prevention of Organ Allograft Rejection by a Specific Janus Kinase 3 Inhibitor," Science, vol. 302, pp. 875-878, Oct. 31, 2003.
FDA New Release, "FDA approves Xeljanz for rheumatoid arthritis," U.S. Food and Drug Administration, 2 pages, Nov. 6, 2012.
Kawamura et al., "Molecular cloning of L-JAK, a Janus family protein-tyrosine kinase expressed in natural killer cells and activated leukocytes," Proceedings of the National Academy of Sciences USA, vol. 91, pp. 6374-6378, Jul. 1994.).
Levine et al., "Activating mutation in the tyrosine kinase JAK2 in polycythemia vera, essential thrombocythemia, and myeloid metaplasia with myelofibrosis," Cancer Cell, vol. 7, pp. 387-397, Apr. 2005.
Nickoloff et al., "Recent insights into the immunopathogenesis of psoriasis prove new therapeutic opportunities," The Journal of Clinical Investigation, vol. 113, No. 12, pp. 1664-1675, Jun. 2004.).
O'Shea et al., "A New Modality for Immunosuppression: Targeting the JAK/STAT Pathway," Nature Reviews: Drug Discovery, vol. 3, pp. 555-564, Jul. 2004.
Ortmann et al., "Janus kinases and signal transducers and activators of transcription: their roles in cytokine signaling, development and immunoregulation," Arthritis Research & Therapy, vol. 2, pp. 16-32, (2000).
Parganas et al., "Jak2 is Essential for Signaling through a Variety of Cytokine Receptors," Cell, vol. 95, pp. 385-395, May 1, 1998.
West, "CP-690550, a JAK3 inhibitor as an immunosuppressant for the treatment of rheumatoid arthritis, transplant rejection, psoriasis and other immune-mediated disorders," Current Opinions in Investigational Drugs, vol. 10, No. 5, pp. 491-504, (2009).

* cited by examiner

AZEPINE INHIBITORS OF JANUS KINASES

CROSS REFERENCE TO RELATED APPLICATIONS

This application is a continuation of U.S. Ser. No. 13/479,045, filed May 23, 2012, which is a continuation of U.S. Ser. No. 12/418,132, filed Apr. 3, 2009, which is a continuation of U.S. Ser. No. 11/524,641, filed Sep. 21, 2006, which claims the benefit of U.S. Ser. No. 60/719,462, filed Sep. 22, 2005, and U.S. Ser. No. 60/810,490, filed Jun. 2, 2006, the disclosures of each of which are incorporated herein by reference in their entireties.

FIELD OF THE INVENTION

The present invention relates to compounds that modulate the activity of Janus kinases and are useful in the treatment of diseases related to activity of Janus kinases including, for example, immune-related diseases, skin disorders, myeloid proliferative disorders, cancer, and other diseases.

BACKGROUND OF THE INVENTION

The immune system responds to injury and threats from pathogens. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens.

Binding of a cytokine to its cell surface receptor initiates intracellular signaling cascades that transduce the extracellular signal to the nucleus, ultimately leading to changes in gene expression. The pathway involving the Janus kinase family of protein tyrosine kinases (JAKs) and Signal Transducers and Activators of Transcription (STATs) is engaged in the signaling of a wide range of cytokines. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." Clin Diagn Lab Immunol 9(6): 1153-9).

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

While JAK1, JAK2 and TYK2 are ubiquitously expressed, JAK3 is reported to be preferentially expressed in natural killer (NK) cells and not resting T cells, suggesting a role in lymphoid activation (Kawamura, M., D. W. McVicar, et al. (1994). "Molecular cloning of L-JAK, a Janus family protein-tyrosine kinase expressed in natural killer cells and activated leukocytes." Proc Natl Acad Sci USA 91(14): 6374-8).

Not only do the cytokine-stimulated immune and inflammatory responses contribute to normal host defense, they also play roles in the pathogenesis of diseases: pathologies such as severe combined immunodeficiency (SCID) arise from hypoactivity and suppression of the immune system, and a hyperactive or inappropriate immune/inflammatory response contributes to the pathology of autoimmune diseases such as rheumatoid and psoriatic arthritis, asthma and systemic lupus erythematosus, inflammatory bowel disease, multiple sclerosis, type I diabetes mellitus, myasthenia gravis, thyroiditis, immunoglobulin nephropathies, myocarditis as well as illnesses such as scleroderma and osteoarthritis (Ortmann, R. A., T. Cheng, et al. (2000). "Janus kinases and signal transducers and activators of transcription: their roles in cytokine signaling, development and immunoregulation." Arthritis Res 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." J Clin Invest 109(10): 1261-9). Thus, therapeutic agents are typically aimed at augmentation or suppression of the immune and inflammatory pathways, accordingly.

Deficiencies in expression of JAK family members are associated with disease states. Jak1−/− mice are runted at birth, fail to nurse, and die perinatally (Rodig, S. J., M. A. Meraz, et al. (1998). "Disruption of the Jak1 gene demonstrates obligatory and nonredundant roles of the Jaks in cytokine-induced biologic responses." Cell 93(3): 373-83). Jak2−/− mouse embryos are anemic and die around day 12.5 postcoitum due to the absence of definitive erythropoiesis. JAK2-deficient fibroblasts do not respond to IFNgamma, although responses to IFNalpha/beta and IL-6 are unaffected. JAK2 functions in signal transduction of a specific group of cytokine receptors required in definitive erythropoiesis (Neubauer, H., A. Cumano, et al. (1998). Cell 93(3): 397-409; Parganas, E., D. Wang, et al. (1998). Cell 93(3): 385-95).

JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." Blood 90(10): 3996-4003).

The JAK/STAT pathway, and in particular all four members of the JAK family, are believed to play a role in the pathogenesis of the asthmatic response, chronic obstructive pulmonary disease, bronchitis, and other related inflammatory diseases of the lower resporiatory tract. For instance, the inappropriate immune responses that characterize asthma are orchestrated by a subset of CD4+ T helper cells termed T helper 2 (Th2) cells. Signaling through the cytokine receptor IL-4 stimulates JAK1 and JAK3 to activate STAT6, and signaling through IL-12 stimulates activation of JAK2 and TYK2, and subsequent phosphorylation of STAT4. STAT4 and STAT6 control multiple aspects of CD4+ T helper cell differentiation (Pernis, A. B. and P. B. Rothman (2002). "JAK-STAT signaling in asthma." J Clin Invest 109(10): 1279-83). Furthermore, TYK2-deficient mice were found to have enhanced Th2 cell-mediated allergic airway inflammation (Seto, Y., H. Nakajima, et al. (2003). "Enhanced Th2 cell-mediated allergic inflammation in Tyk2-deficient mice." J Immunol 170(2): 1077-83). Moreover, multiple cytokines that signal through JAK kinases have been linked to inflammatory diseases or conditions of the upper respiratory tract such as those affecting the nose and sinuses (e.g. rhinitis, sinusitis) whether classically allergic reactions or not.

The JAK/STAT pathway has also been implicated to play a role in inflammatory diseases/conditions of the eye including, but not limited to, iritis, uveitis, scleritis, conjunctivitis, as well as chronic allergic responses. Therefore, inhibition of JAK kinases may have a beneficial role in the therapeutic treatment of these diseases.

The JAK/STAT pathway, and in particular, JAK3, also plays a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with replication of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." Proc Natl Acad Sci USA 94(25): 13897-902).

Blocking signal transduction at the level of the JAK kinases holds promise for developing treatments for human cancers. Cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) pathways. In IL-6-dependent MM cell lines treated with the JAK2 inhibitor tyrphostin AG490, JAK2 kinase activity and ERK2 and STAT3 phosphorylation were inhibited. Furthermore, cell proliferation was suppressed and apoptosis was induced (De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8). However, in some cases, AG490 can induce dormancy of tumor cells and actually then protect them from death.

Activation of JAK/STAT in cancers may occur by multiple mechanisms including cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., Neoplasm. 49:349-355, 2002). Importantly, activation of STAT signaling, as well as other pathways downstream of JAKs (e.g. Akt), has been correlated with poor prognosis in many cancer types (Bowman, T., et al. Oncogene 19:2474-2488, 2000). Moreover, elevated levels of circulatin cytokines that signal through JAK/STAT may adversely impact patient health as they are thought to play a causal role in cachexia and/or chronic fatigue. As such, JAK inhibition may be therapeutic for the treatment of cancer patients for reasons that extend beyond potential anti-tumor activity. The cachexia indication may gain further mechanistic support with realization that the satiety factor leptin signals through JAKs.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." Am J Transplant 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." Clin Immunol 106(3): 213-25).

It has been suggested that inhibition of JAK2 tyrosine kinase can be beneficial for patients with myeloproliferative disorder. (Levin, et al., Cancer Cell, vol. 7, 2005: 387-397) Myeloprofiferative disorder (MPD) includes polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES) and systemic mast cell disease (SMCD). Although the myeloproliferative disorder (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic acticing mutation in the JAK2 tyrosine kinase. It has also been reported that inhibition of the JAK2V617F kinase with a small molecule inhibitor leads to inhibition of proliferation of hematopoietic cells, suggesting that the JAK2 tyrosine kinase is a potential target for pharmacologic inhibition in patients with PV, ET and MMM.

Inhibition of the Jak kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, Nat Rev Drug Disc., 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins-2, -4, -6, -7, -12, -15, -18, and -23 as well as GM-CSF and IFNg, signal through the Janus (Jak) kinases (Adv Pharmacol. 2000; 47:113-74). As such, blocking signal transduction at the level of Jak kinases may result in therapeutic benefits in patients suffering from psoriasis or other immune disorders of the skin.

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in inability to continue the treatment. Although the driving force behind these immune reactions has not been elucidated completely at the present time, these immune reactions are likely linked to immune infiltrate.

Inhibitors of Janus kinases or related kinases are widely sought and several publications report effective classes of compounds. Examples of certain JAK inhibitors are reported in U.S. Pat. No. 6,852,727, WO 2003/011285, and U.S. Pat. App. Pub. No. 2006/0106020.

Thus, new or improved agents which inhibit Janus kinases are continually needed that act as immunosuppressive agents for organ transplants, as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease), diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds, compositions and methods described herein are directed toward these needs and other ends.

SUMMARY OF THE INVENTION

The present invention, inter alia, provides compounds of Formula Ia, Ib, or Ic:

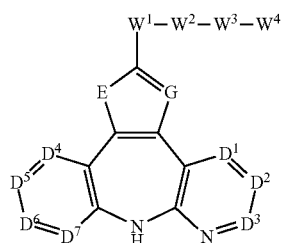

Ia

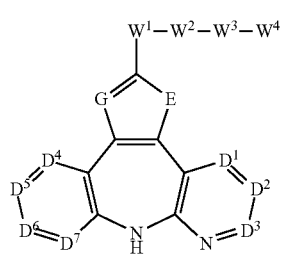

Ib

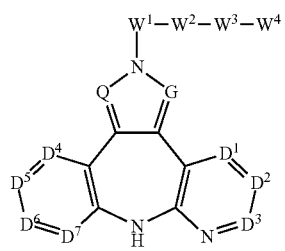

Ic

The present invention further provides compositions comprising a compound of Formula Ia, Ib, or Ic and a pharmaceutically acceptable carrier.

The present invention further provides methods of modulating an activity of JAK comprising contacting JAK with a compound of Formula Ia, Ib, or Ic.

The present invention further provides a method of treating a disease in a patient, where the disease is associated with JAK activity, by administering to the patient a therapeutically effective amount of a compound of Formula Ia, Ib, or Ic.

The present invention further provides a compound of the invention for use in therapy.

The present invention further provides a compound of the invention for use in the preparation of a medicament for use in therapy.

DETAILED DESCRIPTION

The present invention provides, inter alia, compounds of Formula Ia, Ib, or Ic:

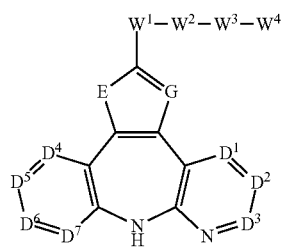

Ia

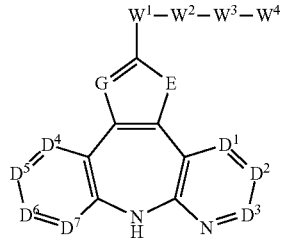

Ib

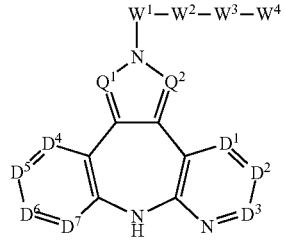

Ic or pharmaceutically acceptable salt or prodrug thereof, wherein:

$D^1$, $D^2$, $D^3$, $D^4$, $D^5$, $D^6$ and $D^7$ are, independently, $CR^1$ or N;

E is O, S, SO, $SO_2$, or $NR^{2a}$;

G is N or $CR^{2b}$;

$Q^1$ and $Q^2$ are each, independently, N or $CR^{2c}$;

$W^1$ is absent, $C_{1-6}$ alkyl, $C_{2-6}$ alkenyl, $C_{2-6}$ alkynyl, O, S, $NR^3$, CO, COO, $CONR^3$, SO, $SO_2$, $SONR^3$, $SO_2NR^3$, or $NR^3CONR^4$, wherein said $C_{1-6}$ alkyl, $C_{2-6}$ alkenyl or $C_{2-6}$ alkynyl is optionally substituted by 1, 2 or 3 substituents independently selected from halo, OH, $C_{1-4}$ alkoxy, $C_{1-4}$ haloalkoxy, amino, $C_{1-4}$ alkylamino and $C_{2-8}$ dialkylamino;

$W^2$ is absent, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2, or 3 substituents independently selected from halo, CN, $NO_2$, OH, =NH, =NOH, =NO—($C_{1-4}$ alkyl), —$NR^3C(O)O$—($C_{1-4}$ alkyl), $NR^3C(O)$—($C_{1-4}$ alkyl), —$C(O)O$—($C_{1-4}$ alkyl), $C_{1-4}$ haloalkyl, $C_{1-4}$ cyanoalkyl, pentahalosulfanyl, $C_{1-4}$ hydroxylalkyl, $C_{1-4}$ alkylthio, $C_{1-4}$ haloalkylthio, $C_{1-4}$ alkoxy, $C_{1-4}$ haloalkoxy, amino, $C_{1-4}$ alkylamino and $C_{2-8}$ dialkylamino;

$W^3$ is absent, $C_{1-6}$ alkyl, $C_{2-6}$ alkenyl, $C_{2-6}$ alkynyl, O, S, $NR^3$, =N—, =N—O—, =N—O—($C_{1-4}$ alkyl)-, O—($C_{1-4}$ alkyl), S—($C_{1-4}$ alkyl), $NR^3$—($C_{1-4}$ alkyl), ($C_{1-4}$ alkyl)-O—($C_{1-4}$ alkyl), ($C_{1-4}$ alkyl)-S—($C_{1-4}$ alkyl), ($C_{1-4}$ alkyl)-$NR^3$—($C_{1-4}$ alkyl), CO, COO, C(O)—($C_{1-4}$ alkyl), C(O)O—($C_{1-4}$ alkyl), C(O)—($C_{1-4}$ alkyl)-C(O), $NR^3C(O)$—($C_{1-4}$ alkyl), $C(O)NR^3$—($C_{1-4}$ alkyl), $NR^3C(O)O$—($C_{1-4}$ alkyl), $NR^3C(O)$O, $CONR^3$, SO, $SO_2$, $SONR^3$, $SO_2NR^3$, or $NR^3CONR^4$, wherein said $C_{1-6}$ alkyl, $C_{2-6}$ alkenyl or $C_{2-6}$ alkynyl is optionally substituted by 1, 2 or 3 substituents independently selected from halo, OH, CN, $C_{1-4}$ alkoxy, $C_{1-4}$ haloalkoxy, amino, $C_{1-4}$ alkylamino and $C_{2-8}$ dialkylamino;

$W^4$ is H, $NR^3R^4$, CN, $C_{1-6}$ alkyl, $C_{2-6}$ alkenyl, $C_{2-6}$ alkynyl, aryl, cycloalkyl, heteroaryl or heterocycloalkyl, wherein each of said $C_{1-6}$ alkyl, $C_{2-6}$ alkenyl, $C_{2-6}$ alkynyl, aryl, cycloalkyl, heteroaryl or heterocycloalkyl is optionally substituted by 1, 2, 3, 4 or 5 substituents independently selected from halo, OH, CN, $C_{1-4}$ alkoxy, =NH, =NOH, =NO—($C_{1-4}$ alkyl), $C_{1-4}$ haloalkyl, $C_{1-4}$ haloalkoxy, pentahalosulfanyl, COOH, $CONH_2$, COO—($C_{1-4}$ alkyl), amino, $C_{1-4}$ alkylamino and $C_{2-8}$ dialkylamino;

$R^1$ is, independently, H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $NR^cC(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $NR^cS(O)NR^cR^d$, pentahalosulfanyl, $S(O)_2R^b$, or $S(O)_2NR^cR^d$;

$R^{2a}$ is H, $C_{1-4}$ alkyl, $C_{2-4}$ alkenyl, $C_{2-4}$ alkynyl, OH, $C_{1-4}$ alkoxy, $C(O)R^b$, $C(O)NR^cR^d$, $S(O)R^b$, $S(O)NR^cR^d$, $S(O)_2R^b$, or $S(O)_2NR^cR^d$;

$R^{2b}$ and $R^{2c}$ are each, independently, H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cC(O)NR^cR^d$, $NR^cR^d$, $NR^cC(O)R^d$, $NR^cC(O)OR^a$, $S(O)R^b$, $S(O)NR^cR^d$, $NR^cS(O)NR^cR^d$, $S(O)_2R^b$, or $S(O)_2NR^cR^d$;

$R^3$ and $R^4$ are each, independently, H, $C_{1-6}$ alkyl, $C_{2-6}$ alkenyl, $C_{2-6}$ alkynyl, aryl, cycloalkyl, arylalkyl, cycloalkylalkyl, $COOR^{a'}$, $COR^{b'}$, $SOR^{b'}$, or $SO_2R^{b'}$ wherein each of said $C_{1-6}$ alkyl, $C_{2-6}$ alkenyl, $C_{2-6}$ alkynyl, aryl, cycloalkyl, arylalkyl, or cycloalkylalkyl is optionally substituted by 1, 2 or 3 substituents selected from halo, $C_{1-4}$ alkyl, $C_{1-4}$ haloalkyl, OH, $C_{1-4}$ alkoxy, $C_{1-4}$ haloalkoxy, amino, $C_{1-4}$ alkylamino, $C_{2-8}$ dialkylamino, aminocarbonyl, $C_{1-4}$ alkylaminocarbonyl, $C_{2-8}$ dialkylaminocarbonyl, CN and $NO_2$;

or $R^3$ and $R^4$ together with the N atom to which they are attached form a heterocycloalkyl group optionally substituted by 1, 2 or 3 substituents selected from halo, $C_{1-4}$ alkyl, $C_{1-4}$ haloalkyl, OH, $C_{1-4}$ alkoxy, $C_{1-4}$ haloalkoxy, amino, $C_{1-4}$ alkylamino, $C_{2-8}$ dialkylamino, aminocarbonyl, $C_{1-4}$ alkylaminocarbonyl, and $C_{2-8}$ dialkylaminocarbonyl;

$R^a$ and $R^{a'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ and $R^{b'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; and $R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

In some embodiments, when $D^7$ is N, E is O or S, and G is N; then $-W^1-W^2-W^3-W^4$ is other than H.

In some embodiments, no more than two of $D^1$, $D^2$, and $D^3$ are N.

In some embodiments, no more than three of $D^4$, $D^5$, $D^6$, and $D^7$ are N.

In some embodiments, no more than two of $D^4$, $D^5$, $D^6$, and $D^7$ are N.

In some embodiments, the compound has Formula 1a.
In some embodiments, the compound has Formula Ib.
In some embodiments, the compound has Formula Ic.
In some embodiments, E is $NR^{2a}$.
In some embodiments, E is NH or NOH.
In some embodiments, G is N.
In some embodiments, E is NH or NOH and G is N.
In some embodiments, E is NH and G is N.
In some embodiments, the compound has Formula Ia, E is NH or NOH, and G is N.
In some embodiments, $Q^1$ is N and $Q^2$ is $CR^{2c}$.
In some embodiments, $Q^1$ is $CR^{2c}$ and $Q^2$ is N.
In some embodiments, each $D^1$, $D^2$, and $D^3$ is $CR^1$.
In some embodiments, each $D^1$, $D^2$, and $D^3$ is CH.
In some embodiments, each $D^4$, $D^5$, $D^6$, and $D^7$ is $CR^1$.
In some embodiments, each $D^4$, $D^5$, and $D^7$ is $CR^1$ and $D^6$ is N.
In some embodiments, $D^4$ and $D^7$ are CH.
In some embodiments, $D^5$ is $CR^1$ and $R^1$ is H or halo.
In some embodiments, $D^6$ is $CR^1$ and $R^1$ is halo.
In some embodiments, $D^6$ is CF.
In some embodiments, $D^6$ is N.
In some embodiments, $D^5$ is CH or CF.

In some embodiments, $-W^1-W^2-W^3-W^4$ is $C_{1-6}$ alkyl, aryl, arylalkyl, cycloalkyl, cycloalkylalkyl, heteroaryl, heteroarylalkyl, heterocycloalkyl or heterocycloalkylalkyl, each optionally substituted by 1, 2, or 3 halo, $C_{1-4}$ alkyl, $C_{1-4}$ haloalkyl, $C_{1-4}$ haloalkylcarbonyl, aryl, cycloalkyl, heteroaryl, heterocycloalkyl, —COOH, —COO—($C_{1-4}$ alkyl), OH, $C_{1-4}$ alkoxy, $C_{1-4}$ haloalkoxy, hydroxyalkyl, CN, cyanoalkyl, alkylthio, arylthio, haloalkylthio, alkylsulfinyl, alkylsulfonyl, arylsulfinyl, arylsulfonyl, aryloxy, cycloalkyloxy, arylalkyloxy, aminocarbonyl, aminocarbonylalkyl, cyanoalkylcarbonyl, formyl, alkylcarbonyl, amino, alkylamino, alkylcarbonylamino, alkyloxycarbonylamino, or dialkylamino optionally substituted by CN.

In some embodiments, $-W^1-W^2-W^3-W^4$ is $C_{1-6}$ alkyl, aryl, arylalkyl, cycloalkyl, heteroaryl, heterocycloalkyl, or heterocycloalkylalkyl, each optionally substituted by 1, 2, or 3 halo, $C_{1-4}$ alkyl, $C_{1-4}$ haloalkyl, $C_{1-4}$ haloalkylcarbonyl, aryl, —COO—($C_{1-4}$ alkyl), OH, $C_{1-4}$ alkoxy, $C_{1-4}$ haloalkoxy, hydroxyalkyl, CN, cyanoalkyl, alkylthio, haloalkylthio, alkylsulfinyl, alkylsulfonyl, arylalkyloxy, aminocarbonyl, aminocarbonylalkyl, cyanoalkylcarbonyl, formyl, alkylcarbonyl, alkyloxycarbonylamino, alkylcarbonylamino, or dialkylamino optionally substituted by CN.

In some embodiments, -W$^1$-W$^2$-W$^3$-W$^4$ is methyl, ethyl, propyl, butyl, pentyl, hexyl, phenyl, naphthyl, biphenyl, benzyl, phenylethyl, phenylpropyl, cyclopropyl, cyclohexyl, cyclohexenyl, bicyclo[2.2.1]hept-2-enyl, cyclopentyl, pyridyl, pyrryl, imidazolyl, isoxazolyl, thiazolyl, quinolinyl, piperidinyl, tetrahydrofuranyl, pyrrolidinyl, benzo[1,3]dioxolyl, (piperidin-4-yl)methyl, (piperidin-3-yl)methyl, (tetrahydropyran-4-yl)-methyl, (tetrahydrothiopyran-4-yl)-methyl, each optionally substituted by 1, 2, or 3 halo, $C_{1-4}$ alkyl, $C_{1-4}$ haloalkyl, $C_{1-4}$ haloalkylcarbonyl, aryl, —COO—($C_{1-4}$ alkyl), OH, $C_{1-4}$ alkoxy, $C_{1-4}$ haloalkoxy, hydroxyalkyl, CN, cyanoalkyl, cyanoalkylcarbonyl, alkylthio, haloalkylthio, alkylsulfinyl, alkylsulfonyl, arylalkyloxy, aminocarbonyl, aminocarbonylalkyl, cyanoalkylcarbonyl, formyl, alkylcarbonyl, alkyloxycarbonylamino, alkylcarbonylamino, or dialkylamino optionally substituted by CN.

In some embodiments, -W$^1$-W$^2$-W$^3$-W$^4$ is phenyl, pyrazyl, pyrindyl, pyrryl, indolyl, furyl, thienyl, or benzothienyl, each optionally substituted by 1, 2, 3, 4, or 5 halo, $C_{1-4}$ alkyl, $C_{1-4}$ haloalkyl, aryl, OH, $C_{1-4}$ alkoxy, hydroxyalkyl, CN, cyanoalkyl, alkylthio, haloalkylthio, alkylsulfinyl, alkylsulfonyl, cycloalkyl, heterocycloalkyl, cycloalkylakyl, heterocyclyoalkylalkyl, amino, dialkylamino, aminoalkyl, or aminosulfonyl.

In some embodiments, the compound has Formula IIa or IIb:

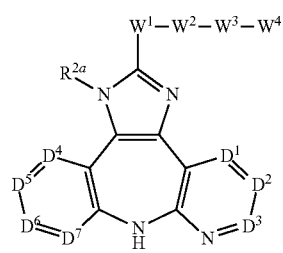
IIa

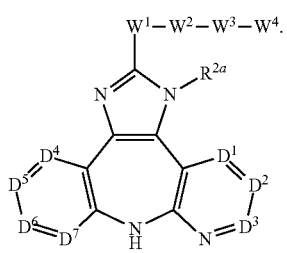
IIb

In some embodiments, the compound has Formula IIIa or IIIb:

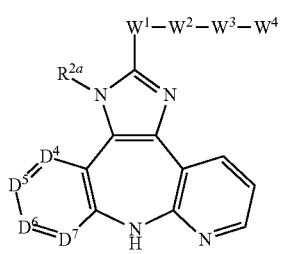
IIIa

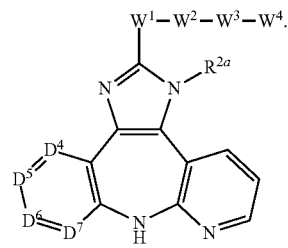
IIIb

In some embodiments, the compound has Formula IVa or IVb:

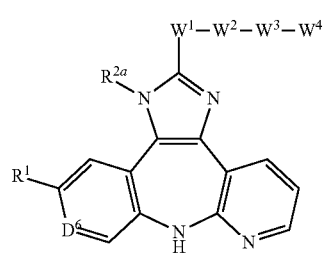
IVa

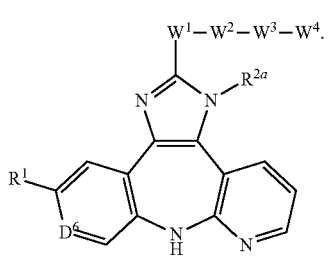
IVb

In some embodiments, the compound has Formula IVc or IVd:

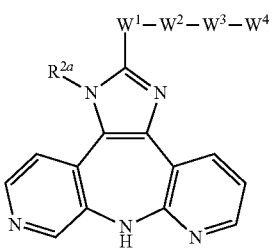
IVc

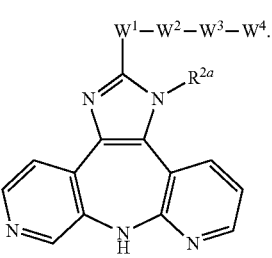
IVd

In some embodiments, the compound has Formula IVe:

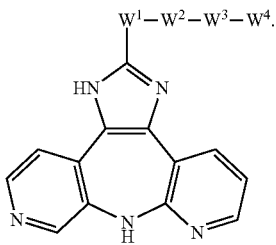

IVe

In some embodiments, the compound has Formula Va or Vb:

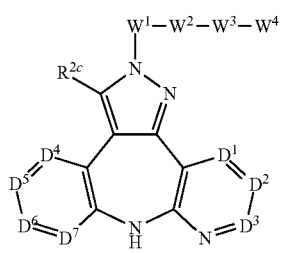

Va

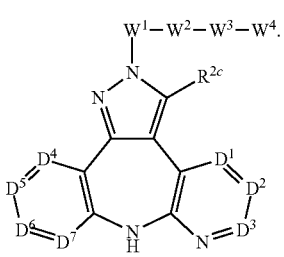

Vb

In some embodiments, the compound has Formula VIa or VIb:

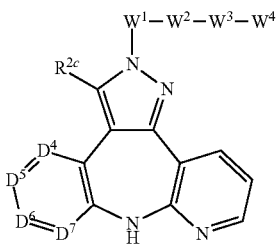

VIa

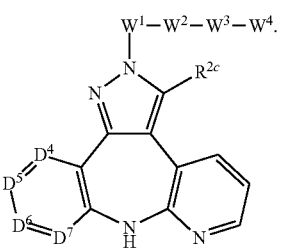

VIb

In some embodiments, the compound has Formula VIIa or VIIb:

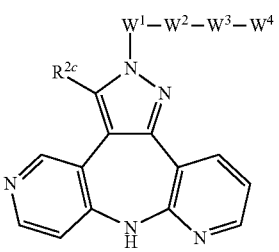

VIIa

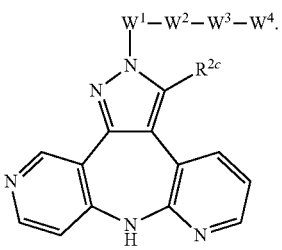

VIIb

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more double carbon-carbon bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of cyclopentane, cylcopentene, cyclohexane, and the like. A cycloalkyl group containing a fused aromatic ring can be attached through any ring-forming atom including a ring-forming atom of the fused aromatic ring.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups include monocyclic and polycyclic (e.g., having 2, 3 or 4 fused rings) systems. A heterocycloalkyl group can be attached through a ring-forming carbon atom or a ring-forming heteroatom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. A heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds.

As used herein, "halo" or "halogen" includes fluoro, chloro, bromo, and iodo.

As used herein, "arylalkyl" refers to alkyl substituted by aryl and "cycloalkylalkyl" refers to alkyl substituted by cycloalkyl. An example arylalkyl group is benzyl. An example cyclocalkylalkyl is cyclopropylmethyl.

As used herein, "alkoxy" or "alkyloxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "aryloxy" refers to an —O-aryl group. An example aryloxy is phenyloxy, i.e., —O-phenyl.

As used herein, "arylalkyloxy" refers to an arylalkyl-O— group (i.e. —O-alkyl-aryl). An example arylalkyloxy is benzyloxy.

As used here, "cylcoalkyloxy" refers to an —O-cycloalkyl group. An example cylcoalkyloxy group is —O-cylclopropyl.

As used herein, "heteroarylalkyl" refers to alkyl substituted by heteroaryl. An example of heteroarylalkyl is (pyridin-2-yl)-methyl.

As used herein, "heterocycloalkylalkyl" refers to alkyl substituted by heterocylcoalkyl. An example of heterocycloalkylalkyl is (tetrahydropyran-4-yl)-methyl.

As used herein, "cyano" refers to CN. The term "cyanoalkyl" refers to alkyl substituted by cyano.

As used herein, "hydroxyl" or "hydroxy" refers to —OH. The term "hydroxylalkyl" refers to alkyl substituted by hydroxyl.

As used herein, "alkylthio" refers to an —S-alkyl group. Example alkylthio groups include methylthio (—$SCH_3$), ethylthio (—$SCH_2CH_3$), and the like.

As used herein, "haloalkylthio" refers to an —S-haloalkyl group. An example haloalkylthio group is —$SCF_3$.

As used herein, "arylthio" refers to an —S-aryl group. An example arylthio group is —S-phenyl.

As used herein, "sulfinyl" refers to a bivalent group —S(O)—.

As used herein, "alkylsulfinyl" refers to —S(O)-alkyl.

As used herein, "arylsulfinyl" refers to —S(O)-aryl.

As used herein, "sulfonyl" refers to a bivalent group —$S(O)_2$—.

As used herein, "alkylsulfonyl" refers to —$S(O)_2$-alkyl.

As used herein, "arylsulfonyl" refers to —$S(O)_2$-aryl.

As used herein, "pentahalosulfanyl" refers to moieties of formula —$SX_5$ where each X is independently selected from F, Cl, Br, or I. For methods of preparing compounds containing pentahalosulfanyl groups see, e.g., *Org. Leu.* 2002, 4, 3013.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "carbonyl" refers to a bivalent group —C(O)—.

As used herein, "formyl" refers to —C(O)H.

As used herein, "alkylcarbonyl" refers to —C(O)-alkyl.

As used herein, "cyanoalkylcarbonyl" refers to —C(O)-(cyanoalkyl).

As used herein, "aminocarbonyl" refers to —C(O)NH$_2$.

As used herein, "aminoalkyl" refers to alkyl substituted by NH$_2$.

As used herein, "aminocarbonylalkyl" refers to alkyl substituted by aminocarbonyl.

As used herein, "alkylaminocarbonyl" refers to an aminocarbonyl group wherein the amino group is substituted by an alkyl group, i.e., —C(O)NH-alkyl.

As used herein, "dialkylaminocarbonyl" refers to an aminocarbonyl group wherein the amino group is substituted by two alkyl groups.

As used herein, "cyanoalkylaminocarbonyl" refers to —C(O)NH-(cyanoalkyl).

As used herein, "alkylcarbonylamino" refers to —NHC(O)-alkyl.

As used herein, "alkyloxycarbonylamino" refers to —NHC(O)—O-alkyl.

As used herein, the terms "alkyl", "alkenyl", "alkynyl", "aryl", "cycloalkyl", "heteroaryl", and "heterocycloalkyl" are also meant to encompass the corresponding divalent linking moieties (e.g., alkylenyl, alkenylenyl, etc.) when used in a linking context such as in variables $W^1$, $W^2$, and $W^3$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include all potential tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrated, solvated, anhydrate, and non-solvated solid forms.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can be in isolated form. An isolated compound is one that has been at least partially or substantially separated from the environment in which is was formed or discovered.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

Compounds of the invention, including salts, hydrates, and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

As shown in Scheme 1, compounds of formula 1-8 (R=-$W^1$-$W^2$-$W^3$-$W^4$) can be prepared according to the synthetic route outlined. 2-Fluoro-3-iodopyridine 1-1 (wherein m is 1, 2 or 3) can be synthesized using the methods described by Estel, L.; Marsais, F.; and Queguiner, G [Journal of Organic Chemistry (1988), 53(12), 2740-44]. Compounds of formula 1-1 can be coupled with a trialkylsilylacetylene such as trimethylsilyl acetylene in the presence of a palladium catalyst such as Pd(PPh$_3$)$_2$Cl$_2$ and an amine such as triethyl amine and CuI under Sonogashira conditions to give the coupling product 1-2. Compound of formula 1-2 can be desilylated by a fluoride salt such as tetrabutylammonium fluoride in an inert solvent such as tetrahydrofuran to give the acetylenic compounds of formula 1-3. Compounds of formula 3 can be coupled with 2-nitrohaloaryls or 2-nitroheteroaryls of formula 1-4 (X is a leaving group like halo) under Sonogashira conditions described earlier to give the coupled products of formula 1-5. Compounds of formula 1-5 can be oxidized to the corresponding diketones of formula 1-6 with the use of an oxidant such as KMnO$_4$ in a solvent such as acetone under conditions described by Srinivasan, N. S. and Lee Donald G. [Journal of Organic Chemistry (1979), 44(9), 1574]. Compounds of formula 1-6 can be converted to the compounds of formula 1-7 in the presence of an aldehyde RCHO(R=-$W^1$-$W^2$-$W^3$-$W^4$) and ammonium hydroxide. Compounds of formula 1-7 can be converted to compounds of formula 1-8 by reduction of the nitro group to the corresponding amine compound using a reducing agent such as Na$_2$S$_2$O$_4$ or Zn and acid, or by catalytic hydrogenation, followed by a cyclization reaction in which the amino group of the corresponding amine compound displaces the fluorine on the 2-position of the pyridine under thermal condition or acid or base catalysis.

Scheme 1

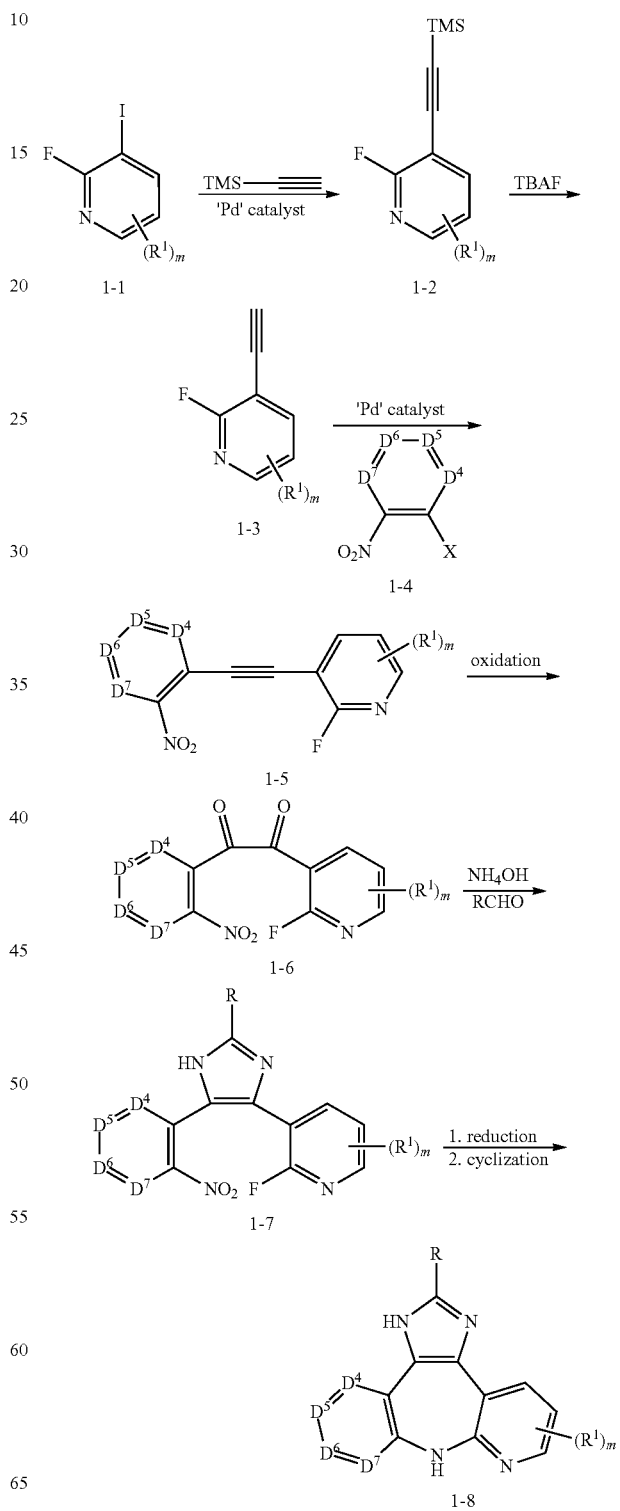

As shown in Scheme 2, compounds of formula 2-7 and/or 2-8 can be prepared by the synthetic route outlined. A nicotinic acid derivative 2-1 (J and J' can be halogen or other leaving group) can be treated with a secondary amine HNR'R" such as diethylamine to give the corresponding amide 2-2. Amide 2-2 can be coupled with an aryl- or heteroaryl-amine 2-3 by utilizing a base such as lithium, sodium or potassium hexamethyldisilazide, lithium, sodium or potassium dialkylamide, sodium hydride, or potassium hydride, in a solvent such as tetrahydrofuran, 1,4-dioxane, dimethylformamide, or dimethylsulfoxide to give the corresponding amine compound of formula 2-4. The compounds of formula 2-4 can be cyclized to the corresponding ketone 2-5 by treatment with a strong base such as a lithium dialkylamide in an organic solvent such as tetrahydrofuran. The compound of formula 2-5 can be converted to the corresponding ketoxime 2-6 by treatment with a nitrite such as $NaNO_2$ in acetic acid. Ketoxime 2-6 can be condensed with an aldehyde RCHO ($R=-W^1-W^2-W^3-W^4$) in a solvent such as acetic acid and in the presence of an ammonium salt such as ammonium acetate to the hydroxyl tetracyclic imidazole 2-7. The hydroxyl tetracyclic imidazole 2-7 can be deoxygenated by treatment with an appropriate reagent such as a trialkoxy phoshite or $TiCl_3$, to give a compound of formula 2-8.

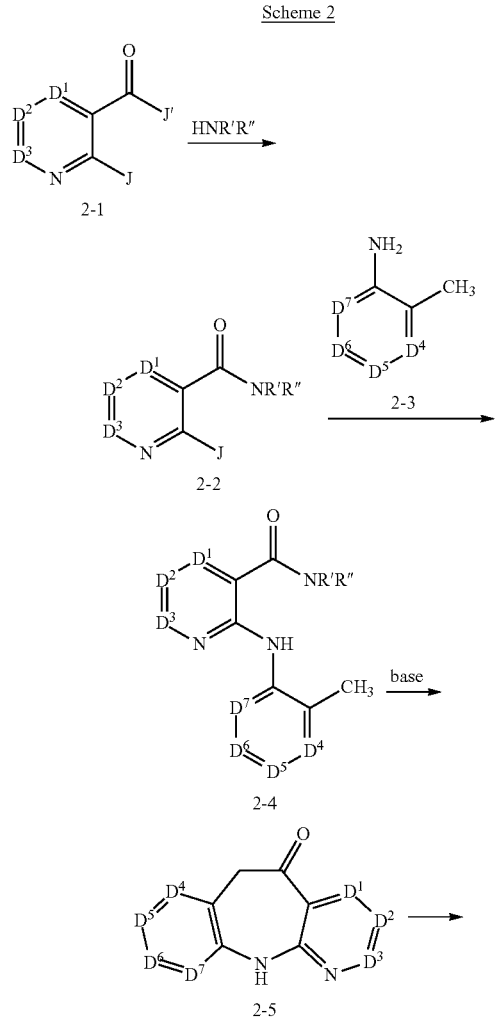

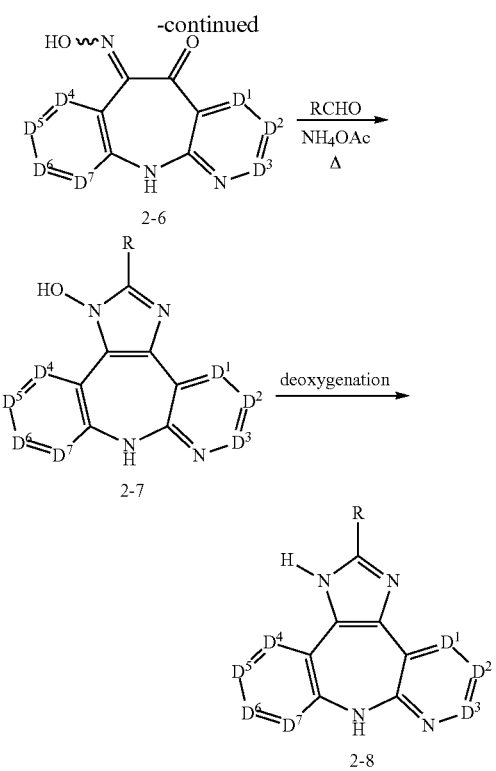

As outlined in Scheme 3, compounds of formula 2-5 can be prepared by an alternative synthetic route. Using a base such as butyllithium in a solvent such as tetrahydrofuran, the dianion of 3-2 (R is a suitable protecting group such as tert-butyloxycarbonyl) can be formed and added to a nicotinic aldehyde derivative 3-1 (J can be halogen or other leaving group) to provide the alcohol product 3-3. Removal of the Pr protecting group using acidic conditions such as trifluoroacetic acid provides the amine 3-4 which can be cyclized to the azepine 3-5 using a suitable base such as potassium tert-butoxide in a solvent such as tetrahydrofuran. Oxidation of the alcohol (using methods such as Dess-Martin periodinane, oxalyl chloride/dimethylsulfoxide (Swern), sulfur trioxide-pyridine complex/dimethylsulfoxide, or various chromium reagents) provides compounds of formula 2-5.

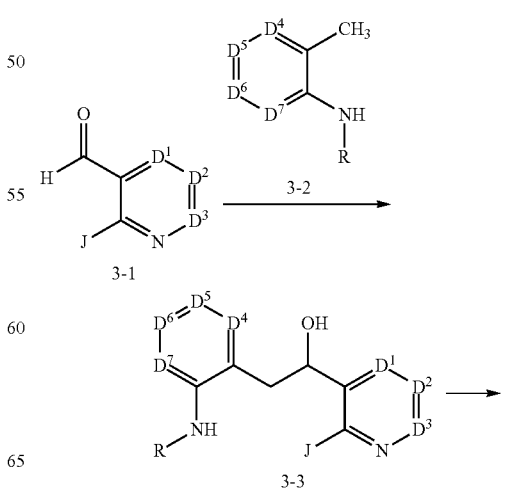

-continued

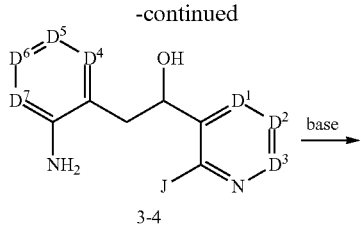
3-4

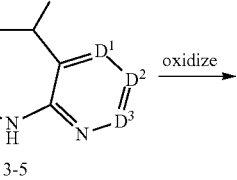
3-5

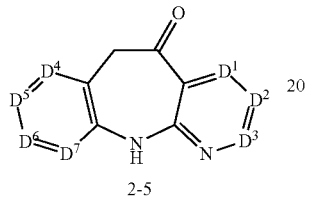
2-5

-continued

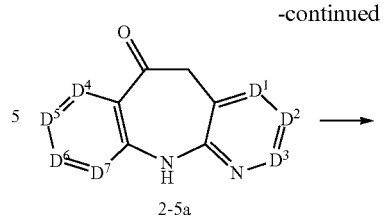

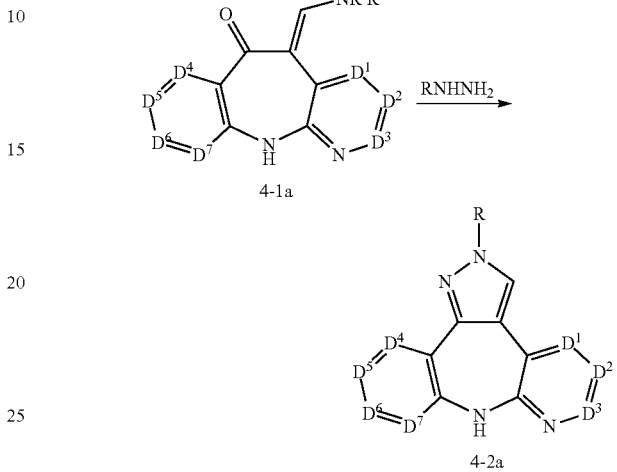

As outlined in Scheme 4, compounds of formula 2-5 can be converted to compounds of formula 4-2 by reacting the ketone 2-5 with a reagent such as 1,1-dimethoxy-N,N-dimethylmethanamine to provide the dialkylaminomethylene derivative 4-1 (R' and R" are alkyl groups such as methyl). A hydrazine derivative can then be added to 4-1 in a suitable solvent such as ethanol to provide pyrazole compounds of formula 4-2. Related ketones 2-5a can be made by analogous methods to those shown in Schemes 2 and 3 which can serve as the basis for preparations of related compounds 4-1a and 4-2a according to Scheme 4.

Scheme 4

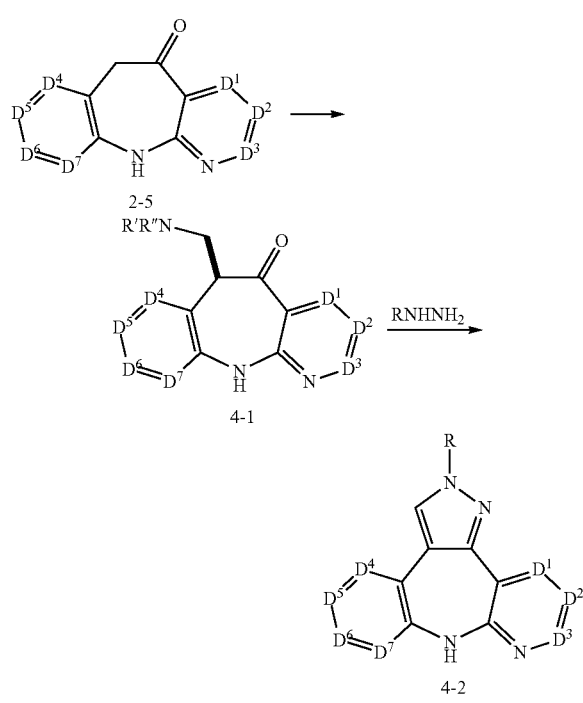

Methods

Compounds of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In some embodiments, compounds of the present invention can act to stimulate the activity of one or more JAKs. In further embodiments, the compounds of the invention can be used to modulate activity of a JAK in an individual in need of modulation of the receptor by administering a modulating amount of a compound of Formula Ia, Ib, or Ic.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2. In some embodiments, the JAK is JAK3.

The compounds of the invention can be selective. By "selective" is meant that the compound binds to or inhibits a JAK with greater affinity or potency, respectively, compared to at least one other JAK. In some embodiments, the compounds of the invention are selective inhibitors of JAK1 or JAK2 over JAK3 and/or TYK2. In some embodiments, the compounds of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the Km of each enzyme. In some embodiments, selectivity of compounds of the invention for JAK2 over JAK3 can be determined by the cellular ATP concentration.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, myasthenia gravis, immunoglobulin nephropathies, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, etc.), hematological cancers (e.g., lymphoma, leukemia such as acute lymphoblastic leukemia, or multiple myeloma), and skin cancer such as cutaneous T-cell lymphoma (CTCL) and cutaneous B-cell lymphoma. Example cutaneous T-cell lymphomas include Sezary syndrome and mycosis fungoides. In some embodiments, the cancer is of neuroectodermal and/or epidermal origin such as, for example, melanoma, basal cell carcinoma, squamous cell carcinoma, and the like.

JAK-associated diseases can further include those characterized by expression of a mutant JAK2 such as those having at least one mutation in the pseudo-kinase domain (e.g., JAK2V617F) or a mutant JAK3 (see, e.g., Walters, D. K. et al. *Cancer Cell,* 2006, 10, 65).

JAK-associated diseases can further include myeloproliferative disorders (MPDs) such as polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), systemic mast cell disease (SMCD), and the like.

Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest.

The JAK inhibitors described herein can further be used to treat anorexia, cachexia, or fatigue such as that resulting from or associated with cancer.

The JAK inhibitors described herein can further be used to treat rheumatoid arthritis, Kaposi's sarcoma, or Castleman's disease.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., arresting further development of the pathology and/or symptomatology), and (3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, or other agents can be used in combination with the compounds of the present invention for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, EP2005/009967, EP2005/010408, and U.S. Ser. No. 60/578, 491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethsone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro metalloprotease labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitering its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Tables 1 to 4 below provide example compounds of the invention that show activity as JAK inhibitors according to one or more of the assays provided herein. The compounds were prepared according to synthetic procedure of the Example compound specified in the column marked "Prep. Ex." and purified by the method in the column marked "Pur. Meth.", where A refers to purification by LCMS (HPLC, pH=2, trifluoroacetic acid (TFA)); B refers to purification by LCMS (HPLC, pH=10, NH$_4$OH), C refers to silica gel chromatography (typically hexanes/ethyl acetate), D refers to routine crystallization or precipitation methods, and E refers to the purification method as provided in the synthetic description for that compound. Certain compounds of the Tables were isolated in the free base form or as a salt (typically as a result of the purification procedure) as indicated in the column marked "Salt". The salt stoichiometry indicated in the below tables and preparation descriptions is typically based on theory and one skilled in the art would understand that the actual product might contain more or less acid. Actual stoichiometry can be determined by routine methods such as elemental analysis.

TABLE 1

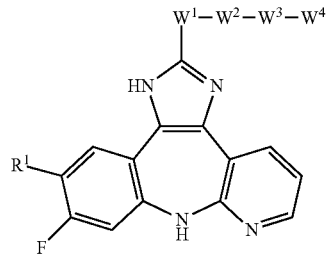

| Ex. No. | —W$^1$—W$^2$—W$^3$—W$^4$ | R$^1$ | MS (M + H) | Prep. Ex. | Pur. Meth. | Salt | Compound Name |
|---|---|---|---|---|---|---|---|
| 1 | *tert*-butyl | H | 309 | 1 | E | Free Base | 2-tert-butyl-10-fluoro-3,8-dihydroimidazo[4,5-d]pyrido[2,3-b][1]benzazepine |
| 2 | cyclopropyl | H | 293 | 1 | C | Free Base | 2-cyclopropyl-10-fluoro-3,8-dihydroimidazo[4,5-d]pyrido[2,3-b][1]benzazepine |
| 3 | cyclohexyl | H | 335 | 1 | C | Free Base | 2-cyclohexyl-10-fluoro-3,8-dihydroimidazo[4,5-d]pyrido[2,3-b][1]benzazepine |

TABLE 1-continued

| Ex. No. | —W¹—W²—W³—W⁴ | R¹ | MS (M + H) | Prep. Ex. | Pur. Meth. | Salt | Compound Name |
|---|---|---|---|---|---|---|---|
| 4 | isobutyl-CH₂– | H | 309 | 1 | C | Free Base | 10-fluoro-2-isobutyl-3,8-dihydroimidazo[4,5-d]pyrido[2,3-b][1]benzazepine |
| 5 | cyclopentyl | H | 321 | 1 | C | Free Base | 2-cyclopentyl-10-fluoro-3,8-dihydroimidazo[4,5-d]pyrido[2,3-b][1]benzazepine |
| 6 | tetrahydrofuran-3-yl | H | 323 | 1 | C | Free Base | 10-fluoro-2-(tetrahydrofuran-3-yl)-3,8-dihydroimidazo[4,5-d]pyrido[2,3-b][1]benzazepine |
| 7 | cyclohex-3-en-1-yl | H | 333 | 1 | C | Free Base | 2-cyclohex-3-en-1-yl-10-fluoro-3,8-dihydroimidazo[4,5-d]pyrido[2,3-b][1]benzazepine |
| 8 | EtO₂C-cyclopropyl | H | 365 | 1 | C | Free Base | Trans ethyl (1R,S)-2-(10-fluoro-3,8-dihydroimidazo[4,5-d]pyrido[2,3-b][1]benzazepin-2-yl)cyclopropanecarboxylate |
| 9 | bicyclo[2.2.1]hept-5-en-2-yl | H | 345 | 1 | C | Free Base | 2-bicyclo[2.2.1]hept-5-en-2-yl-10-fluoro-3,8-dihydroimidazo[4,5-d]pyrido[2,3-b][1]benzazepine |
| 10 | HOH₂C-cyclopropyl | H | 323 | 1 | A | TFA | [(1S)-2-(10-fluoro-3,8-dihydroimidazo[4,5-d]pyrido[2,3-b][1]benzazepin-2-yl)cyclopropyl]methanol trifluoroacetate |
| 11 | 1-ethylpentyl | H | 351 | 1 | C | Free Base | 2-(1-ethylpentyl)-10-fluoro-3,8-dihydroimidazo[4,5-d]pyrido[2,3-b][1]benzazepine |
| 12 | NC-(4-ethyl)hexyl | H | 376 | 1 | C | Free Base | 4-ethyl-4-(10-fluoro-3,8-dihydroimidazo[4,5-d]pyrido[2,3-b][1]benzazepin-2-yl)hexanenitrile |
| 13 | cyclopentyl | F | 339 | 1 | C | Free Base | 2-cyclopentyl-10,11-difluoro-3,8-dihydroimidazo[4,5-d]pyrido[2,3-b][1]benzazepine |

TABLE 1-continued

| Ex. No. | —W¹—W²—W³—W⁴ | R¹ | MS (M + H) | Prep. Ex. | Pur. Meth. | Salt | Compound Name |
|---|---|---|---|---|---|---|---|
| 14 | (1-ethylpentyl group) | F | 369 | 1 | C | Free Base | 2-(1-ethylpentyl)-10,11-difluoro-3,8-dihydroimidazo[4,5-d]pyrido[2,3-b][1]benzazepine |
| 15 | (cyclohexyl-CH2CH2CN) | H | 388 | 1 | C | Free Base | 3-[1-(10-fluoro-3,8-dihydroimidazo[4,5-d]pyrido[2,3-b][1]benzazepin-2-yl)cyclohexyl]propanenitrile |
| 16 | (NC-CH2CH2-C(CH3)2-) | H | 348 | 1 | C | Free Base | 4-(10-fluoro-3,8-dihydroimidazo[4,5-d]pyrido[2,3-b][1]benzazepin-2-yl)-4-methylpentanenitrile |
| 17 | (1-ethylpropyl) | H | 323 | 1 | C | Free Base | 2-(1-ethylpropyl)-10-fluoro-3,8-dihydroimidazo[4,5-d]pyrido[2,3-b][1]benzazepine |
| 18 | (CH3-S-CH2CH2-) | H | 327 | 1 | C | Free Base | 10-fluoro-2-[2-(methylthio)ethyl]-3,8-dihydroimidazo[4,5-d]pyrido[2,3-b][1]benzazepine |
| 19 | (CH3-S(O)-CH2CH2-) | H | 343 | 1 | C | Free Base | 10-fluoro-2-[2-(methylsulfinyl)ethyl]-3,8-dihydroimidazo[4,5-d]pyrido[2,3-b][1]benzazepine |
| 20 | (Ph-CH2-O-CH2-) | H | 373 | 1 | C | Free Base | 2-[(benzyloxy)methyl]-10-fluoro-3,8-dihydoimidazo[4,5-d]pyrido[2,3-b][1]benzazepine |
| 21 | (cis-HOCH2-cyclohexyl-) | H | 365 | 1 | C | Free Base | Cis-[4-(10-fluoro-3,8-dihydroimidazo[4,5-d]pyrido[2,3-b][1]benzazepin-2-yl)cyclohexyl]methanol |
| 22 | (trans-HOCH2-cyclohexyl-) | H | 365 | 1 | C | Free Base | Trans-[4-(10-fluoro-3,8-dihydroimidazo[4,5-d]pyrido[2,3-b][1]benzazepin-2-yl)cyclohexyl]methanol |
| 23 | (cis-HO-cyclohexyl-) | H | 351 | 1 | C | Free Base | Cis-4-(10-fluoro-3,8-dihydroimidazo[4,5-d]pyrido[2,3-b][1]benzazepin-2-yl)cyclohexanol |

TABLE 1-continued

| Ex. No. | —W¹—W²—W³—W⁴ | R¹ | MS (M + H) | Prep. Ex. | Pur. Meth. | Salt | Compound Name |
|---|---|---|---|---|---|---|---|
| 24 | HO‴–cyclohexyl– | H | 351 | 1 | C | Free Base | Trans-4-(10-fluoro-3,8-dihydroimidazo[4,5-d]pyrido[2,3-b][1]benzazepin-2-yl)cyclohexanol |
| 25 | NC–CH₂–cyclohexyl– | H | 374 | 25 | C | Free Base | Trans-[4-(10-fluoro-3,8-dihydroimidazo[4,5-d]pyrido[2,3-b][1]benzazepin-2-yl)cyclohexyl]acetonitrile |
| 26 | H₂NOC–CH₂–cyclohexyl– | H | 392 | 1 | D | Free Base | 2-[4-(10-fluoro-3,8-dihydroimidazo[4,5-d]pyrido[2,3-b][1]benzazepin-2-yl)cyclohexyl]acetamide |
| 27 | tBuO₂C—N(piperidinyl)– | H | 436 | 1 | C | Free Base | tert-butyl 4-(10-fluoro-3,8-dihydroimidazo[4,5-d]pyrido[2,3-b][1]benzazepin-2-yl)piperidine-1-carboxylate |
| 28 | HN(piperidinyl)– | H | 336 | 1 | D | Free Base | 10-fluoro-2-piperidin-4-yl-3,8-dihydroimidazo[4,5-d]pyrido[2,3-b][1]benzazepine |
| 29 | NC–CH₂–C(O)–N(piperidinyl)– | H | 403 | 1 | C | Free Base | 3-[4-(10-fluoro-3,8-dihydroimidazo[4,5-d]pyrido[2,3-b][1]benzazepin-2-yl)piperidin-1-yl]-3-oxopropanenitrile |
| 30 | CH₃C(O)–N(piperidinyl)– | H | 378 | 1 | C | Free Base | 2-(1-acetylpiperidin-4-yl)-10-fluoro-3,8-dihydroimidazo[4,5-d]pyrido[2,3-b][1]benzazepine |
| 31 | CH₃SO₂–N(piperidinyl)– | H | 414 | 1 | C | Free Base | 10-fluoro-2-[1-(methylsulfonyl)piperidin-4-yl]-3,8-dihydroimidazo[4,5-d]pyrido[2,3-b][1]benzazepine |
| 32 | NC–CH₂–N(piperidinyl)– | H | 375 | 1 | C | Free Base | [4-(10-fluoro-3,8-dihydroimidazo[4,5-d]pyrido[2,3-b][1]benzazepin-2-yl)piperidin-1-yl]acetonitrile |

TABLE 1-continued

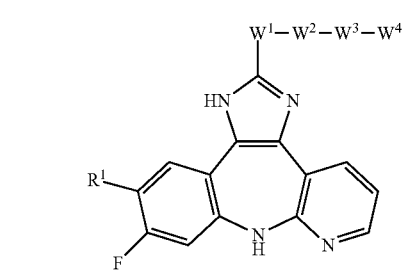

| Ex. No. | —W¹—W²—W³—W⁴ | R¹ | MS (M + H) | Prep. Ex. | Pur. Meth. | Salt | Compound Name |
|---|---|---|---|---|---|---|---|
| 33 | 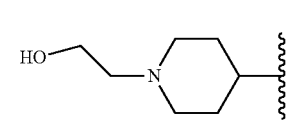 EtO₂C, piperidine | H | 422 | 1 | C | Free Base | ethyl [4-(10-fluoro-3,8-dihydroimidazo[4,5-d]pyrido[2,3-b][1]benzazepin-2-yl)piperidin-1-yl]acetate |
| 34 | HO, piperidine | H | 380 | 1 | C | Free Base | 2-[4-(10-fluoro-3,8-dihydroimidazo[4,5-d]pyrido[2,3-b][1]benzazepin-2-yl)piperidin-1-yl]ethanol |
| 35 | HO, piperidine | H | 394 | 1 | C | Free Base | 3-[4-(10-fluoro-3,8-dihydroimidazo[4,5-d]pyrido[2,3-b][1]benzazepin-2-yl)piperidin-1-yl]propan-1-ol |
| 36 | NC, piperidine | H | 403 | 1 | C | Free Base | 4-[4-(10-fluoro-3,8-dihydroimidazo[4,5-d]pyrido[2,3-b][1]benzazepin-2-yl)piperidin-1-yl]butanenitrile |
| A-1 | pyrazole-CF₃ | H | 401 | 1 | D | Free Base | 10-fluoro-2-[3-methyl-5-(trifluoromethyl)-1H-pyrazol-4-yl]-3,8-dihydroimidazo[4,5-d]pyrido[2,3-b][1]benzazepine |
| A-2 | pyrazole-CHF₂ | H | 383 | 1 | D | Free Base | 2-[3-(difluoromethyl)-5-methyl-1H-pyrazol-4-yl]-10-fluoro-3,8-dihydroimidazo[4,5-d]pyrido[2,3-b][1]benzazepine |
| A-3 | dimethyl pyrazole | H | 347 | 1 | C | Free Base | 2-(3,5-dimethyl-1H-pyrazol-4-yl)-10-fluoro-3,8-dihydroimidazo[4,5-d]pyrido[2,3-b][1]benzazepine |

TABLE 1-continued

| Ex. No. | —W$^1$—W$^2$—W$^3$—W$^4$ | R$^1$ | MS (M + H) | Prep. Ex. | Pur. Meth. | Salt | Compound Name |
|---|---|---|---|---|---|---|---|
| A-4 | 3,5-diethyl-1H-pyrazol-4-yl | H | 375 | 1 | C | Free Base | 2-(3,5-diethyl-1H-pyrazol-4-yl)-10-fluoro-3,8-dihydroimidazo[4,5-d]pyrido[2,3-b][1]benzazepine |
| A-5 | 1-(cyanomethyl)-5-methyl-3-(trifluoromethyl)-1H-pyrazol-4-yl | H | 440 | 1 | C | Free Base | [4-(10-fluoro-3,8-dihydroimidazo[4,5-d]pyrido[2,3-b][1]benzazepin-2-yl)-5-methyl-3-(trifluoromethyl)-1H-pyrazol-1-yl]acetonitrile |
| A-6 | 2-chloro-6-methylphenyl | H | 377 | 1 | A | TFA | 2-(2-chloro-6-methylphenyl)-10-fluoro-3,8-dihydroimidazo[4,5-d]pyrido[2,3-b][1]benzazepine trifluoroacetate |
| A-7 | 2-cyano-6-methylphenyl | H | 368 | 1 | A | TFA | 2-(10-fluoro-3,8-dihydroimidazo[4,5-d]pyrido[2,3-b][1]benzazepin-2-yl)-3-methylbenzonitrile trifluoroacetate |
| A-7a | 2,6-dimethylphenyl | H | 357 | 1 | A | TFA | 2-(2,6-dimethylphenyl)-10-fluoro-3,8-dihydroimidazo[4,5-d]pyrido[2,3-b][1]benzazepine trifluoroacetate |
| A-7b | 3,5-dichloropyridin-4-yl | H | 398 | 1 | A | 2 TFA | 2-(3,5-dichloropyridin-4-yl)-10-fluoro-3,8-dihydroimidazo[4,5-d]pyrido[2,3-b][1]benzazepine bis(trifluoroacetate) |

TABLE 1-continued

| Ex. No. | —W¹—W²—W³—W⁴ | R¹ | MS (M + H) | Prep. Ex. | Pur. Meth. | Salt | Compound Name |
|---|---|---|---|---|---|---|---|
| A-8 | 2,4-dimethylpyridin-3-yl | H | 358 | 1 | A | 2 TFA | 2-(2,4-dimethylpyridin-3-yl)-10-fluoro-3,8-dihydroimidazo[4,5-d]pyrido[2,3-b][1]benzazepine bis(trifluoroacetate) |

TABLE 2

| Ex. No. | —W¹—W²—W³—W⁴ | R²ᵃ | MS | Prep Ex | Pur Ex | Salt | Compound Name |
|---|---|---|---|---|---|---|---|
| 37 | NC-CH₂CH₂-C(Et)(vinyl)- | H | 359 | 41 | C | Free Base | 4-(3,8-dihydroimidazo[4,5-d]dipyrido[2,3-b:4',3'-f]azepin-2-yl)-4-ethylhexanenitrile |
| 38 | 4-(hydroxymethyl)cyclohexyl | OH | 364 | 41 | C | Free Base | 2-[4-(hydroxymethyl)-cyclohexyl]-imidazo[4,5-d]dipyrido[2,3-b:4',3'-f]azepin-3(8H)-ol |
| 39 | 4-(hydroxymethyl)cyclohexyl | H | 348 | 41 | C | Free Base | [4-(3,8-dihydroimidazo[4,5-d]dipyrido[2,3-b:4',3'-f]azepin-2-yl)cyclohexyl]methanol |
| 40 | 4-(cyanomethyl)cyclohexyl | OH | 373 | 41 | C | Free Base | [4-(3-hydroxy-3,8-dihydroimidazo[4,5-d]dipyrido[2,3-b:4',3'-f]azepin-2-yl)cyclohexyl]aceto-nitrile |
| 41 | 4-(cyanomethyl)cyclohexyl | H | 357 | 41 | E | Free Base | [4-(3,8-dihydroimidazo[4,5-d]dipyrido[2,3-b:4',3'-f]azepin-2-yl)cyclohexyl]acetonitrile |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 42 | NC—C(CH₃)₂—CH₂— | H | 317 | 41 | C | Free Base | 3-(3,8-dihydroimidazo[4,5-d]dipyrido[2,3-b:4',3'-f]azepin-2-yl)-3-methylbutanenitrile |
| 43 | NC—CH₂—C(Et)(vinyl)— | H | 345 | 41 | B | Free Base | 3-(3,8-dihydroimidazo[4,5-d]dipyrido[2,3-b:4',3'-f]azepin-2-yl)-3-ethylpentanenitrile |
| 44 | NC—CH₂—cyclopentyl— | H | 343 | 41 | C | Free Base | [3-(3,8-dihydroimidazo[4,5-d]dipyrido[2,3-b:4',3'-f]azepin-2-yl)cyclopentyl]acetonitrile |
| 45 | NC—cyclopentyl— | H | 329 | 41 | C | Free Base | 3-(3,8-dihydroimidazo[4,5-d]dipyrido[2,3-b:4',3'-f]azepin-2-yl)cyclopentanecarbonitrile |
| 46 | 3,5-dichloropyridin-4-yl | H | 381 | 46 | A | 3 TFA | 2-(3,5-dichloropyridin-4-yl)-3,8-dihydroimidazo[4,5-d]dipyrido[2,3-b:4',3'-f]azepine tris(trifluoroacetate) |
| 47 | 2,6-dichlorophenyl | H | 380 | 47 | E | 2 HCl | 2-(2,6-dichlorophenyl)-3,8-dihydroimidazo[4,5-d]dipyrido[2,3-b:4',3'-f]azepine dihydrochloride |
| 48 | 2,6-dimethylphenyl | H | 340 | 46 | A | 2 TFA | 2-(2,6-dimethylphenyl)-3,8-dihydroimidazo[4,5-d]dipyrido[2,3-b:4',3'-f]azepine bis(trifluoroacetate) |
| 49 | 2-fluoro-6-methoxyphenyl | H | 360 | 46 | A | 2 TFA | 2-(2-fluoro-6-methoxyphenyl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 50 | 3-methyl-6-chloro-2-fluorophenyl | H | 378 | 46 | B | Free Base | 2-(6-chloro-2-fluoro-3-methylphenyl)-3,8-dihydroimidazo[4,5-d]dipyrido[2,3-b:4',3'-f]azepine |
| 51 | 2-fluoro-6-(trifluoromethyl)phenyl | H | 398 | 46 | B | Free Base | 2-[2-fluoro-6-(trifluoromethyl)phenyl]-3,8-dihydroimidazo[4,5-d]dipyrido[2,3-b:4',3'-f]azepine |
| 52 | 2-chloro-6-fluoro-3-methylphenyl | H | 378 | 46 | B | Free Base | 2-(2-chloro-6-fluoro-3-methylphenyl)-3,8-dihydroimidazo[4,5-d]dipyrido[2,3-b:4',3'-f]azepine |
| 53 | 3-chloro-2-fluoro-6-(trifluoromethyl)phenyl | H | 432 | 46 | B | Free Base | 2-[3-chloro-2-fluoro-6-(trifluoromethyl)phenyl]-3,8-dihydroimidazo[4,5-d]dipyrido[2,3-b:4',3'-f]azepine |
| 54 | 2-chloro-6-fluorophenyl | H | 364 | 46 | B | Free Base | 2-(2-chloro-6-fluorophenyl)-3,8-dihydroimidazo[4,5-d]dipyrido[2,3-b:4',3'-f]azepine |
| 55 | 2-chloro-5-(trifluoromethyl)phenyl | H | 414 | 46 | B | Free Base | 2-[2-chloro-5-(trifluoromethyl)phenyl]-3,8-dihydroimidazo[4,5-d]dipyrido[2,3-b:4',3'-f]azepine |

TABLE 2-continued

[Structure: core scaffold with W¹—W²—W³—W⁴ and R²ᵃ substituents on dihydroimidazo[4,5-d]dipyrido[2,3-b:4',3'-f]azepine]

| Ex. No. | —W¹—W²—W³—W⁴ | R²ᵃ | MS | Prep Ex | Pur Ex | Salt | Compound Name |
|---|---|---|---|---|---|---|---|
| 56 | 2,6-difluorophenyl | H | 348 | 46 | B | Free Base | 2-(2,6-difluorophenyl)-3,8-dihydroimidazo[4,5-d]dipyrido[2,3-b:4',3'-f]azepine |
| 57 | 2,5-dichlorophenyl | H | 380 | 46 | B | Free Base | 2-(2,5-dichlorophenyl)-3,8-dihydroimidazo[4,5-d]dipyrido[2,3-b:4',3'-f]azepine |
| 58 | 3,5-dibromopyridin-4-yl | H | 469 | 46 | B | Free Base | 2-(3,5-dibromopyridin-4-yl)-3,8-dihydroimidazo[4,5-d]dipyrido[2,3-b:4',3'-f]azepine |
| 59 | 2-bromophenyl | H | 390 | 46 | B | Free Base | 2-(2-bromophenyl)-3,8-dihydroimidazo[4,5-d]dipyrido[2,3-b:4',3'-f]azepine |
| 60 | 2-methylphenyl | H | 326 | 46 | B | Free Base | 2-(2-methylphenyl)-3,8-dihydroimidazo[4,5-d]dipyrido[2,3-b:4',3'-f]azepine |
| 61 | 2-chlorophenyl | H | 346 | 46 | B | Free Base | 2-(2-chlorophenyl)-3,8-dihydroimidazo[4,5-d]dipyrido[2,3-b:4',3'-f]azepine |
| 62 | 2-ethylphenyl | H | 340 | 46 | B | Free Base | 2-(2-ethylphenyl)-3,8-dihydroimidazo[4,5-d]dipyrido[2,3-b:4',3'-f]azepine |

TABLE 2-continued

| Ex. No. | —W$^1$—W$^2$—W$^3$—W$^4$ | R$^{2a}$ | MS | Prep Ex | Pur Ex | Salt | Compound Name |
|---|---|---|---|---|---|---|---|
| 63 | 2,5-dimethylphenyl | H | 340 | 46 | B | Free Base | 2-(2,5-dimethylphenyl)-3,8-dihydroimidazo[4,5-d]dipyrido[2,3-b:4',3'-f]azepine |
| 64 | 2-chloro-3-(trifluoromethyl)phenyl | H | 414 | 46 | B | Free Base | 2-[2-chloro-3-(trifluoromethyl)phenyl]-3,8-dihydroimidazo[4,5-d]dipyrido[2,3-b:4',3'-f]azepine |
| 65 | 2,5-bis(trifluoromethyl)phenyl | H | 448 | 46 | B | Free Base | 2-[2,5-bis(trifluoromethyl)phenyl]-3,8-dihydroimidazo[4,5-d]dipyrido[2,3-b:4',3'-f]azepine |
| 66 | 3-chloro-2,6-difluorophenyl | H | 382 | 46 | B | Free Base | 2-(3-chloro-2,6-difluorophenyl)-3,8-dihydroimidazo[4,5-d]dipyrido[2,3-b:4',3'-f]azepine |
| 67 | 2-(trifluoromethyl)phenyl | H | 380 | 46 | B | Free Base | 2-[2-(trifluoromethyl)phenyl]-3,8-dihydroimidazo[4,5-d]dipyrido[2,3-b:4',3'-f]azepine |
| 68 | 2,3-dichlorophenyl | H | 380 | 46 | B | Free Base | 2-(2,3-dichlorophenyl)-3,8-dihydroimidazo[4,5-d]dipyrido[2,3-b:4',3'-f]azepine |
| 69 | 4-[(2-cyanoethyl)(ethyl)amino]-2-methylphenyl | H | 422 | 46 | B | Free Base | 3-[[4-(3,8-dihydroimidazo[4,5-d]dipyrido[2,3-b:4',3'-f]azepin-2-yl)phenyl](ethyl)amino]propanenitrile |

TABLE 2-continued

| Ex. No. | —W¹—W²—W³—W⁴ | $R^{2a}$ | MS | Prep Ex | Pur Ex | Salt | Compound Name |
|---|---|---|---|---|---|---|---|
| 70 | 2-chloro-3,6-difluorophenyl | H | 382 | 46 | B | Free Base | 2-(2-chloro-3,6-difluorophenyl)-3,8-dihydroimidazo[4,5-d]dipyrido[2,3-b:4',3'-f]azepine |
| 71 | 3-bromopyridin-4-yl | H | 391 | 46 | B | Free Base | 2-(3-bromopyridin-4-yl)-3,8-dihydroimidazo[4,5-d]dipyrido[2,3-b:4',3'-f]azepine |
| 72 | 5-bromo-2,3-dimethoxyphenyl | H | 465 | 46 | B | Free Base | 2-(5-bromo-2,3-dimethoxyphenyl)-3,8-dihydroimidazo[4,5-d]dipyrido[2,3-b:4',3'-f]azepine |
| 73 | 3-chloro-2-fluoro-5-(trifluoromethyl)phenyl | H | 432 | 46 | B | Free Base | 2-[3-chloro-2-fluoro-5-(trifluoromethyl)phenyl]-3,8-dihydroimidazo[4,5-d]dipyrido[2,3-b:4',3'-f]azepine |
| 74 | 3-chloropyridin-4-yl | H | 347 | 46 | B | Free Base | 2-(3-chloropyridin-4-yl)-3,8-dihydroimidazo[4,5-d]dipyrido[2,3-b:4',3'-f]azepine |
| 75 | 2,3-dimethylphenyl | H | 340 | 46 | B | Free Base | 2-(2,3-dimethylphenyl)-3,8-dihydroimidazo[4,5-d]dipyrido[2,3-b:4',3'-f]azepine |
| 76 | 2-fluoro-3-(trifluoromethyl)phenyl | H | 398 | 46 | B | Free Base | 2-[2-fluoro-3-(trifluoromethyl)phenyl]-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 77 | 3-fluoro-2-methylphenyl | H | 344 | 46 | B | Free Base | 2-(3-fluoro-2-methyl phenyl)-3,8-dihydroimidazo[4,5-d]dipyrido[2,3-b:4',3'-f]azepine |
| 78 | 2-fluorophenyl | H | 330 | 46 | B | Free Base | 2-(2-fluorophenyl)-3,8-dihydroimidazo[4,5-d]dipyrido[2,3-b:4',3'-f]azepine |
| 79 | 5-bromo-2-methoxyphenyl | H | 420 | 46 | B | Free Base | 2-(5-bromo-2-methoxyphenyl)-3,8-dihydroimidazo[4,5-d]dipyrido[2,3-b:4',3'-f]azepine |
| 80 | 2-fluoro-5-(trifluoromethyl)phenyl | H | 398 | 46 | B | Free Base | 2-[2-fluoro-5-(trifluoromethyl)phenyl]-3,8-dihydroimidazo[4,5-d]dipyrido[2,3-b:4',3'-f]azepine |
| 81 | 2-fluoro-3-methoxyphenyl | H | 360 | 46 | B | Free Base | 2-(2-fluoro-3-methoxyphenyl)-3,8-dihydroimidazo[4,5-d]dipyrido[2,3-b:4',3'-f]azepine |
| 82 | 2-fluoro-5-methoxyphenyl | H | 360 | 46 | B | Free Base | 2-(2-fluoro-5-methoxyphenyl)-3,8-dihydroimidazo[4,5-d]dipyrido[2,3-b:4',3'-f]azepine |
| 83 | 2,3-difluorophenyl | H | 348 | 46 | B | Free Base | 2-(2,3-difluorophenyl)-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 84 | quinolin-4-yl | H | 363 | 46 | B | Free Base | 2-quinolin-4-yl-3,8-dihydroimidazo[4,5-d]dipyrido[2,3-b:4',3'-f]azepine |
| 85 | 5-fluoro-2-methoxyphenyl | H | 360 | 46 | B | Free Base | 2-(5-fluoro-2-methoxyphenyl)-3,8-dihydroimidazo[4,5-d]dipyrido[2,3-b:4',3'-f]azepine |
| 86 | 5-bromo-2-fluorophenyl | H | 408 | 46 | B | Free Base | 2-(5-bromo-2-fluorophenyl)-3,8-dihydroimidazo[4,5-d]dipyrido[2,3-b:4',3'-f]azepine |
| 87 | 2,5-dimethoxyphenyl | H | 372 | 46 | B | Free Base | 2-(2,5-dimethoxyphenyl)-3,8-dihydroimidazo[4,5-d]dipyrido[2,3-b:4',3'-f]azepine |
| 88 | 2,5-difluorophenyl | H | 348 | 46 | B | Free Base | 2-(2,5-difluorophenyl)-3,8-dihydroimidazo[4,5-d]dipyrido[2,3-b:4',3'-f]azepine |
| 89 | 3,5-dimethyl-1H-pyrrol-2-yl | H | 329 | 46 | B | Free Base | 2-(3,5-dimethyl-1H-pyrrol-2-yl)-3,8-dihydroimidazo[4,5-d]dipyrido[2,3-b:4',3'-f]azepine |
| 90 | 2,6-dimethoxyphenyl | H | 372 | 46 | B | Free Base | 2-(2,6-dimethoxyphenyl)-3,8-dihydroimidazo[4,5-d]dipyrido[2,3-b:4',3'-f]azepine |

TABLE 2-continued

| Ex. No. | —W¹—W²—W³—W⁴ | $R^{2a}$ | MS | Prep Ex | Pur Ex | Salt | Compound Name |
|---|---|---|---|---|---|---|---|
| 91 | (4-methyl-1H-imidazol-5-yl) | H | 316 | 46 | B | Free Base | 2-(4-methyl-1H-imidazol-5-yl)-3,8-dihydroimidazo[4,5-d]dipyrido[2,3-b:4',3'-f]azepine |
| 92 | (4-hydroxy-2,6-dimethoxyphenyl) | H | 388 | 46 | B | Free Base | 4-(3,8-dihydroimidazo[4,5-d]dipyrido[2,3-b:4',3'-f]azepin-2-yl)-3,5-dimethoxyphenol |
| 93 | (pentafluoroethyl) | H | 354 | 46 | B | Free Base | 2-(2-pentafluoroethyl)-3,8-dihydroimidazo[4,5-d]dipyrido[2,3-b:4',3'-f]azepine |
| 94 | (5-bromo-1,3-benzodioxol-4-yl) | H |  | 46 | A | 2 TFA | 2-(5-bromo-1,3-benzodioxol-4-yl)-3,8-dihydroimidazo[4,5-d]dipyrido[2,3-b:4',3'-f]azepine bis(trifluoroacetate) |
| 95 | (4-cyano-2-methyl-2-phenylbutyl) | H | 393 | 46 | A | 2 TFA | 4-(3,8-dihydroimidazo[4,5-d]dipyrido[2,3-b:4',3'-f]azepin-2-yl)-4-phenylpentanenitrile bis(trifluoroacetate) |
| 96 | (2-fluoro-4-trifluoromethylphenyl) | H | 398 | 46 | A | 2 TFA | 2-[2-fluoro-4-(trifluoromethyl)phenyl]-3,8-dihydroimidazo[4,5-d]dipyrido[2,3-b:4',3'-f]azepine bis(trifluoroacetate) |
| 97 | (cyclohexylmethyl) | H | 332 | 46 | A | 2 TFA | 2-(cyclohexylmethyl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ª | MS | Prep Ex | Pur Ex | Salt | Compound Name |
|---|---|---|---|---|---|---|---|
| 98 | H₃CO, OH, Br (substituted phenyl) | H | 436 | 46 | A | 2 TFA | 3-bromo-2-(3,8-dihydroimidazo[4,5-d]dipyrido[2,3-b:4',3'-f]azepin-2-yl)-6-methoxyphenol bis(trifluoroacetate) |
| 99 | 2-fluoropyridin-4-yl | H | 331 | 46 | A | 3 TFA | 2-(2-fluoropyridin-4-yl)-3,8-dihydroimidazo[4,5-d]dipyrido[2,3-b:4',3'-f]azepine tris(trifluoroacetate) |
| 100 | biphenyl-2-yl | H | 388 | 46 | A | 2 TFA | 2-biphenyl-2-yl-3,8-dihydroimidazo[4,5-d]dipyrido[2,3-b:4',3'-f]azepine bis(trifluoroacetate) |
| 101 | 4-(methoxycarbonyl)phenyl | H | 370 | 46 | A | 2 TFA | methyl-4-(3,8-dihydroimidazo[4,5-d]dipyrido[2,3-b:4',3'-f]azepin-2-yl)benzoate bis(trifluoroacetate) |
| 102 | 2-(ethylthio)phenyl | H | 372 | 46 | A | 2 TFA | 2-[2-(ethylthio)phenyl]-3,8-dihydroimidazo[4,5-d]dipyrido[2,3-b:4',3'-f]azepine bis(trifluoroacetate) |
| 103 | 1H-pyrrol-2-yl | H | | 46 | A | 3 TFA | 2-(1H-pyrrol-2-yl)-3,8-dihydroimidazo[4,5-d]dipyrido[2,3-b:4',3'-f]azepine tris(trifluoroacetate) |
| 104 | 4-[(trifluoromethyl)thio]phenyl | H | 412 | 46 | A | 2 TFA | 2-{4-[(trifluoromethyl)thio]phenyl}-3,8-dihydroimidazo[4,5-d]dipyrido[2,3-b:4',3'-f]azepine bis(trifluoroacetate) |
| 105 | 2-naphthyl | H | 362 | 46 | A | 2 TFA | 2-(2-naphthyl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R$^{2a}$ | MS | Prep Ex | Pur Ex | Salt | Compound Name |
|---|---|---|---|---|---|---|---|
| 106 | (tert-butyl carbamate-CH(CH₂Ph)–) | H | 455 | 46 | A | 2 TFA | tert-butyl[1-(3,8-dihydroimidazo[4,5-d]dipyrido[2,3-b:4',3'-f]azepin-2-yl)-2-phenethyl]carbamate bis(trifluoroacetate) |
| 107 | (pyrrolidin-2-yl) | H | 305 | 46 | A | 3 TFA | 2-pyrrolidin-2-yl-3,8-dihydroimidazo[4,5-d]dipyrido[2,3-b:4',3'-f]azepine tris(trifluoroacetate) |
| 108 | (2-chloro-6-methoxyquinolin-3-yl) | H | 427 | 46 | A | 3 TFA | 2-(2-chloro-6-methoxyquinolin-3-yl)-3,8-dihydroimidazo[4,5-d]dipyrido[2,3-b:4',3'-f]azepine tris(trifluoroacetate) |
| 109 | (1-acetylpyrrolidin-2-yl) | H | 347 | 46 | A | 2 TFA | 2-(1-acetylpyrrolidin-2-yl)-3,8-dihydroimidazo[4,5-d]dipyrido[2,3-b:4',3'-f]azepine bis(trifluoroacetate) |
| 110 | (1,3-thiazol-2-yl) | H | 319 | 46 | A | 2 TFA | 2-(1,3-thiazol-2-yl)-3,8-dihydroimidazo[4,5-d]dipyrido[2,3-b:4',3'-f]azepine bis(trifluoroacetate) |
| 111 | (1-acetyl-4-hydroxypyrrolidin-2-yl) | H | 363 | 46 | A | 2 TFA | 1-acetyl-5-(3,8-dihydroimidazo[4,5-d]dipyrido[2,3-b:4',3'-f]azepin-2-yl)pyrrolidin-3-ol bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 112 | (1-acetamidoethyl) | H | 321 | 46 | A | 2 TFA | N-[1-(3,8-dihydroimidazo[4,5-d]dipyrido[2,3-b:4',3'-f]azepin-2-yl)ethyl]acetamide bis(trifluoroacetate) |
| 113 | (N-Boc-4-hydroxypyrrolidin-2-yl) | H | 421 | 46 | A | 2 TFA | tert-butyl 2-(3,8-dihydroimidazo[4,5-d]dipyrido[2,3-b:4',3'-f]azepin-2-yl)-4-hydroxypyrrolidine-1-carboxylate bis(trifluoroacetate) |
| 114 | (4-acetamidophenyl) | H | 369 | 46 | A | 2 TFA | N-[4-(3,8-dihydroimidazo[4,5-d]dipyrido[2,3-b:4',3'-f]azepin-2-yl)phenyl]acetamide bis(trifluoroacetate) |
| 115 | (4-(difluoromethoxy)phenyl) | H | 378 | 46 | A | 2 TFA | 2-[4-(difluoromethoxy)phenyl]-3,8-dihydroimidazo[4,5-d]dipyrido[2,3-b:4',3'-f]azepine bis(trifluoroacetate) |
| 116 | (6-chloropyridin-2-yl) | H | 347 | 46 | A | 3 TFA | 2-(6-chloropyridin-2-yl)-3,8-dihydroimidazo[4,5-d]dipyrido[2,3-b:4',3'-f]azepine tris(trifluoroacetate) |
| 117 | (3-cyano-2-methylthiopyridin-6-yl) | H | 384 | 46 | A | 3 TFA | 6-(3,8-dihydroimidazo[4,5-d]dipyrido[2,3-b:4',3'-f]azepin-2-yl)-2-(methylthio)nicotinonitrile tris(trifluoroacetate) |
| 118 | (3-fluoropyridin-4-yl) | H | 331 | 46 | A | 3 TFA | 2-(3-fluoropyridin-4-yl)-3,8-dihydroimidazo[4,5-d]dipyrido[2,3-b:4',3'-f]azepine tris(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 119 | 6-methoxypyridin-3-yl (H₃CO-pyridine) | H | 343 | 46 | A | 3 TFA | 2-(6-methoxypyridin-3-yl)-3,8-dihydroimidazo[4,5-d]dipyrido[2,3-b:4',3'-f]azepine tris(trifluoroacetate) |
| 120 | 6-bromopyridin-3-yl | H | 391 | 46 | A | 3 TFA | 2-(6-bromopyridin-3-yl)-3,8-dihydroimidazo[4,5-d]dipyrido[2,3-b:4',3'-f]azepine tris(trifluoroacetate) |
| 121 | 6-bromopyridin-2-yl | H | 391 | 46 | A | 3 TFA | 2-(6-bromopyridin-2-yl)-3,8-dihydroimidazo[4,5-d]dipyrido[2,3-b:4',3'-f]azepine tris(trifluoroacetate) |
| 122 | 1H-imidazol-4-yl | H | 302 | 46 | A | 3 TFA | 2-(1H-imidazol-4-yl)-3,8-dihydroimidazo[4,5-d]dipyrido[2,3-b:4',3'-f]azepine tris(trifluoroacetate) |
| 123 | 3-methoxyphenyl | H | 342 | 46 | A | 2 TFA | 2-(3-methoxyphenyl)-3,8-dihydroimidazo[4,5-d]dipyrido[2,3-b:4',3'-f]azepine bis(trifluoroacetate) |
| 124 | 4-methoxyphenyl | H | 342 | 46 | A | 2 TFA | 2-(4-methoxyphenyl)-3,8-dihydroimidazo[4,5-d]dipyrido[2,3-b:4',3'-f]azepine bis(trifluoroacetate) |
| 125 | 2-(methylthio)ethyl | H | 310 | 46 | A | 2 TFA | 2-[2-(methylthio)ethyl]-3,8-dihydroimidazo[4,5-d]dipyrido[2,3-b:4',3'-f]azepine bis(trifluoroacetate) |
| 126 | piperidin-4-yl | H | 319 | 46 | A | 3 TFA | 2-(piperidin-4-yl)-3,8-dihydroimidazo[4,5-d]dipyrido[2,3-b:4',3'-f]azepine tris(trifluoroacetate) |
| 127 | 1-(cyanoacetyl)piperidin-4-yl | H | 386 | 46 | A | 2 TFA | 3-[4-(3,8-dihydroimidazo[4,5-d]dipyrido[2,3-b:4',3'-f]azepin-2-yl)piperidin-1-yl]-3-oxopropanenitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 128 | (3-oxo-3-(piperidin-1-yl)propanenitrile, piperidin-3-yl linkage) | H | 386 | 46 | A | 2 TFA | 3-[3-(3,8-dihydroimidazo[4,5-d]dipyrido[2,3-b:4',3'-f]azepin-2-yl)piperidin-1-yl]-3-oxopropanenitrile bis(trifluoroacetate) |
| 129 | (3-oxo-3-(piperidin-1-yl)propanenitrile, piperidin-4-ylmethyl linkage) | H | 400 | 46 | B | Free Base | 3-(4-((3,8-dihydroimidazo[4,5-d]dipyrido[2,3-b:4',3'-f]azepin-2-yl)methyl)piperidin-1-yl)-3-oxopropanenitrile |
| 130 | (3-oxo-3-(piperidin-1-yl)propanenitrile, piperidin-3-ylmethyl linkage) | H | 400 | 46 | B | Free Base | 3-(3-((3,8-dihydroimidazo[4,5-d]dipyrido[2,3-b:4',3'-f]azepin-2-yl)methyl)piperidin-1-yl)-3-oxopropanenitrile |
| 131 | (1-(trifluoroacetyl)piperidin-4-yl) | H | 415 | 46 | A | 2 TFA | 2-[1-(trifluoroacetyl)piperidin-4-yl] 3,8-dihydroimidazo[4,5-d]dipyrido[2,3-b:4',3'-f]azepine bis(trifluoroacetate) |
| 132 | (1-(trifluoroacetyl)piperidin-3-yl) | H | 415 | 46 | A | 2 TFA | 2-[1-(trifluoroacetyl)piperidin-3-yl] 3,8-dihydroimidazo[4,5-d]dipyrido[2,3-b:4',3'-f]azepine bis(trifluoroacetate) |
| 133 | (1-(trifluoroacetyl)piperidin-4-yl)methyl | H | 429 | 46 | A | 2 TFA | 2-{[1-(trifluoroacetyl)piperidin-4-yl]methyl}-3,8-dihydroimidazo[4,5-d]dipyrido[2,3-b:4',3'-f]azepine bis(trifluoroacetate) |
| 134 | (1-(trifluoroacetyl)piperidin-3-yl)methyl | H | 429 | 46 | A | 2 TFA | 2-{[1-(trifluoroacetyl)piperidin-3-yl]methyl}-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 135 | 1-acetylpiperidin-4-yl | H | 361 | 46 | A | 2 TFA | 2-(1-acetylpiperidin-4-yl)-3,8-dihydroimidazo[4,5-d]dipyrido[2,3-b:4',3'-f]azepine bis(trifluoroaceate) |
| 136 | 1-formylpiperidin-3-yl | H | 347 | 46 | A | 2 TFA | 3-(3,8-dihydroimidazo[4,5-d]dipyrido[2,3-b:4',3'-f]azepin-2-yl)piperidine-1-carbaldehyde bis(trifluoroacetate) |
| 137 | (1-acetylpiperidin-4-yl)methyl | H | 375 | 46 | B | Free Base | 2-[(1-acetylpiperidin-4-yl)methyl]-3,8-dihydroimidazo[4,5-d]dipyrido[2,3-b:4',3'-f]azepine |
| 138 | (1-acetylpiperidin-3-yl)methyl | H | 375 | 46 | A | 2 TFA | 2-[(1-acetylpiperidin-3-yl)methyl]-3,8-dihydroimidazo[4,5-d]dipyrido[2,3-b:4',3'-f]azepine bis(trifluoroacetate) |
| 139 | 1-methylpiperidin-3-yl | H | 333 | 46 | A | 3 TFA | 2-(1-methylpiperidin-3-yl)-3,8-dihydroimidazo[4,5-d]dipyrido[2,3-b:4',3'-f]azepine tris(trifluoroacetate) |
| 140 | 4-cyanophenyl | H | 337 | 46 | B | Free Base | 4-(3,8-dihydroimidazo[4,5-d]dipyrido[2,3-b:4',3'-f]azepin-2-yl)benzonitrile |
| 141 | 4-cyanophenyl | OH | 353 | 46 | B | Free Base | 4-(3-hydroxy-3,8-dihydroimidazo[4,5-d]dipyrido[2,3-b:4',3'-f]azepin-2-yl)benzonitrile |
| 142 | 3-cyanophenyl | H | 337 | 46 | A | 2 TFA | 3-(3,8-dihydroimidazo[4,5-d]dipyrido[2,3-b:4',3'-f]azepin-2-yl)benzonitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 143 | pyridin-3-yl | H | 313 | 46 | B | Free Base | 2-pyridin-3-yl-3,8-dihydroimidazo[4,5-d]dipyrido[2,3-b:4',3'-f]azepine |
| 144 | pyridin-3-yl | OH | 329 | 46 | B | Free Base | 2-pyridin-3-ylimidazo[4,5-d]dipyrido[2,3-b:4',3'-f]azepin-3(8H)-ol |
| 145 | pyridin-2-yl | OH | 329 | 46 | B | Free Base | 2-pyridin-2-ylimidazo[4,5-d]dipyrido[2,3-b:4',3'-f]azepin-3(8H)-ol |
| 146 | pyridin-4-yl | H | 313 | 46 | B | Free Base | 2-pyridin-4-yl-3,8-dihydroimidazo[4,5-d]dipyrido[2,3-b:4',3'-f]azepine |
| 147 | pyridin-4-yl | OH | 329 | 46 | B | Free Base | 2-pyridin-4-ylimidazo[4,5-d]dipyrido[2,3-b:4',3'-f]azepin-3(8H)-ol |
| 148 | piperidin-3-yl | H | 319 | 46 | A | 3 TFA | 2-piperidin-3-yl-3,8-dihydroimidazo[4,5-d]dipyrido[2,3-b:4',3'-f]azepine tris(trifluoroacetate) |
| 149 | 4-(trifluoromethyl)phenyl | H | 380 | 46 | A | 2 TFA | 2-[4-(trifluoromethyl)phenyl]-3,8-dihydroimidazo[4,5-d]dipyrido[2,3-b:4',3'-f]azepine bis(trifluoroacetate) |
| 150 | 6-(trifluoromethyl)pyridin-3-yl | H | 381 | 46 | A | 3 TFA | 2-[6-(trifluoromethyl)pyridin-3-yl]-3,8-dihydroimidazo[4,5-d]dipyrido[2,3-b:4',3'-f]azepine tris(trifluoroacetate) |
| 151 | 3-(trifluoromethyl)phenyl | H | 380 | 46 | A | 2 TFA | 2-[3-(trifluoromethyl)phenyl]-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 152 | 3,5-dimethylisoxazol-4-yl | OH | 347 | 46 | B | Free Base | 2-(3,5-dimethylisoxazol-4-yl)imidazo[4,5-d]dipyrido[2,3-b:4',3'-f]azepin-3(8H)-ol |
| 153 | 4-(methylthio)phenyl | H | 358 | 46 | A | 2 TFA | 2-[4-(methylthio)phenyl]-3,8-dihydroimidazo[4,5-d]dipyrido[2,3-b:4',3'-f]azepine bis(trifluoroacetate) |
| 154 | 4-(methylthio)phenyl | OH | 374 | 46 | B | Free Base | 2-[4-(methylthio)phenyl]imidazo[4,5-d]dipyrido[2,3-b:4',3'-f]azepin-3(8H)-ol |
| 155 | 4-(methylsulfonyl)phenyl | H | 390 | 46 | A | 2 TFA | 2-[4-(methylsulfonyl)phenyl]-3,8-dihydroimidazo[4,5-d]dipyrido[2,3-b:4',3'-f]azepine bis(trifluoroacetate) |
| 156 | 1H-imidazol-2-yl | H | 302 | 46 | A | 3 TFA | 2-(1H-imidazol-2-yl)-3,8-dihydroimidazo[4,5-d]dipyrido[2,3-b:4',3'-f]azepine tris(trifluoroacetate) |
| 157 | 1-methyl-1H-imidazol-2-yl | H | 316 | 46 | A | 3 TFA | 2-(1-methyl-1H-imidazol-2-yl)-3,8-dihydroimidazo[4,5-d]dipyrido[2,3-b:4',3'-f]azepine tris(trifluoroacetate) |
| 158 | phenyl | H | 312 | 46 | A | 2 TFA | 2-phenyl-3,8-dihydroimidazo[4,5-d]dipyrido[2,3-b:4',3'-f]azepine bis(trifluoroacetate) |
| 159 | phenyl | OH | 328 | 46 | A | 2 TFA | 2-phenylimidazo[4,5-d]dipyrido[2,3-b:4',3'-f]azepin-3(8H)-ol bis(trifluoroacetate) |
| 160 | benzyl | H | 326 | 46 | A | 2 TFA | 2-benzyl-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| 161 | benzyl | OH | 342 | 46 | A | 2 TFA | 2-benzylimidazo[4,5-d]dipyrido[2,3-b:4',3'-f]azepin-3(8H)-ol bis(trifluoroacetate) |
| 162 | 2-phenethyl | H | 340 | 46 | A | 2 TFA | 2-(2-phenethyl)-3,8-dihydroimidazo[4,5-d]dipyrido[2,3-b:4',3'-f]azepine bis(trifluoroacetate) |
| 163 | 2-phenethyl | OH | 356 | 46 | A | 2 TFA | 2-(2-phenethyl)imidazo[4,5-d]dipyrido[2,3-b:4',3'-f]azepin-3(8H)-ol bis(trifluoroacetate) |
| 164 | piperidin-4-yl | H | 319 | 46 | A | 3 TFA | 2-piperidin-4-yl-3,8-dihydroimidazo[4,5-d]dipyrido[2,3-b:4',3'-f]azepine tris(trifluoroacetate) |
| 165 | piperidin-4-yl | OH | 335 | 46 | A | 3 TFA | 2-piperidin-4-yl imidazo[4,5-d]dipyrido[2,3-b:4',3'-f]azepin-3(8H)-ol tris(trifluoroacetate) |
| 166 | piperidin-4-ylmethyl | H | 333 | 46 | A | 3 TFA | 2-(piperidin-4-ylmethyl)-3,8-dihydroimidazo[4,5-d]dipyrido[2,3-b:4',3'-f]azepine tris(trifluoroacetate) |
| 167 | piperidin-4-ylmethyl | OH | 349 | 46 | A | 3 TFA | 2-(piperidin-4-ylmethyl)imidazo[4,5-d]dipyrido[2,3-b:4',3'-f]azepin-3(8H)-ol tris(trifluoroacetate) |
| 168 | piperidin-3-ylmethyl | H | 333 | 46 | A | 3 TFA | 2-(piperidin-3-ylmethyl)-3,8-dihydroimidazo[4,5-d]dipyrido[2,3-b:4',3'-f]azepine tris(trifluoroacetate) |
| 169 | tetrahydro-2H-pyran-4-ylmethyl | H | 334 | 46 | A | 2 TFA | 2-(tetrahydro-2H-pyran-4-ylmethyl)-3,8-dihydroimidazo[4,5-d]dipyrido[2,3-b:4',3'-f]azepine bis(trifluoroacetate) |

TABLE 2-continued

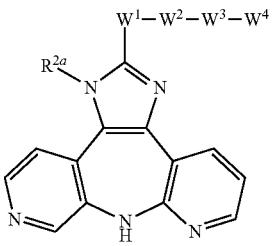

| Ex. No. | —W¹—W²—W³—W⁴ | R²ᵃ | MS | Prep Ex | Pur Ex | Salt | Compound Name |
|---|---|---|---|---|---|---|---|
| 170 | (tetrahydro-2H-pyran-4-ylmethyl) | OH | 350 | 46 | A | 2 TFA | 2-(tetrahydro-2H-pyran-4-ylmethyl)imidazo[4,5-d]dipyrido[2,3-b:4',3'-f]azepin-3(8H)-ol bis(trifluoroacetate) |
| 170a | (tetrahydro-2H-thiopyran-4-ylmethyl) | H | 350 | 46 | A | 2 TFA | 2-(tetrahydro-2H-thiopyran-4-ylmethyl)-3,8-dihydroimidazo[4,5-d]dipyrido[2,3-b:4',3'-f]azepine bis(trifluoroacetate) |
| 170b | (tetrahydro-2H-thiopyran-4-ylmethyl) | OH | 366 | 46 | A | 2 TFA | 2-(tetrahydro-2H-thiopyran-4-ylmethyl)imidazo[4,5-d]dipyrido[2,3-b:4',3'-f]azepin-3(8H)-ol bis(trifluoroacetate) |
| A-9 | 5-methyl-3-(trifluoromethyl)-1H-pyrazol-4-yl | H | 384 | A-9 | A | 2 TFA | 2-[5-methyl-3-(trifluoromethyl)-1H-pyrazol-4-yl]-3,8-dihydroimidazo[4,5-d]dipyrido[2,3-b:4',3'-f]azepine bis(trifluoroacetate) |
| A-10 | 3-(difluoromethyl)-5-methyl-1H-pyrazol-4-yl | H | 366 | A-10 | E | Free Base, 2 HCl | 2-[3-(difluoromethyl)-5-methyl-1H-pyrazol-4-yl]-3,8-dihydroimidazo[4,5-d]dipyrido[2,3-b:4',3'-f]azepine |
| A-11 | 1-(4-methoxybenzyl)-5-methyl-3-(trifluoromethyl)-1H-pyrazol-4-yl | H | 504 | A-9 | C | Free Base | 2-[1-(4-methoxybenzyl)-5-methyl-3-(trifluoromethyl)-1H-pyrazol-4-yl]-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-12 | 1,5-dimethyl-3-(trifluoromethyl)-1H-pyrazol-4-yl | H | 398 | A-9 | C | Free Base | 2-[1,5-dimethyl-3-(trifluoromethyl)-1H-pyrazol-4-yl]-3,8-dihydroimidazo[4,5-d]dipyrido[2,3-b:4',3'-f]azepine |
| A-13 | 1-ethyl-5-methyl-3-(trifluoromethyl)-1H-pyrazol-4-yl | H | 412 | A-9 | C | Free Base | 2-[1-ethyl-5-methyl-3-(trifluoromethyl)-1H-pyrazol-4-yl]-3,8-dihydroimidazo[4,5-d]dipyrido[2,3-b:4',3'-f]azepine |
| A-14 | 1-(cyclopropylmethyl)-5-methyl-3-(trifluoromethyl)-1H-pyrazol-4-yl | H | 438 | A-9 | C | Free Base | 2-[1-(cyclopropylmethyl)-5-methyl-3-(trifluoromethyl)-1H-pyrazol-4-yl]-3,8-dihydroimidazo[4,5-d]dipyrido[2,3-b:4',3'-f]azepine |
| A-15 | 3-methyl-5-(pentafluoroethyl)-1H-pyrazol-4-yl | H | 434 | A-10 | D | 2 HCl | 2-[3-methyl-5-(pentafluoroethyl)-1H-pyrazol-4-yl]-3,8-dihydroimidazo[4,5-d]dipyrido[2,3-b:4',3'-f]azepine dihydrochloride |
| A-16 | 1-(SO₂NMe₂)-5-methyl-3-(trifluoromethyl)-1H-pyrazol-4-yl | H | 491 | A-9 | A | 2 TFA | 4-(3,8-dihydroimidazo[4,5-d]dipyrido[2,3-b:4',3'-f]azepin-2-yl)-N,N,5-trimethyl-3-(trifluoromethyl)-1H-pyrazole-1-sulfonamide bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-17 | (3-[chloro(difluoro)methyl]-5-methyl-1-(tetrahydro-2H-pyran-2-yl)-1H-pyrazol-4-yl) | H | 484 | A-10 | C | Free Base | 2-[3-[chloro(difluoro)methyl]-5-methyl-1-(tetrahydro-2H-pyran-2-yl)-1H-pyrazol-4-yl]-3,8-dihydroimidazo[4,5-d]dipyrido[2,3-b:4',3'-f]azepine |
| A-18 | (3-(difluoromethyl)-5-methyl-1-(tetrahydro-2H-pyran-2-yl)-1H-pyrazol-4-yl) | H | 450 | A-10 | C | Free Base | 2-[3-(difluoromethyl)-5-methyl-1-(tetrahydro-2H-pyran-2-yl)-1H-pyrazol-4-yl]-3,8-dihydroimidazo[4,5-d]dipyrido[2,3-b:4',3'-f]azepine |
| A-19 | (3,5-dimethyl-1H-pyrazol-4-yl) | H | 330 | A-10 | D | Free Base | 2-(3,5-dimethyl-1H-pyrazol-4-yl)-3,8-dihydroimidazo[4,5-d]dipyrido[2,3-b:4',3'-f]azepine |
| A-20 | (3-isobutyl-5-methyl-1H-pyrazol-4-yl) | H | 372 | A-10 | A | 2 TFA | 2-(3-isobutyl-5-methyl-1H-pyrazol-4-yl)-3,8-dihydroimidazo[4,5-d]dipyrido[2,3-b:4',3'-f]azepine bis(trifluoroacetate) |
| A-21 | (3-ethyl-5-methyl-1H-pyrazol-4-yl) | H | 344 | A-10 | A | 2 TFA | 2-(3-ethyl-5-methyl-1H-pyrazol-4-yl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-22 | (3-butyl-5-methyl-1H-pyrazol-4-yl) | H | 372 | A-10 | A | 2-TFA | 2-(3-butyl-5-mehtyl-1H-pyrazol-4-yl)-3,8-dihydroimidazo[4,5-d]dipyrido[2,3-b:4',3'-f]azepine bis(trifluoroacetate) |
| A-23 | (3,5-diethyl-1H-pyrazol-4-yl) | H | 358 | A-10 | A | 2 TFA | 2-(3,5-diethyl-1H-pyrazol-4-yl)-3,8-dihydroimidazo[4,5-d]dipyrido[2,3-b:4',3'-f]azepine bis(trifluoroacetate) |
| A-24 | (5-cyclopropyl-3-methyl-1H-pyrazol-4-yl) | H | 356 | A-10 | A | 2 TFA | 2-(5-cyclopropyl-3-methyl-1H-pyrazol-4-yl)-3,8-dihydroimidazo[4,5-d]dipyrido[2,3-b:4',3'-f]azepine bis(trifluoroacetate) |
| A-25 | (2-chloro-6-methylphenyl) | H | 360 | 46 | A | 2 TFA | 2-(2-chloro-6-methylphenyl)-3,8-dihydroimidazo[4,5-d]dipyrido[2,3-b:4',3'-f]azepine bis(trifluoroacetate) |
| A-26 | (2-cyano-3-methylphenyl) | H | 351 | 46 | A | 2 TFA | 2-(3,8-dihydroimidazo[4,5-d]dipyrido[2,3-b:4',3'-f]azepin-2-yl)-3-methylbenzonitrile bis(trifluoroacetate) |
| A-27 | (2,4-dimethyl-3-thienyl) | H | 346 | 46 | A | 2 TFA | 2-(2,4-dimethyl-3-thienyl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-29 | (4-methylsulfinyl)phenyl | H | 374 | 46 | A | 2 TFA | 2-[4-methylsulfinyl)phenyl]-3,8-dihydroimidazo[4,5-d]dipyrido[2,3-b:4',3'-f]azepine bis(trifluoroacetate) |
| A-30 | 4-(ethylthio)phenyl | H | 372 | 46 | B | Free Base | 2-[4-(ethylthio)phenyl]-3,8-dihydroimidazo[4,5-d]dipyrido[2,3-b:4',3'-f]azepine |
| A-31 | 2-(5-methyl-2-furyl)propyl | H | 358 | 46 | B | Free Base | 2-[2-(5-methyl-2-furyl)propyl]-3,8-dihydroimidazo[4,5-d]dipyrido[2,3-b:4',3'-f]azepine |
| A-32 | 1-benzothien-5-yl | H | 368 | 46 | B | Free Base | 2-(1-benzothien-5-yl)-3,8-dihydroimidazo[4,5-d]dipyrido[2,3-b:4',3'-f]azepine |
| A-33 | 2,4-dimethyl-1,3-thiazol-5-yl | H | 347 | 46 | B | Free Base | 2-(2,4-dimethyl-1,3-thiazol-5-yl)-3,8-dihydroimidazo[4,5-d]dipyrido[2,3-b:4',3'-f]azepine |
| A-33a | 5-methyl-3-phenylisoxazol-4-yl | H | 393 | 46 | B | Free Base | 2-(5-methyl-3-phenylisoxazol-4-yl)-3,8-dihydroimidazo[4,5-d]dipyrido[2,3-b:4',3'-f]azepine |
| A-34 | 4-chloro-1-methyl-1H-pyrazol-3-yl | H | 350 | 46 | B | Free Base | 2-(4-chloro-1-methyl-1H-pyrazol-3-yl)-3,8-dihydroimidazo[4,5-d]dipyrido[2,3-b:4',3'-f]azepine |
| A-35 | 1,3,5-trimethyl-1H-pyrazol-4-yl | H | 344 | 46 | B | Free Base | 2-(1,3,5-trimethyl-1H-pyrazol-4-yl)-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-36 | 5-chloro-1,3-dimethyl-1H-pyrazol-4-yl | H | 364 | 46 | B | Free Base | 2-(5-chloro-1,3-dimethyl-1H-pyrazol-4-yl)-3,8-dihydroimidazo[4,5-d]dipyrido[2,3-b:4',3'-f]azepine |
| A-37 | 3,5-dimethylisoxazol-4-yl | H | 331 | 46 | B | Free Base | 2-(3,5-dimethylisoxazol-4-yl)-3,8-dihydroimidazo[4,5-d]dipyrido[2,3-b:4',3'-f]azepine |
| A-38 | 1-(2-methoxyethyl)-2,5-dimethyl-1H-pyrrol-3-yl | H | 387 | 46 | B | Free Base | 2-[1-(2-methoxyethyl)-2,5-dimethyl-1H-pyrrol-3-yl]-3,8-dihydroimidazo[4,5-d]dipyrido[2,3-b:4',3'-f]azepine |
| A-39 | 1-cyclopropyl-2,5-dimethyl-1H-pyrrol-3-yl | H | 369 | 46 | B | Free Base | 2-(1-cyclopropyl-2,5-dimethyl-1H-pyrrol-3-yl)-3,8-dihydroimidazo[4,5-d]dipyrido[2,3-b:4',3'-f]azepine |
| A-40 | 2,5-dimethoxy-4-(methylthio)phenyl | H | 418 | 46 | B | Free Base | 2-[2,5-dimethoxy-4-(methylthio)phenyl]-3,8-dihydroimidazo[4,5-d]dipyrido[2,3-b:4',3'-f]azepine |
| A-41 | trifluoromethyl | H | 304 | 46 | B | Free Base | 2-(trifluoromethyl)-3,8-dihydroimidazo[4,5-d]dipyrido[2,3-b:4',3'-f]azepine |
| A-42 | 2,4-dimethoxy-3-methylphenyl | H | 386 | 46 | B | Free Base | 2-(2,4-dimethoxy-3-methylphenyl)-3,8-dihydroimidazo[4,5-d]dipyrido[2,3-b:4',3'-f]azepine |

TABLE 2-continued

| Ex. No. | —W¹—W²—W³—W⁴ | $R^{2a}$ | MS | Prep Ex | Pur Ex | Salt | Compound Name |
|---|---|---|---|---|---|---|---|
| A-43 | 2-(methylthio)phenyl | H | 358 | 46 | B | Free Base | 2-[2-(methylthio)phenyl]-3,8-dihydroimidazo[4,5-d]dipyrido[2,3-b:4',3'-f]azepine |
| A-44 | 2-ethoxyphenyl | H | 356 | 46 | B | Free Base | 2-(2-ethoxyphenyl)-3,8-dihydroimidazo[4,5-d]dipyrido[2,3-b:4',3'-f]azepine |
| A-45 | 2,4-dimethoxyphenyl | H | 372 | 46 | B | Free Base | 2-(2,4-dimethoxyphenyl)-3,8-dihydroimidazo[4,5-d]dipyrido[2,3-b:4',3'-f]azepine |
| A-46 | 2,3,4,5,6-pentamethylphenyl | H | 382 | 46 | B | Free Base | 2-(2,3,4,5,6-pentamethylphenyl)-3,8-dihydroimidazo[4,5-d]dipyrido[2,3-b:4',3'-f]azepine |
| A-47 | 2-chloro-4-methoxyphenyl | H | 376 | 46 | B | Free Base | 2-(2-chloro-4-methoxyphenyl)-3,8-dihydroimidazo[4,5-d]dipyrido[2,3-b:4',3'-f]azepine |
| A-48 | 2-methyl-4-methoxyphenyl | H | 356 | 46 | B | Free Base | 2-(2-methyl-4-methoxyphenyl)-3,8-dihydroimidazo[4,5-d]dipyrido[2,3-b:4',3'-f]azepine |
| A-49 | 2-hydroxyphenyl | H | 328 | 46 | B | Free Base | 2-(3,8-dihydroimidazo[4,5-d]dipyrido[2,3-b:4',3'-f]azepin-2-yl)phenol |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-50 | 2,5-dimethyl-4-methoxyphenyl | H | 370 | 46 | B | Free Base | 2-(2,5-dimethyl-4-methoxyphenyl)-3,8-dihydroimidazo[4,5-d]dipyrido[2,3-b:4',3'-f]azepine |
| A-51 | 2-chloro-3,4-dimethoxyphenyl | H | 406 | 46 | B | Free Base | 2-(2-chloro-3,4-dimethoxyphenyl)-3,8-dihydroimidazo[4,5-d]dipyrido[2,3-b:4',3'-f]azepine |
| A-52 | 2,3-dimethyl-4-methoxyphenyl | H | 370 | 46 | B | Free Base | 2-(2,3-dimethyl-4-methoxyphenyl)-3,8-dihydroimidazo[4,5-d]dipyrido[2,3-b:4',3'-f]azepine |
| A-53 | 2,6-dichloro-3,4-dimethoxyphenyl | H | 440 | 46 | B | Free Base | 2-(2,6-dichloro-3,4-dimethoxyphenyl)-3,8-dihydroimidazo[4,5-d]dipyrido[2,3-b:4',3'-f]azepine |
| A-54 | 2,4-dichloro-6-methoxy-3-hydroxyphenyl | H | 426 | 46 | B | Free Base | 2,4-dichloro-3-(3,8-dihydroimidazo[4,5-d]dipyrido[2,3-b:4',3'-f]azepin-2-yl)-6-methoxyphenol |
| A-55 | 2,4,5-trimethylphenyl | H | 354 | 46 | B | Free Base | 2-(2,4,5-trimethylphenyl)-3,8-dihydroimidazo[4,5-d]dipyrido[2,3-b:4',3'-f]azepine |
| A-56 | 2,4-dichlorophenyl | H | 380 | 46 | B | Free Base | 2-(2,4-dichlorophenyl)-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-57 | 4-F, 2-Cl phenyl | H | 364 | 46 | B | Free Base | 2-(2-chloro-4-fluorophenyl)-3,8-dihydroimidazo[4,5-d]dipyrido[2,3-b:4',3'-f]azepine |
| A-58 | 2,4-dimethylphenyl | H | 340 | 46 | B | Free Base | 2-(2,4-dimethyphenyl)-3,8-dihydroimidazo[4,5-d]dipyrido[2,3-b:4',3'-f]azepine |
| A-59 | 2-(OCF₃)phenyl | H | 396 | 46 | B | Free Base | 2-[2-(trifluoromethoxy)phenyl]-3,8-dihydroimidazo[4,5-d]dipyrido[2,3-b:4',3'-f]azepine |
| A-60 | 2-(OCHF₂)phenyl | H | 378 | 46 | B | Free Base | 2-[2-(difluoromethoxy)phenyl]-3,8-dihydroimidazo[4,5-d]dipyrido[2,3-b:4',3'-f]azepine |
| A-61 | 2-methoxypyridin-3-yl | H | 343 | 46 | B | Free Base | 2-(2-methoxypyridin-3-yl)-3,8-dihydroimidazo[4,5-d]dipyrido[2,3-b:4',3'-f]azepine |
| A-62 | 4-F, 2-CF₃ phenyl | H | 398 | 46 | B | Free Base | 2-[4-fluoro-2-(trifluoromethyl)phenyl]-3,8-dihydroimidazo[4,5-d]dipyrido[2,3-b:4',3'-f]azepine |
| A-63 | 2-methoxyphenyl | H | 342 | 46 | B | Free Base | 2-(2-methoxyphenyl)-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-64 | 2,4,6-trimethylphenyl | H | 354 | 46 | B | Free Base | 2-(2,4,6-trimethylphenyl)-3,8-dihydroimidazo[4,5-d]dipyrido[2,3-b:4',3'-f]azepine |
| A-65 | 2-chloro-3-methoxy-6-hydroxyphenyl | H | 392 | 46 | B | Free Base | 2-chloro-3-(3,8-dihydroimidazo[4,5-d]dipyrido[2,3-b:4',3'-f]azepin-2-yl)-6-methoxyphenol |
| A-66 | 3-methylpyridin-2-yl | H | 327 | 46 | B | Free Base | 2-(3-methylpyridin-2-yl)-3,8-dihydroimidazo[4,5-d]dipyrido[2,3-b:4',3'-f]azepine |
| A-67 | 4-(diethylamino)-2-ethoxyphenyl | H | 427 | 46 | B | Free Base | 4-(3,8-dihydroimidazo[4,5-d]dipyrido[2,3-b:4',3'-f]azepin-2-yl)-3-ethoxy-N,N-diethylaniline |
| A-68 | 2,5-dimethoxy-4-bromophenyl | H | 450 | 46 | B | Free Base | 2-(2,5-dimethoxy-4-bromophenyl)-3,8-dihydroimidazo[4,5-d]dipyrido[2,3-b:4',3'-f]azepine |
| A-69 | 2-isobutoxyphenyl | H | 384 | 46 | B | Free Base | 2-(2-isobutoxyphenyl)-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-70 | 3-pyridinyl with 2-NH₂ | H | 328 | 46 | B | Free Base | 3-(3,8-dihydroimidazo[4,5-d]dipyrido[2,3-b:4',3'-f]azepin-2-yl)pyridine-2-amine |
| A-71 | 1H-indol-4-yl | H | 351 | 46 | B | Free Base | 2-(1H-indol-4-yl)-3,8-dihydroimidazo[4,5-d]dipyrido[2,3-b:4',3'-f]azepine |
| A-72 | 2-[(trifluoromethyl)thio]phenyl | H | 412 | 46 | B | Free Base | 2-{2-[(trifluoromethyl)thio]phenyl}-3,8-dihydroimidazo[4,5-d]dipyrido[2,3-b:4',3'-f]azepine |
| A-73 | 4-bromo-3-hydroxyphenyl | H | 406 | 46 | B | Free Base | 4-bromo-3-(3,8-dihydroimidazo[4,5-d]dipyrido[2,3-b:4',3'-f]azepin-2-yl)phenol |
| A-74 | 2-chloro-4-(methylsulfonyl)phenyl | H | 424 | 46 | B | Free Base | 2-[2-chloro-4-(methylsulfonyl)phenyl]-3,8-dihydroimidazo[4,5-d]dipyrido[2,3-b:4',3'-f]azepine |
| A-75 | 2,2-difluoro-1,3-benzodioxol-4-yl | H | 392 | 46 | B | Free Base | 2-(2,2-difluoro-1,3-benzodioxol-4-yl)-3,8-dihydroimidazo[4,5-d]dipyrido[2,3-b:4',3'-f]azepine |
| A-76 | 4-hydroxy-2,6-dimethylphenyl | H | 356 | 46 | B | Free Base | 4-(3,8-dihydroimidazo[4,5-d]dipyrido[2,3-b:4',3'-f]azepin-2-yl)-3,5-dimethyphenol |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-77 | 2-chloro-4,6-dimethoxyphenyl | H | 406 | A-98 | B | Free Base | 2-(2-chloro-4,6-dimethoxyphenyl)-3,8-dihydroimidazo[4,5-d]dipyrido[2,3-b:4',3'-f]azepine |
| A-78 | 3-chlorophenyl | H | 346 | 46 | B | Free Base | 2-(3-chlorophenyl)-3,8-dihydroimidazo[4,5-d]dipyrido[2,3-b:4',3'-f]azepine |
| A-79 | 3-fluoro-5-(trifluoromethyl)phenyl | H | 398 | 46 | B | Free Base | 2-[3-fluoro-5-(trifluoromethyl)phenyl]-3,8-dihydroimidazo[4,5-d]dipyrido[2,3-b:4',3'-f]azepine |
| A-80 | 3,5-dichlorophenyl | H | 380 | 46 | B | Free Base | 2-(3,5-dichlorophenyl)-3,8-dihydroimidazo[4,5-d]dipyrido[2,3-b:4',3'-f]azepine |
| A-81 | 3-chloro-4-methoxyphenyl | H | 376 | 46 | B | Free Base | 2-(3-chloro-4-methoxyphenyl)-3,8-dihydroimidazo[4,5-d]dipyrido[2,3-b:4',3'-f]azepine |
| A-82 | 6-chloro-1,3-benzodioxol-5-yl | H | 390 | 46 | B | Free Base | 2-(6-chloro-1,3-benzodioxol-5-yl)-3,8-dihydroimidazo[4,5-d]dipyrido[2,3-b:4',3'-f]azepine |
| A-83 | 4-chloro-2,6-difluorophenyl | H | 382 | A-98 | B | Free Base | 2-(4-chloro-2,6-difluorophenyl)-3,8-dihydroimidazo[4,5-d]dipyrido[2,3-b:4',3'-f]azepine |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-84 | 2,3-difluoro-6-chlorophenyl | H | 382 | A-98 | B | Free Base | 2-(6-chloro-2,3-difluorophenyl)-3,8-dihydroimidazo[4,5-d]dipyrido[2,3-b:4',3'-f]azepine |
| A-85 | 2,6-dichloro-3-fluorophenyl | H | 398 | A-98 | B | Free Base | 2-(2,6-dichloro-3-fluorophenyl)-3,8-dihydroimidazo[4,5-d]dipyrido[2,3-b:4',3'-f]azepine |
| A-86 | 2-chloro-6-fluoro-3-methoxyphenyl | H | 394 | A-98 | B | Free Base | 2-(2-chloro-6-fluoro-3-methoxyphenyl)-3,8-dihydroimidazo[4,5-d]dipyrido[2,3-b:4',3'-f]azepine |
| A-87 | 2,4,6-trifluorophenyl | H | 366 | 46 | A | 2 TFA | 2-(2,4,6-trifluorophenyl)-3,8-dihydroimidazo[4,5-d]dipyrido[2,3-b:4',3'-f]azepine bis(trifluoroacetate) |
| A-88 | 2-methoxy-4-(trifluoromethoxy)phenyl | H | 426 | 46 | A | 2 TFA | 2-[2-methoxy-4-(trifluoromethoxy)phenyl]-3,58-dihydroimidazo[4,5-d]dipyrido[2,3-b:4',3'-f]azepin bis(trifluoroacetate) |
| A-89 | 3-chloro-4-fluorophenyl | H | 364 | 46 | A | 2 TFA | 2-(3-chloro-4-fluorophenyl)-3,8-dihydroimidazo[4,5-d]dipyrido[2,3-b:4',3'-f]azepine bis(trifluoroacetate) |
| A-90 | 4-fluoro-2-methylphenyl | H | 344 | 46 | A | 2 TFA | 2-(4-fluoro-2-methylphenyl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-91 | 2-methoxy-4-chloro-6-chlorophenyl | H | 410 | A-98 | A | 2 TFA | 2-(2,4-dichloro-6-methoxyphenyl)-3,8-dihydroimidazo[4,5-d]dipyrido[2,3-b:4',3'-f]azepine bis(trifluoroacetate) |
| A-92 | 2,6-dichloro-3-methoxyphenyl | H | 410 | A-98 | A | 2 TFA | 2-(2,6-dichloro-3-methoxyphenyl)-3,8-dihydroimidazo[4,5-d]dipyrido[2,3-b:4'-,3'-f]azepine bis(trifluoroacetate) |
| A-93 | 2,6-dichloro-4-methylthiophenyl | H | 426 | A-98 | A | 2 TFA | 2-(2,6-dichloro-4-methylthiophenyl)-3,8-dihydroimidazo[4,5-d]dipyrido[2,3-b:4',3'-f]azepine bis(trifluoroacetate) |
| A-94 | 2,6-dichloro-4-(methylsulfinyl)phenyl | H | 442 | A-135 | A | 2 TFA | 2-[2,6-dichloro-4-(methylsulfinyl)phenyl]-3,8-dihydroimidazo[4,5-d]dipyrido[2,3-b:4',3'-f]azepine bis(trifluoroacetate) |
| A-95 | 2,6-dichloro-4-(methylsulfonyl)phenyl | H | 458 | A-135 | A | 2 TFA | 2-[2,6-dichloro-4-(methylsulfonyl)phenyl]-3,8-dihydroimidazo[4,5-d]dipyrido[2,3-b:4',3'-f]azepine bis(trifluoroacetate) |
| A-96 | 6-chloro-2-fluoro-3-methoxyphenyl | H | 394 | A-98 | A | 2 TFA | 2-(6-chloro-2-fluoro-3-methoxyphenyl)-3,8-dihydroimidazo[4,5-d]dipyrido[2,3-b:4',3'-f]azepine bis(trifluoroacetate) |

TABLE 2-continued

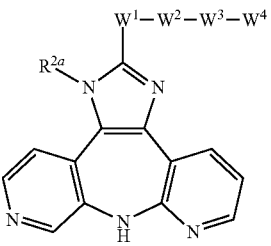

| Ex. No. | —W¹—W²—W³—W⁴ | R²ᵃ | MS | Prep Ex | Pur Ex | Salt | Compound Name |
|---|---|---|---|---|---|---|---|
| A-97 | 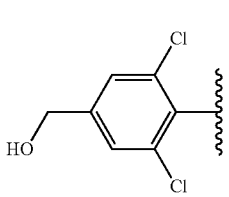 [SMILES: *c1c(Cl)cc(CO)cc1Cl] | H | 394 | A-98 | A | 2 TFA | 2-(2-chloro-6-fluoro-4-methoxyphenyl)-3,8-dihydroimidazo[4,5-d]dipyrido[2,3-b:4',3'-f]azepine bis(trifluoroacetate) |
| A-98 | 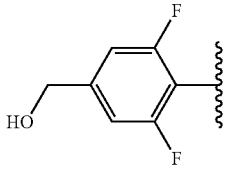 | H | 410 | A-98 | B | Free Base | [3,5-dichloro-4-(3,8-dihydroimidazo[4,5-d]dipyrido[2,3-b:4',3'-f]azepin-2-yl)phenyl]methanol |
| A-99 | 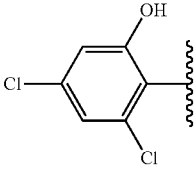 [SMILES: *c1c(O)cc(Cl)cc1Cl] | H | 378 | A-98 | B | Free Base | [3,5-difluoro-4-(3,8-dihydroimidazo[4,5-d]dipyrido[2,3-b:4',3'-f]azepin-2-yl)phenyl]methanol |
| A-100 | 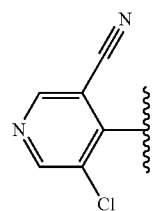 [SMILES: *c1c(Cl)cncc1C#N] | H | 396 | A-98 | B | Free Base | 3,5-dichloro-2-(3,8-dihydroimidazo[4,5-d]dipyrido[2,3-b:4',3'-f]azepin-2-yl)phenol |
| A-101 | 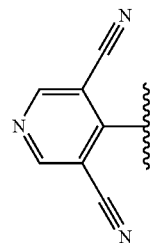 [SMILES: *c1c(C#N)cncc1C#N] | H | 372 | A-101 | A | 3 TFA | 5-chloro-4-(3,8-dihydroimidazo[4,5-d]dipyrido[2,3-b:4',3'-f]azepin-2-yl)nicotinonitrile tris(trifluoroacetate) |
| A-102 |  | H | 363 | A-101 | A | 3 TFA | 4-(3,8-dihydroimidazo[4,5-d]dipyrido[2,3-b:4',3'-f]azepin-2-yl)pyridine-3,5-dicarbonitrile tris(trifluoroacetate) |

TABLE 2-continued

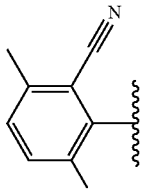

| Ex. No. | —W¹—W²—W³—W⁴ | R²ᵃ | MS | Prep Ex | Pur Ex | Salt | Compound Name |
|---|---|---|---|---|---|---|---|
| A-103 | 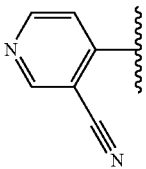 [SMILES: *c1ccncc1C#N] | H | 369 | A-101 | A | 2 TFA | 2-(3,8-dihydroimidazo[4,5-d]dipyrido[2,3-b:4',3'-f]azepin-2-yl)-3-fluoro-6-methylbenzonitrile bis(trifluoroacetate) |
| A-104 | 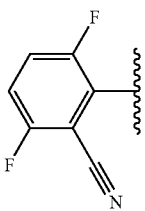 | H | 338 | A-101 | A | 3 TFA | 4-(3,8-dihydroimidazo[4,5-d]dipyrido[2,3-b:4',3'-f]azepin-2-yl)nicotinonitrile tris(trifluoroacetate) |
| A-105 | 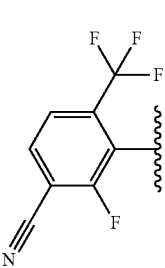 [SMILES: *c1c(C(F)(F)F)ccc(C#N)c1F] | H | 373 | A-101 | A | 2 TFA | 2-(3,8-dihydroimidazo[4,5-d]dipyrido[2,3-b:4',3'-f]azepin-2-yl)-3,6-difluorobenzonitrile bis(trifluoroacetate) |
| A-106 | 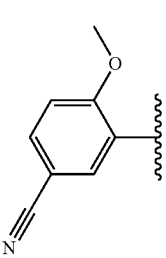 [SMILES: *c1cc(C#N)ccc1OC] | H | 423 | A-101 | A | 2 TFA | 3-(3,8-dihydroimidazo[4,5-d]dipyrido[2,3-b:4',3'-f]azepin-2-yl)-2-fluoro-4-(trifluoromethyl)benzonitrile bis(trifluoroacetate) |
| A-107 | | H | 367 | A-101 | A | 2 TFA | 3-(3,8-dihydroimidazo[4,5-d]dipyrido[2,3-b:4',3'-f]azepin-2-yl)-4-methoxybenzonitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-108 | 2,3-dimethoxy-6-cyanophenyl group | H | 397 | A-101 | A | 2 TFA | 6-(3,8-dihydroimidazo[4,5-d]dipyrido[2,3-b:4',3'-f]azepin-2-yl)-2,3-dimethoxybenzonitrile bis(trifluoroacetate) |
| A-109 | 4,5-dimethoxy-2,6-dicyanophenyl group | H | 422 | A-101 | A | 2 TFA | 2-(3,8-dihydroimidazo[4,5-d]dipyrido[2,3-b:4',3'-f]azepin-2-yl)-4,5-dimethoxyisophthalonitrile bis(trifluoroacetate) |
| A-110 | 4-hydroxy-5-methoxy-2,6-dicyanophenyl group | H | 408 | A-101 | A | 2 TFA | 2-(3,8-dihydroimidazo[4,5-d]dipyrido[2,3-b:4',3'-f]azepin-2-yl)-4-hydroxy-5-methoxyisophthalonitrile bis(trifluoroacetate) |
| A-111 | 2,5-dimethoxy-4-cyanophenyl group | H | 397 | A-101 | A | 2 TFA | 4-(3,8-dihydroimidazo[4,5-d]dipyrido[2,3-b:4',3'-f]azepin-2-yl)-2,5-dimethoxybenzonitrile bis(trifluoroacetate) |
| A-112 | 4-(methylsulfonyl)-2-cyanophenyl group | H | 415 | A-101 | A | 2 TFA | 2-(3,8-dihydroimidazo[4,5-d]dipyrido[2,3-b:4',3'-f]azepin-2-yl)-5-(methylsulfonyl)benzonitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-113 | 3,5-dimethoxy-4-cyanophenyl | H | 397 | A-101 | A | 2 TFA | 2-(3,8-dihydroimidazo[4,5-d]dipyrido[2,3-b:4',3'-f]azepin-2-yl)-3,5-dimethoxybenzonitrile bis(trifluoroacetate) |
| A-114 | 3,5-difluoro-4-cyanophenyl | H | 373 | A-101 | A | 2 TFA | 2-(3,8-dihydroimidazo[4,5-d]dipyrido[2,3-b:4',3'-f]azepin-2-yl)-3,5-difluorobenzonitrile bis(trifluoroacetate) |
| A-115 | 3,4-difluoro-cyanophenyl | H | 373 | A-101 | A | 2 TFA | 2-(3,8-dihydroimidazo[4,5-d]dipyrido[2,3-b:4',3'-f]azepin-2-yl)-3,4-difluorobenzonitrile bis(trifluoroacetate) |
| A-116 | 3-fluoro-6-methoxy-2-cyanophenyl | H | 385 | A-101 | A | 2 TFA | 2-(3,8-dihydroimidazo[4,5-d]dipyrido[2,3-b:4',3'-f]azepin-2-yl)-3-fluoro-6-methoxybenzonitrile bis(trifluoroacetate) |
| A-117 | 4-fluoro-3-cyanophenyl | H | 355 | A-101 | A | 2 TFA | 5-(3,8-dihydroimidazo[4,5-d]dipyrido[2,3-b:4',3'-f]azepin-2-yl)-2-fluorobenzonitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-118 | 2-cyano-3-fluoro-4-methoxyphenyl | H | 385 | A-101 | A | 2 TFA | 2-(3,8-dihydroimidazo[4,5-d]dipyrido[2,3-b:4',3'-f]azepin-2-yl)-3-fluoro-4-methoxybenzonitrile bis(trifluoroacetate) |
| A-119 | 2-cyano-3-fluoro-5-methoxyphenyl | H | 385 | A-101 | A | 2 TFA | 2-(3,8-dihydroimidazo[4,5-d]dipyrido[2,3-b:4',3'-f]azepin-2-yl)-3-fluoro-5-methoxybenzonitrile bis(trifluoroacetate) |
| A-120 | 5-(methylthio)isophthalonitrile-2-yl | H | 408 | A-101 | A | 2 TFA | 2-(3,8-dihydroimidazo[4,5-d]dipyrido[2,3-b:4',3'-f]azepin-2-yl)-5-(methylthio)isophthalonitrile bis(trifluoroacetate) |
| A-121 | 5-(hydroxymethyl)isophthalonitrile-2-yl | H | 392 | A-101 | A | 2 TFA | 2-(3,8-dihydroimidazo[4,5-d]dipyrido[2,3-b:4',3'-f]azepin-2-yl)-5-(hydroxymethyl)isophthalonitrile bis(trifluoroacetate) |
| A-122 | 2-cyano-5-(hydroxymethyl)phenyl | H | 367 | A-101 | A | 2 TFA | 2-(3,8-dihydroimidazo[4,5-d]dipyrido[2,3-b:4',3'-f]azepin-2-yl)-5-(hydroxymethyl)benzonitrile bis(trifluoroacetate) |

TABLE 2-continued

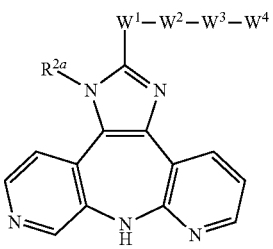

| Ex. No. | —W¹—W²—W³—W⁴ | R²ᵃ | MS | Prep Ex | Pur Ex | Salt | Compound Name |
|---|---|---|---|---|---|---|---|
| A-123 | 3,5-dichloro-4-(cyanomethyl)phenyl | H | 419 | A-123 | B | Free Base | [3,5-dichloro-4-(3,8-dihydroimidazo[4,5-d]dipyrido[2,3-b:4',3'-f]azepin-2-yl)phenyl]acetonitrile |
| A-124 | 3,5-dicyano-4-(cyanomethyl)phenyl | H | 401 | A-101 | A | 2 TFA | 5-(cyanomethyl)-2-(3,8-dihydroimidazo[4,5-d]dipyrido[2,3-b:4',3'-f]azepin-2-yl)isophthalonitrile bis(trifluoroacetate) |
| A-125 | 3-cyano-4-(cyanomethyl)phenyl | H | 376 | A-101 | A | 2 TFA | 5-(cyanomethyl)-2-(3,8-dihydroimidazo[4,5-d]dipyrido[2,3-b:4',3'-f]azepin-2-yl)benzonitrile bis(trifluoroacetate) |
| A-126 | 2-cyano-4-(methylsulfinyl)phenyl | H | 399 | A-101 | A | 2 TFA | 2-(3,8-dihydroimidazo[4,5-d]dipyrido[2,3-b:4',3'-f]azepin-2-yl)-5-(methylsulfinyl)benzonitrile bis(trifluoroacetate) |
| A-127 | 2,6-dicyano-4-(methylsulfonyl)phenyl | H | 440 | A-101 | A | 2 TFA | 2-(3,8-dihydroimidazo[4,5-d]dipyrido[2,3-b:4',3'-f]azepin-2-yl)5-(methylsulfonyl)isophthalonitrile bis(trifluoroacetate) |
| A-128 | 2-cyano-4-hydroxyphenyl | H | 353 | A-101 | B | Free Base | 2-(3,8-dihydroimidazo[4,5-d]dipyrido[2,3-b:4',3'-f]azepin-2-yl)-5-hydroxybenzonitrile |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-129 | 3,5-dichloro-4-((dimethylamino)methyl)phenyl | H | 437 | A-129 | B | Free Base | 1-[3,5-dichloro-4-(3,8-dihydroimidazo[4,5-d]dipyrido[2,3-b:4',3'-f]azepin-2-yl)phenyl]-N,N-dimethylmethanamine |
| A-130 | 2,6-dichloro-4-(morpholin-4-ylmethyl)phenyl | H | 479 | A-129 | B | Free Base | 2-[2,6-dichloro-4-(morpholin-4-ylmethyl)phenyl]-3,8-dihydroimidazo[4,5-d]dipyrido[2,3-b:4',3'-f]azepine |
| A-131 | 2,6-dichloro-4-(thiomorpholin-4-ylmethyl)phenyl | H | 495 | A-129 | A | 3 TFA | 2-[2,6-dichloro-4-(thiomorpholin-4-ylmethyl)phenyl]-3,8-dihydroimidazo[4,5-d]dipyrido[2,3-b:4',3'-f]azepine tris(trifluoroacetate) |
| A-132 | 2,6-dichloro-4-(methoxymethyl)phenyl | H | 424 | A-146 | B | Free Base | 2-[2,6-dichloro-4-(methoxymethyl)phenyl]-3,8-dihydroimidazo[4,5-d]dipyrido[2,3-b:4',3'-f]azepine |
| A-133 | 2,6-dichloro-4-(ethylthio)phenyl | H | 440 | A-133 | A | 2 TFA | 2-[2,6-dichloro-4-(ethylthio)phenyl]-3,8-dihydroimidazo[4,5-d]dipyrido[2,3-b:4',3'-f]azepine bis(trifluoroacetate) |
| A-134 | 2,6-dichloro-4-(isopropylthio)phenyl | H | 454 | A-98 | A | 2 TFA | 2-[2,6-dichloro-4-(isopropylthio)phenyl]-3,8-dihydroimidazo[4,5-d]dipyrido[2,3-b:4',3'-f]azepine bis(trifluoroacetate) |
| A-135 | 2,6-dichloro-4-(ethylsulfinyl)phenyl | H | 456 | A-135 | A | 2 TFA | 2-[2,6-dichloro-4-(ethylsulfinyl)phenyl]-3,8-dihydroimidazo[4,5-d]dipyrido[2,3-b:4',3'-f]azepine bis(trifluoroacetate) |

TABLE 2-continued

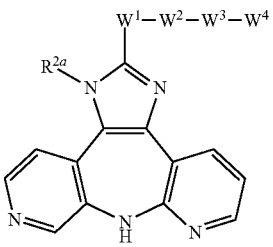

| Ex. No. | —W¹—W²—W³—W⁴ | R²ᵃ | MS | Prep Ex | Pur Ex | Salt | Compound Name |
|---|---|---|---|---|---|---|---|
| A-136 | (2,6-dichloro-4-(ethylsulfonyl)phenyl) | H | 472 | A-136 | A | 2 TFA | 2-[2,6-dichloro-4-(ethylsulfonyl)phenyl]-3,8-dihydroimidazo[4,5-d]dipyrido[2,3-b:4',3'-f]azepine bis(trifluoroacetate) |
| A-137 | (2,6-dichloro-4-(isopropylsulfinyl)phenyl) | H | 470 | A-135 | A | 2 TFA | 2-[2,6-dichloro-4-(isopropylsulfinyl)phenyl]-3,8-dihydroimidazo[4,5-d]dipyrido[2,3-b:4',3'-f]azepine bis(trifluoroacetate) |
| A-138 | (2,6-dichloro-4-(isopropylsulfonyl)phenyl) | H | 486 | A-135 | A | 2 TFA | 2-[2,6-dichloro-4-(isopropylsulfonyl)phenyl]-3,8-dihydroimidazo[4,5-d]dipyrido[2,3-b:4',3'-f]azepine bis(trifluoroacetate) |
| A-139 | (isopropylsulfonyl)benzonitrile | H | 443 | A-101 | A | 2 TFA | 2-(3,8-dihydroimidazo[4,5-d]dipyrido[2,3-b:4',3'-f]azepin-2-yl)-5-(isopropylsulfonyl)benzo-nitrile bis(trifluoroacetate) |
| A-140 | (ethylthio)isophthalonitrile | H | 422 | A-101 | A | 2 TFA | 2-(3,8-dihydroimidazo[4,5-d]dipyrido[2,3-b:4',3'-f]azepin-2-yl)-5-(ethylthio)isophthalo-nitrile bis(trifluoroacetate) |
| A-141 | 3-chloro-5-(ethylthio)benzonitrile | H | 431 | A-101 | A | 2 TFA | 3-chloro-2-(3,8-dihydroimidazo[4,5-d]dipyrido[2,3-b:4',3'-f]azepin-2-yl)-5-(ethylthio)benzonitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-142 | (4-isopropylthio-2,6-dicyanophenyl) | H | 436 | A-101 | A | 2 TFA | 2-(3,8-dihydroimidazo[4,5-d]dipyrido[2,3-b:4',3'-f]azepin-2-yl)-5-(isopropylthio)isophthalonitrile bis(trifluoroacetate) |
| A-143 | (4-isopropylthio-2-cyano-6-chlorophenyl) | H | 445 | A-101 | A | 2 TFA | 3-chloro-2-(3,8-dihydroimidazo[4,5-d]dipyrido[2,3-b:4',3'-f]azepin-2-yl)-5-(isopropylthio)benzonitrile bis(trifluoroacetate) |
| A-144 | (4-isopropylsulfinyl-2,6-dicyanophenyl) | H | 452 | A-101 | A | 2 TFA | 2-(3,8-dihydroimidazo[4,5-d]dipyrido[2,3-b:4',3'-f]azepin-2-yl)-5-(isopropylsulfinyl)isophthalonitrile bis(trifluoroacetate) |
| A-145 | (4-isopropylsulfinyl-2-cyano-6-chlorophenyl) | H | 461 | A-101 | A | 2 TFA | 3-chloro-2-(3,8-dihydroimidazo[4,5-d]dipyrido[2,3-b:4',3'-f]azepin-2-yl)-5-(isopropylsulfinyl)benzonitrile bis(trifluoroacetate) |
| A-146 | (2,6-dichloro-4-(cyanomethoxy)phenyl) | H | 435 | A-146 | A | 2 TFA | 2-[3,5-dichloro-4-(3,8-dihydroimidazo[4,5-d]dipyrido[2,3-b:4',3'-f]azepin-2-yl)phenoxy]acetonitrile bis(trifluoroacetate) |
| A-147 | (2,6-dichloro-4-(1-cyanoethoxy)phenyl) | H | 449 | A-146 | A | 2 TFA | 2-[3,5-dichloro-4-(3,8-dihydroimidazo[4,5-d]dipyrido[2,3-b:4',3'-f]azepin-2-yl)phenoxy]propanenitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-148 | | H | 431 | A-101 | A | 2 TFA | 5-(1-cyanoethoxy)-2-(3,8-dihydroimidazo[4,5-d]dipyrido[2,3-b:4',3'-f]azepin-2-yl)isophthalonitrile bis(trifluoroacetate) |
| A-149 | | H | 406 | A-101 | A | 2 TFA | 5-(1-cyanoethoxy)-2-(3,8-dihydroimidazo[4,5-d]dipyrido[2,3-b:4',3'-f]azepin-2-yl)benzonitrile bis(trifluoroacetate) |
| A-150 | | H | 417 | A-101 | A | 2 TFA | 5-(cyanomethoxy)-2-(3,8-dihydroimidazo[4,5-d]dipyrido[2,3-b:4',3'-f]azepin-2-yl)isophthalonitrile bis(trifluoroacetate) |
| A-151 | | H | 467 | A-146 | A | 2 TFA | 2-[3,5-dichloro-4-(3,8-dihydroimidazo[4,5-d]dipyrido[2,3-b:4',3'-f]azepin-2-yl)phenoxy]propanamide bis(trifluoroacetate) |
| A-152 | | H | 449 | A-101 | A | 2 TFA | 2-[3,5-dicyano-4-(3,8-dihydroimidazo[4,5-d]dipyrido[2,3-b:4',3'-f]azepin-2-yl)phenoxy]propanamide bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-153 | | H | 467 | A-101 | A | 2 TFA | 5-(2-amino-1-methyl-2-oxoethoxy)-3-cyano-2-(3,8-dihydroimidazo[4,5-d]dipyrido[2,3-b:4',3'-f]azepin-2-yl)benzamide bis(trifluoroacetate) |
| A-154 | | H | 485 | A-101 | A | 2 TFA | 5-(2-amino-1-methyl-2-oxoehtoxy)-2-(3,8-dihydroimidazo[4,5-d]dipyrido[2,3-b:4',3'-f]azepin-2-yl)isophthalamide bis(trifluoroacetate) |
| A-155 | | H | 453 | A-146 | A | 2 TFA | 2-[3,5-dichloro-4-(3,8-dihydroimidazo[4,5-d]dipyrido[2,3-b:4',3'-f]azepin-2-yl)phenoxy]acetamide bis(trifluoroacetate) |
| A-156 | | H | 435 | A-101 | A | 2 TFA | 2-[3,5-dicyano-4-(3,8-dihydroimidazo[4,5-d]dipyrido[2,3-b:4',3'-f]azepin-2-yl)phenoxy]acetamide bis(trifluoroacetate) |
| A-157 | | H | 506 | A-146 | A | 2 TFA | 2-cyano-2-[3,5-dichloro-4-(3,8-dihydroimidazo[4,5-d]dipyrido[2,3-b:4',3'-f]azepin-2-yl)phenoxy]-N,N-dimethylacetamide bis(trifluoroacetate) |

TABLE 2-continued

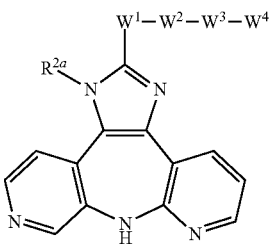

| Ex. No. | —W¹—W²—W³—W⁴ | R²ᵃ | MS | Prep Ex | Pur Ex | Salt | Compound Name |
|---|---|---|---|---|---|---|---|
| A-158 | 2,6-dicyanophenyl | H | 362 | A-158 | A, D | 2 TFA, 2 HCl | 2-(3,8-dihydroimidazo[4,5-d]dipyrido[2,3-b:4',3'-f]azepin-2-yl)isopthalonitrile |
| A-159 | 2-cyanophenyl | H | 337 | A-101 | A | 2 TFA | 2-(3,8-dihydroimidazo[4,5-d]dipyrido[2,3-b:4',3'-f]azepin-2-yl)benzonitrile bis(trifluoroacetate) |
| A-160 | 2-cyano-5-hydroxyphenyl | H | 353 | A-101 | A | 2 TFA | 2-(3,8-dihydroimidazo[4,5-d]dipyrido[2,3-b:4',3'-f]azepin-2-yl)-4-hydroxybenzonitrile bis(trifluoroacetate) |
| A-161 | 4-cyano-1,3-benzodioxol-5-yl | H | 381 | A-101 | A | 2 TFA | 4-(3,8-dihydroimidazo[4,5-d]dipyrido[2,3-b:4',3'-f]azepin-2-yl)-1,3-benzodioxole-5-carbonitrile bis(trifluoroacetate) |
| A-162 | 2-cyano-6-chlorophenyl | H | 371 | A-162 | A, D | 2 TFA, 2 HCl | 3-chloro-2-(3,8-dihydroimidazo[4,5-d]dipyrido[2,3-b:4',3'-f]azepin-2-yl)benzonitrile |
| A-163 | 2-cyano-6-fluoro-5-methylphenyl | H | 369 | A-101 | A | 2 TFA | 3-fluoro-4-methyl-2-(3,8-dihydroimidazo[4,5-d]dipyrido[2,3-b:4',3'-f]azepin-2-yl)benzonitrile bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-164 | 2-cyano-3-fluorophenyl | H | 355 | A-101 | A | 2 TFA | 3-fluoro-2-(3,8-dihydroimidazo[4,5-d]dipyrido[2,3-b:4',3'-f]azepin-2-yl)benzonitrile bis(trifluoroacetate) |
| A-165 | 2-cyano-3-methoxyphenyl | H | 367 | A-101 | A | 2 TFA | 3-methoxy-2-(3,8-dihydroimidazo[4,5-d]dipyrido[2,3-b:4',3'-f]azepin-2-yl)benzonitrile bis(trifluoroacetate) |
| A-166 | 2-cyano-4-fluorophenyl | H | 355 | A-101 | A | 2 TFA | 5-fluoro-2-(3,8-dihydroimidazo[4,5-d]dipyrido[2,3-b:4',3'-f]azepin-2-yl)benzonitrile bis(trifluoroacetate) |
| A-167 | 3-chloro-6-methoxy-2-cyanophenyl | H | 401 | A-101 | A | 2 TFA | 3-chloro-6-methoxy-2-(3,8-dihydroimidazo[4,5-d]dipyrido[2,3-b:4',3'-f]azepin-2-yl)benzonitrile bis(trifluoroacetate) |
| A-168 | 2,6-dicyano-3-methoxyphenyl | H | 392 | A-101 | A | 2 TFA | 2-(3,8-dihydroimidazo[4,5-d]dipyrido[2,3-b:4',3'-f]azepin-2-yl)-4-methoxyisophthalonitrile bis(trifluoroacetate) |
| A-169 | 3-(Boc-amino)pyridin-4-yl | H | 428 | 46 | A | 3 TFA | tert-butyl [4-(3,8-dihydroimidazo[4,5-d]dipyrido[2,3-b:4',3'-f]azepin-2-yl)pyridin-3-yl]carbamate tris(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-170 | (tert-butyl carbamate pyridin-3-yl with methyl) | OH | 444 | A-170 | A | 3 TFA | tert-butyl [4-(3-hydroxy-3,8-dihydroimidazo[4,5-d]dipyrido[2,3-b:4',3'-f]azepin-2-yl)pyridin-2-yl]carbamate tris(trifluoroacetate) |
| A-171 | 3,5-dimethylpyridin-4-yl | H | 341 | A-171 | B | Free Base | 2-(3,5-dimethylpyridin-4-yl)-3,8-dihydroimidazo[4,5-d]dipyrido[2,3-b:4',3'-f]azepine |
| A-172 | 3,5-dichloro-4-hydroxyphenyl | H | 396 | A-172 | A | 2 TFA | 3,5-dichloro-4-(3,8-dihydroimidazo[4,5-d]dipyrido[2,3-b:4',3'-f]azepin-2-yl)phenol bis(trifluoroacetate) |
| A-173 | 2,6-dichloro-4-methoxyphenyl | H | 410 | A-173 | A | 2 TFA | 2-(2,6-dichloro-4-methoxyphenyl)-3,8-dihydroimidazo[4,5-d]dipyrido[2,3-b:4',3'-f]azepine bis(trifluoroacetate) |
| A-174 | 2,6-dichloro-4-ethoxyphenyl | H | 424 | A-173 | B | Free Base | 2-(2,6-dichloro-4-ethoxyphenyl)-3,8-dihydroimidazo[4,5-d]dipyrido[2,3-b:4',3'-f]azepine |
| A-175 | 2,6-dichloro-4-isopropoxyphenyl | H | 438 | A-175 | A | 2 TFA | 2-(2,6-dichloro-4-isopropoxyphenyl)-3,8-dihydroimidazo[4,5-d]dipyrido[2,3-b:4',3'-f]azepine bis(trifluoroacetate) |

TABLE 2-continued

| Ex. No. | —W¹—W²—W³—W⁴ | R²ᵃ | MS | Prep Ex | Pur Ex | Salt | Compound Name |
|---|---|---|---|---|---|---|---|
| A-176 | 2,6-dichloro-4-(trifluoromethoxy)phenyl | H | 464 | A-176 | A | 2 TFA | 2-[2,6-dichloro-4-(trifluoromethoxy)phenyl]-3,8-dihydroimidazo[4,5-d]dipyrido[2,3-b:4',3'-f]azepine bis(trifluoroacetate) |
| A-177 | 3-methylpyridin-4-yl | H | 327 | 46 | A | 3 TFA | 2-(3-methylpyridin-4-yl)-3,8-dihydroimidazo[4,5-d]dipyrido[2,3-b:4',3'-f]azepine tris(trifluoroacetate) |
| A-178 | 2-methylpyridin-3-yl | H | 327 | 46 | A | 3 TFA | 2-(2-methylpyridin-3-yl)-3,8-dihydroimidazo[4,5-d]dipyrido[2,3-b:4',3'-f]azepine tris(trifluoroacetate) |
| A-179 | 2,4-dimethylpyridin-3-yl | H | 341 | 46 | A | 3 TFA | 2-(2,4-dimethylpyridin-3-yl)-3,8-dihydroimidazo[4,5-d]dipyrido[2,3-b:4',3'-f]azepine tris(trifluoroacetate) |
| A-180 | 5-chloro-2-ethoxyphenyl | H | 390 | 46 | A | 2 TFA | 2-(5-chloro-2-ethoxyphenyl)-3,8-dihydroimidazo[4,5-d]dipyrido[2,3-b:4',3'-f]azepine bis(trifluoroacetate) |
| A-181 | 5-chloro-2-methoxyphenyl | H | 376 | 46 | A | 2 TFA | 2-(5-chloro-2-methoxyphenyl)-3,8-dihydroimidazo[4,5-d]dipyrido[2,3-b:4',3'-f]azepine bis(trifluoroacetate) |
| A-182 | 5-bromo-2-ethoxyphenyl | H | 434 | 46 | A | 2 TFA | 2-(5-bromo-2-ethoxyphenyl)-3,8-dihydroimidazo[4,5-d]dipyrido[2,3-b:4',3'-f]azepine bis(trifluoroacetate) |

TABLE 2-continued

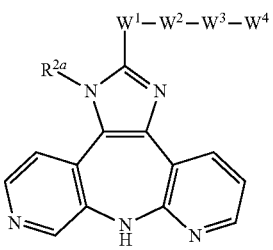

| Ex. No. | —W¹—W²—W³—W⁴ | R²ᵃ | MS | Prep Ex | Pur Ex | Salt | Compound Name |
|---|---|---|---|---|---|---|---|
| A-183 | 2,3-difluoro-6-methoxyphenyl | H | 378 | 46 | A | 2 TFA | 2-(2,3-difluoro-6-methoxyphenyl)-3,8-dihydroimidazo[4,5-d]dipyrido[2,3-b:4',3'-f]azepine bis(trifluoroacetate) |
| A-184 | 2,6-dichloro-4-(trifluoromethyl)phenyl | H | 448 | 46 | A | 2 TFA | 2-[2,6-dichloro-4-(trifluoromethyl)phenyl]-3,8-dihydroimidazo[4,5-d]dipyrido[2,3-b:4',3'-f]azepine bis(trifluoroacetate) |
| A-185 | 3,5-dichloro-4-(N,N-dimethylamino)phenyl | H | 423 | 46 | A | 3 TFA | 3,5-dichloro-4-(3,8-dihydroimidazo[4,5-d]dipyrido[2,3-b:4',3'-f]azepin-2-yl)-N,N-dimethylaniline tris(trifluoroacetate) |
| A-186 | 2,6-dichloro-4-fluorophenyl | H | 398 | 46 | A | 2 TFA | 2-(2,6-dichloro-4-fluorophenyl)-3,8-dihydroimidazo[4,5-d]dipyrido[2,3-b:4',3'-f]azepine bis(trifluoroacetate) |
| A-187 | 3-chloro-5-methoxy-2-cyanophenyl | H | 401 | A-188 | B | Free Base | 3-chloro-2-(3,8-dihydroimidazo[4,5-d]dipyrido[2,3-b:4',3'-f]azepin-2-yl)-5-methoxybenzonitrile |
| A-188 | 5-methoxy-2,6-dicyanophenyl | H | 392 | A-188 | B | Free Base | 2-(3,8-dihydroimidazo[4,5-d]dipyrido[2,3-b:4',3'-f]azepin-2-yl)-5-methoxyisophthalonitrile |

TABLE 2-continued

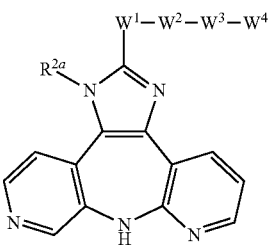

| Ex. No. | —W¹—W²—W³—W⁴ | R²ᵃ | MS | Prep Ex | Pur Ex | Salt | Compound Name |
|---|---|---|---|---|---|---|---|
| A-189 | 3-chloro-5-ethoxy-2-methylbenzonitrile group | H | 415 | A-188 | B | Free Base | 3-chloro-2-(3,8-dihydroimidazo[4,5-d]dipyrido[2,3-b:4',3'-f]azepin-2-yl)-5-ethoxybenzonitrile |
| A-190 | 5-ethoxyisophthalonitrile group | H | 406 | A-188 | B | Free Base | 2-(3,8-dihydroimidazo[4,5-d]dipyrido[2,3-b:4',3'-f]azepin-2-yl)-5-ethoxyisophthalonitrile |
| A-191 | 3-chloro-5-isopropoxybenzonitrile group | H | 429 | A-188 | B | Free Base | 3-chloro-2-(3,8-dihydroimidazo[4,5-d]dipyrido[2,3-b:4',3'-f]azepin-2-yl)-5-isopropoxybenzonitrile |
| A-192 | 5-isopropoxyisophthalonitrile group | H | 420 | A-192 | E | Free Base | 2-(3,8-dihydroimidazo[4,5-d]dipyrido[2,3-b:4',3'-f]azepin-2-yl)-5-isopropoxyisophthalonitrile |
| A-193 | 5-(trifluoromethoxy)isophthalonitrile group | H | 446 | A-188 | A | 2 TFA | 2-(3,8-dihydroimidazo[4,5-d]dipyrido[2,3-b:4',3'-f]azepin-2-yl)-5-(trifluoromethoxy)isophthalonitrile bis(trifluoroacetate) |

TABLE 2-continued

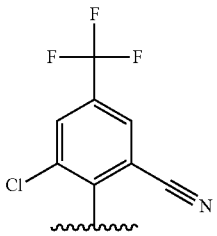 [SMILES: *c1c(Cl)cc(C(F)(F)F)cc1C#N]

| Ex. No. | —W¹—W²—W³—W⁴ | R²ᵃ | MS | Prep Ex | Pur Ex | Salt | Compound Name |
|---|---|---|---|---|---|---|---|
| A-194 | 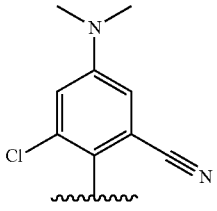 [SMILES: *c1c(Cl)cc(N(C)C)cc1C#N] | H | 439 | A-188 | B | Free Base | 3-chloro-2-(3,8-dihydroimidazo[4,5-d]dipyrido[2,3-b:4',3'-f]azepin-2-yl)-5-(trifluoromethyl)benzonitrile |
| A-195 | 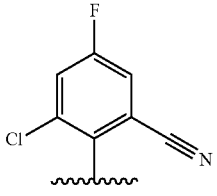 [SMILES: *c1c(Cl)cc(F)cc1C#N] | H | 414 | A-188 | A | 3 TFA | 3-chloro-2-(3,8-dihydroimidazo[4,5-d]dipyrido[2,3-b:4',3'-f]azepin-2-yl)-5-(dimethylamino)benzonitrile tris(trifluoroacetate) |
| A-196 | 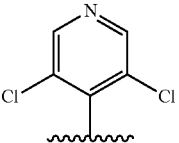 [SMILES: *c1c(Cl)cncc1Cl] | H | 389 | A-188 | A | 2 TFA | 3-chloro-2-(3,8-dihydroimidazo[4,5-d]dipyrido[2,3-b:4',3'-f]azepin-2-yl)-5-fluorobenzonitrile bis(trifluoroacetate) |

TABLE 3

| Ex. No. | —W¹—W²—W³—W⁴ | R²ᵃ | MS (M + H) | Prep. Ex. | Pur. Meth. | Salt | Compound Name |
|---|---|---|---|---|---|---|---|
| 171 | | H | 381 | 171 | B | Free Base | 2-(3,5-dichloropyridin-4-yl)-3,8-dihydroimidazo[4,5-d]dipyrido[2,3-b:3',4'-f]azepine |

TABLE 3-continued

| Ex. No. | —W¹—W²—W³—W⁴ | $R^{2a}$ | MS (M + H) | Prep. Ex. | Pur. Meth. | Salt | Compound Name |
|---|---|---|---|---|---|---|---|
| 172 | 2,6-dichlorophenyl | H | 380 | 171 | B | Free Base | 2-(2,6-dichlorophenyl)-3,8-dihydroimidazo[4,5-d]dipyrido[2,3-b:3',4'-f]azepine |
| 173 | 2,6-difluorophenyl | H | 348 | 171 | A | 2 TFA | 2-(2,6-difluorophenyl)-3,8-dihydroimidazo[4,5-d]dipyrido[2,3-b:3',4'-f]azepine-bis(trifluoroacetate) |
| 174 | 2-chloro-6-fluorophenyl | H | 364 | 171 | B | Free Base | 2-(2-chloro-6-fluorophenyl)-3,8-dihydroimidazo[4,5-d]dipyrido[2,3-b:3',4'-f]azepine |
| 175 | 2,6-dimethylphenyl | H | 340 | 171 | B | Free Base | 2-(2,6-dimethylphenyl)-3,8-dihydroimidazo[4,5-d]dipyrido[2,3-b:3',4'-f]azepine |
| 176 | 3,3-diethyl-4-cyanobutyl | H | 359 | 171 | A | 2 TFA | 4-(3,8-dihydroimidazo[4,5-d]dipyrido[2,3-b:3',4'-f]azepin-2-yl)-4-ethylhexanenitrile-bis(trifluoroacetate) |
| 177 | 1-(4-methoxybenzyl)-5-methyl-3-(trifluoromethyl)-1H-pyrazol-4-yl | OH | 520 | 171 | C | Free Base | 2-[1-(4-methoxybenzyl)-5-methyl-3-(trifluoromethyl)-1H-pyrazol-4-yl]imidazo[4,5-d]dipyrido[2,3-b:3',4'-f]azepin-3(8H)-ol |
| 178 | 1-(4-methoxybenzyl)-5-methyl-3-(trifluoromethyl)-1H-pyrazol-4-yl | H | 504 | 171 | A | 2 TFA | 2-[1-(4-methoxybenzyl)-5-methyl-3-(trifluoromethyl)-1H-pyrazol-4-yl]-3,8-dihydroimidazo[4,5-d]dipyrido[2,3-b:3',4'-f]azepine-bis(trifluoroacetate) |
| 179 | 5-methyl-3-(trifluoromethyl)-1H-pyrazol-4-yl | OH | 400 | 171 | B | Free Base | 2-[5-methyl-3-(trifluoromethyl)-1H-pyrazol-4-yl]imidazo[4,5-d]dipyrido[2,3-b:3',4'-f]azepin-3(8H)-ol |

TABLE 3-continued

| Ex. No. | —W¹—W²—W³—W⁴ | R²ᵃ | MS (M+H) | Prep. Ex. | Pur. Meth. | Salt | Compound Name |
|---|---|---|---|---|---|---|---|
| 180 | 3-methyl-5-trifluoromethyl-1H-pyrazol-4-yl | H | 384 | 171 | A | 2 TFA | 2-[5-methyl-3-(trifluoromethyl)-1H-pyrazol-4-yl]-3,8-dihydroimidazo[4,5-d]dipyrido[2,3-b:3',4'-f]azepine-bis(trifluoroacetate) |
| 181 | 2,3-dimethylphenyl | OH | 356 | 171 | D | Free Base | 2-(2,3-dimethylphenyl)imidazo-[4,5-d]dipyrido[2,3-b:3',4'-f]azepin-3(8H)-ol |
| 182 | 2,3-dimethylphenyl | H | 340 | 171 | A | 2 TFA | 2-(2,3-dimethylphenyl)-3,8-dihydroimidazo[4,5-d]dipyrido[2,3-b:3',4'-f]azepine bis(trifluoroacetate) |
| 183 | 2-(dimethylamino)pyridin-3-yl | OH | 372 | 171 | B | Free Base | 2-[2-(dimethylamino)-pyridin-3-yl]imidazo[4,5-d]dipyrido[2,3-b:3',4'-f]azepin-3(8H)-ol |
| 184 | 2-(dimethylamino)pyridin-3-yl | H | 356 | 171 | A | 3 TFA | 3-(3,8-dihydroimidazo[4,5-d]dipyrido[2,3-b:3',4'-f]azepin-2-yl)-N,N-dimethylpyridin-2-amine-tris(trifluoroacetate) |
| 185 | 2-cyano-6-fluorophenyl | H | | 171 | B | Free Base | 2-(3,8-dihydroimidazo[4,5-d]dipyrido[2,3-b:3',4'-f]azepin-2-yl)-3-fluorobenzonitrile |

TABLE 4 structure: W¹-W²-W³-W⁴ attached to N of pyrazolo-dipyrido-azepine core with R²ᶜ

| Ex. No. | —W¹—W²—W³—W⁴ | R²ᶜ | MS (M+H) | Prep. Ex. | Pur. Meth. | Salt | Compound Name |
|---|---|---|---|---|---|---|---|
| 186 | 2,6-dichlorophenyl | H | 380 | 186 | B | Free Base | 2-(2,6-Dichlorophenyl)-2,8-dihydropyrazolo-[3,4-d]-dipyrido-[2,3-b:3',4'-f]-azepine |

Preparation of Example 1

Intermediate A-1: 2-fluoro-3-iodopyridine

In a 1-neck round-bottom flask N,N-diisopropylamine (20 mL, 0.14 mol) was dissolved in tetrahydrofuran (50 mL) and the mixture was cooled to −78° C. To the resulting mixture, 1.6 M of n-butyllithium in hexanes (86 mL, 0.14 mol) was added and the reaction was stirred at −78° C. for 10 minutes and then warmed to 0° C. and stirred for 15 minutes. 2-fluoropyridine (10 mL, 0.1 mol) was dissolved in 50 mL anhydrous tetrahydrofuran and the resulting mixture was cooled at −78° C. The LDA solution from the first flask was then added. The reaction was stirred at −78° C. for 1.5 hours and then iodine (32 g, 0.13 mol) was added. The mixture was stirred at −78° C. for and additional 1 hour and was then quenched with NH$_4$Cl (aq). The reaction was extracted with EtOAc, washed with brine, dried over MgSO$_4$, and concentrated under vacuum. The residue was purified by chromatography on silica gel (10% EtOAc 90% hexanes) to give 16.3 g of the desired product. $^1$H NMR (400 MHz, CDCl$_3$): δ 8.15-8.20 (m, 2H), 6.95-6.99 (m, 1H). MS [M+H]=223.8

Intermediate A-2: 2-fluoro-3-[(trimethylsilyl)ethynyl]pyridine

Into a 1-neck round-bottom flask was added 2-fluoro-3-iodopyridine (1.0 g, 0.0045 mol), trimethylsilylacetylene (0.95 mL, 6.7 mmol), bis(triphenylphosphine)palladium(II) chloride (0.2 g, 0.2 mmol), copper(I) iodide (0.07 g, 0.4 mmol), and triethylamine (0.94 mL, 6.7 mmol) in N,N-dimethylformamide (20 mL). The reaction was stirred at 25° C. for 16 hours. The reaction was extracted with EtOAc, washed with brine, dried over MgSO$_4$, and concentrated under vacuum. The product was purified by column chromatography on silica gel (10% ethyl acetate 90% hexanes) to give 0.747 g of the desired product. $^1$H NMR (400 MHz, CDCl$_3$): δ 7.86-7.89 (m, 1H), 7.55-7.61 (m, 1H), 6.86-6.90 (m, 1H). MS [M+H]=194.0

Intermediate A-3: 3-ethynyl-2-fluoropyridine

2-Fluoro-3-[(trimethylsilyl)ethynyl]pyridine (8.8 g, 0.046 mol) was dissolved in a mixture of tetrahydrofuran (20 mL) and water (2 mL). A 1.0 M solution of tetra-n-butylammonium fluoride (12 g, 0.046 mol) in THF (46 ml) was then added dropwise at 0° C., and the reaction mixture was stirred for 1 hour. The reaction was extracted with ethyl acetate, and the combined organic extracts were washed with brine (3×), dried over MgSO$_4$ and concentrated. The crude was purified via column chromatography on silica gel (10% ethyl acetate: 90% hexanes) to provide 4.8 g of the desired product. $^1$H NMR (400 MHz, CDCl$_3$): δ 8.20 (m, 1H), 7.88-7.92 (m, 1H), 7.17-7.21 (m, 1H), 3.40 (s, 1H).

Intermediate A-4: 2-fluoro-3-[(4-fluoro-2-nitrophenyl)ethynyl]pyridine

Into a round bottom flask was added 3-ethynyl-2-fluoropyridine (0.3 g, 0.002 mol), 4-fluoro-1-iodo-2-nitrobenzene (0.675 g, 0.00253 mol), bis(triphenylphosphine)palladium (II) chloride (0.09 g, 0.1 mmol), copper(I) iodide (0.04 g, 0.2 mmol), and triethylamine (0.52 mL, 3.7 mmol) in N,N-dimethylformamide (4 mL). The reaction was stirred at room temperature for 2 hours. The reaction was extracted with ethyl acetate, and the combined organic extracts were washed with brine (3×), dried over MgSO$_4$, and purified by column chromatography on silica gel (10% ethyl acetate 90% hexanes), to give 0.443 g of product. $^1$H NMR (400 MHz, CDCl$_3$): δ 8.44-8.50 (m, 1H), 7.99-8.02 (m, 1H), 7.79-7.90 (m, 1H), 7.78-7.82 (m, 1H), 7.37-7.42 (m, 1H), 7.23-7.29 (m, 1H). MS [M+H]=261.0.

Intermediate A-5: 1-(4-fluoro-2-nitrophenyl)-2-(2-fluoropyridin-3-yl)ethane-1,2-dione A 250 mL Erlenmeyer flask, immersed in a water bath at 25° C., was charged with acetone (20 mL,) and 2-fluoro-3-[(4-fluoro-2-nitrophenyl)ethynyl]pyridine (0.443 g, 0.0017 mol). To this solution was added a solution of sodium bicarbonate (0.08 g, 0.001 mol) and magnesium sulfate (0.4 g, 0.003 mol) in water (10 mL). The mixture was stirred with a mechanical stirrer. Powdered potassium permanganate (0.91 g, 0.0058 mol) was then added in one portion, and the mixture was stirred for 4 hours. The unreacted potassium permanganate and the precipitated MnO$_2$ were reduced to soluble Mn$^{2+}$ ions by adding a minimum quantity of NaNO$_2$ (0.14 g) and 10% H$_2$SO$_4$ (1.4 mL) in small portions. The solution was transferred to a 250 mL separating funnel, saturated with NaCl, and extracted with ethyl acetate 2×, dried over MgSO$_4$, concentrated and was purified by column chromatography on silica gel. (20% ethyl acetate, 80% hexanes) to give 0.45 g of the desired product. $^1$H NMR (400 MHz, CDCl$_3$): δ 8.51-8.53 (m, 1H), 8.41-8.46 (m, 1H), 7.88-7.95 (m, 2H), 7.58-7.62 (m, 1H), 7.41-7.45 (m, 1H). MS [M+H]=292.9.

Intermediate A-6: 3-[2-tert-butyl-4-(4-fluoro-2-nitrophenyl)-1H-imidazol-5-yl]-2-fluoropyridine 1-(4-Fluoro-2-nitrophenyl)-2-(2-fluoropyridin-3-yl) ethane-1,2-dione (0.443 g, 0.00152 mol) and pivaldehyde (0.2 mL, 0.002 mol) were dissolved in methanol (4 mL), and ammonium hydroxide (2 mL, 0.01 mol) was added. The reaction was stirred at 25° C. for 4 hours. The reaction was concentrated under vacuum and was purified by column chromatography on silica gel (solvent: 30% ethyl acetate 70% hexanes) to give 0.263 g of the desired product. $^1$H NMR (400 MHz DMSO-d$_6$): δ 9.63 and 9.50 (brs, 1H), 7.04-8.25 (m, 6H), (s, 9H).

Intermediate A-7: 3-[2-tert-butyl-4-(4-fluoro-2-aminophenyl)-1H-imidazol-5-yl]-2-fluoropyridine To a solution of 3-[2-tert-butyl-4-(4-fluoro-2-nitrophenyl)-1H-imidazol-5-yl]-2-fluoropyridine (0.13 g, 0.36 mmol) in 1,4-dioxane (4 mL) was added a solution of sodium dithionite (0.5 g, 0.003 mol) and ammonium hydroxide (0.5 mL, 0.004 mol) in water (4 mL). The reaction was stirred at 25° C. for 4 h and was then extracted with EtOAc. The combined extracts were washed with water 2×, dried over MgSO$_4$ and concentrated in vacuo to give 0.098 g of the desired product. $^1$H NMR (500 MHz, CD$_3$OD): δ 8.28-8.29 (m, 1H), 7.95-7.99 (m, 1H), 7.45-7.46 (m, 1H), 7.34-7.35 (m, 1H), 6.77-7.11 (m, 2H), 6.73-6.77 (m, 1H), 1.56 (s, 9H). MS [M+H]=329.0.

Product (Example 1): 2-tert-butyl-10-fluoro-3,8-dihydroimidazo[4,5-d]pyrido[2,3-b][1]benzazepine 3-[2-tert-Butyl-4-(4-fluoro-2-aminophenyl)-1H-imidazol-5-yl]-2-fluoropyridine (0.070 g, 0.21 mmol) was dissolved in ethanol (2 mL). The reaction was heated in a microwave reactor at 180° C. for 5 min. The reaction was concentrated and purified by column chromatography on silica gel (50% ethyl acetate 50% hexanes) to give 0.052 g of the desired product. $^1$H NMR (500 MHz, CD$_3$OD): δ 8.16-8.18 (m, 1H), 7.85-7.87 (m, 1H), 7.48-7.51 (m, 1H), 7.07-7.10 (m, 1H), 6.82-6.90 (m, 2H), 1.58 (s, 9H). MS [M+H]=309.

Preparation of Example 25

Intermediate B-1: 4-[(vinyloxy)methyl]cyclohexylmethyl methanesulfonate

4-[(Vinyloxy)methyl]cyclohexylmethanol (2.0 g, 0.010 mol) was dissolved in chloroform (20 mL), cooled to 0° C., and then methanesulfonyl chloride (0.85 mL, 0.011 mol) and triethylamine (1.5 mL, 0.011 mol) were added. The reaction was stirred at 0° C. for 2 hours. The reaction was extracted with ethyl acetate, and the extracts were washed with water, brine, and then dried over MgSO$_4$ and concentrated. The product was purified via column chromatography on silica gel (40% ethyl acetate, 60% hexanes), to give 1.53 g of the desired product as a 3:1 mixture of the two diastereomers. $^1$H NMR (400 MHz, CDCl$_3$): δ 6.36-6.41 (m, 1H), 4.04-4.10 (m, 2H), 3.94-3.96 (m, 2H), 3.39-3.43 (m, 2H), 2.92 (s, 3H), 0.90-1.80 (m, 10 H) (major diastereomer).

Intermediate B-2: 4-[(vinyloxy)methyl]cyclohexylacetonitrile

4-[(Vinyloxy)methyl]cyclohexylmethyl methanesulfonate (1.43 g, 0.00576 mol) was dissolved in dimethyl sulfoxide (5 mL, 0.07 mol), and then sodium cyanide (1 g, 0.02 mol) was added. The reaction was stirred at 60° C. for 2 hours at 25° C. for 16 hours. The reaction was extracted with ethyl acetate and the extracts were washed with water, brine 3×, and then dried over MgSO$_4$ and concentrated in vacuo. The product was purified via column chromatography on silica gel (20% ethyl acetate, 80% hexanes) to give 0.90 g of the desired product as a mixture of the two diastereomers. $^1$H NMR (400 MHz, CDCl$_3$): δ 6.33-6.48 (m, 1 H), 4.96-4.13 (m, 1H), 4.00-3.96 (m, 1H), 3.49-3.50 (m, 2H), 2.26 (d, 2H, J=6.8 Hz), 1.86-1.93 (m, 4H), 1.56-1.70 (m, 3H), 1.41-1.52 (m, 1H), 0.95-1.20 (m, 4H). (major isomer).

Intermediate B-3:[4-(hydroxymethyl)cyclohexyl]acetonitrile

4-[(Vinyloxy)methyl]cyclohexylacetonitrile (0.9 g, 0.005 mol) was dissolved in dichloromethane (5 mL), and 1.5 mL of 4 N hydrogen chloride (0.22 g, 0.0060 mol) in dioxane was added with water (0.2 mL). The reaction was stirred for 30 min. and then concentrated to give the product as a 3:1 mixture of diastereomers, (0.75 g). $^1$H NMR (400 MHz, CDCl$_3$): δ 3.451-3.467 d, 2H, J=6.4 Hz), 2.58 (br s, 1H), 2.271-2.288 (d, 2H, J=6.8 Hz), 1.85-1.93 (m, 4H), 1.2-1.8 (m, 4H), 0.95-1.19 (m, 4H) (major diastereomer).

Intermediate B-4:(4-formylcyclohexyl)acetonitrile

To a stirred solution of oxalyl chloride (0.24 mL, 0.0028 mol) in dichloromethane (15 mL) at −78° C. was added a solution of dimethyl sulfoxide (0.23 mL, 0.0032 mol) in dichloromethane (5 mL). After 10 min. a solution of [4-(hydroxymethyl)cyclohexyl]acetonitrile (0.38 g, 0.0025 mol) in dichloromethane (2 mL) was added to the reaction mixture. After 25 min., the reaction mixture was treated with triethylamine (1.7 mL, 0.012 mol), allowed to warm to room temperature, and then poured into 100 mL of saturated aqueous NaCl. The resulting mixture was extracted with two 100 mL portions of ether, dried (MgSO$_4$), and then evaporated under reduced pressure. Chromatography of the residue on silica gel with 1:10 ethyl acetate/hexanes afforded 0.306 g of the desired product. $^1$H NMR (300 MHz, CDCl$_3$): δ 9.64 (s, 1H), 2.35 (d, 2H J=10.8 Hz) 1.10-2.4 (m, 10 H) (major isomer).

Intermediate B-5: 4-[4-(4-fluoro-2-nitrophenyl)-5-(2-fluoropyridin-3-yl)-1H-imidazol-2-yl]cyclohexylacetonitrile 1-(4-Fluoro-2-nitrophenyl)-2-(2-fluoropyridin-3-yl) ethane-1,2-dione (0.300 g, 0.00103 mol) was dissolved in tetrahydrofuran (1 mL), and (4-formylcyclohexyl)acetonitrile (0.17 g, 0.0011 mol) and 7 M ammonia in methanol (0.44 mL, 0.003 mol) were added and the reaction was stirred at 25° C. for 16 hours. The reaction was concentrated and purified via column chromatography on silica gel (60% ethyl acetate 40% hexanes) to give 0.17 g of the desired product. $^1$H NMR (300 MHz, CDCl$_3$): δ 8.30-8.63 (m, 1H), 8.08-8.09 (m, 1H), 7.60-7.70 (m, 1H), 7.35-7.50 (m, 1H), 7.27-7.31 (m, 1H), 7.11 (m, 1H), 2.72-2.81 (m, 1H), 1.10-2.40 (m, 11 H). MS [M+H]=424.0

Product (Example 25): [4-(10-fluoro-3,8-dihydroimidazo[4,5-d]pyrido[2,3-b][1]benzazepin-2-yl)cyclohexyl]acetonitrile To a mixture of 1,4-dioxane (1 mL) with 4-[4-(4-fluoro-2-nitrophenyl)-5-(2-fluoropyridin-3-yl)-1H-imidazol-2-yl]cyclohexylacetonitrile (0.17 g, 0.40 mmol) was added a solution of sodium dithionite (0.2 g, 0.001 mol) and ammonium hydroxide (0.4 mL, 0.003 mol) in water (1 mL), The reaction was stirred at 25° C. for 1 hour, concentrated, and was then extracted with isopropanol (3×1 mL each). The combined extracts were heated in a microwave reactor at 160° C. for 15 minutes, concentrated, and purified via column chromatography on silica gel (50% ethyl acetate 50% hexanes) to give 0.088 g of the desired product. $^1$H NMR (400 MHz, DMSO-d$_6$): δ 8.42 (br s, 1H), 7.07 (m, 1H), 7.66 (m, 1H), 6.99 (m, 1H), 6.80-6.91 (m, 2H), 3.09 (m, 1H), 1.10-2.05 (m, 11H); MS [M+H]=374.0.

Preparation of Example 41

Intermediate C-1: 2-chloro-N,N-diethylnicotinamide

Into a 1-neck round-bottom flask under an atmosphere of nitrogen was dissolved 2-chloronicotinoyl chloride (2.12 g, 0.0120 mol) in methylene chloride (25 mL) and the reaction cooled to 0° C. N-ethylethanamine (2.7 mL, 0.026 mol) was added to the mixture and stirred at 0° C. for 2 hours and then at 20° C. for 16 hours. The reaction was extracted with dichloromethane and the organic extracts were washed with water, brine, dried (MgSO$_4$), and concentrated in vacuo. The crude product was used in the next reaction without further purification. $^1$H NMR (400 MHz, CDCl$_3$): δ 8.42-8.44 (m, 1H), 7.64-7.65 (m, 1H), 7.29-7.63 (m, 1H), 3.75-3.79 (m, 1H), 3.35-3.40 (m, 1H), 3.13-3.22 (m, 2H), 1.82 (t, 3H), 1.088 (t, 3H). MS: [M+1]=213.

Intermediate C-2: N,N-diethyl-2-[(4-methylpyridin-3-yl)amino]nicotinamide

Into a 1-neck round-bottom flask was added 4-methylpyridin-3-amine (1.02 g, 0.00940 mol) and 2-chloro-N,N-diethylnicotinamide (2.00 g, 0.00940 mol) in 1,4-dioxane (20 mL), and then sodium hydride (0.94 g, 0.024 mol) was added. The reaction was heated at reflux for 1 hour. The mixture was allowed to cool and water was added. The mixture was then extracted with ethyl acetate 3× and the combined organic extracts were washed with water, brine, dried over MgSO$_4$, and concentrate in vacuo. Upon cooling, the product crystallized. The crystalline solid was filtered off, washed with ether and dried to give 2.27 g of the desired product. $^1$H NMR (300 MHz, CDCl$_3$): δ 9.15 (s, 1H), 8.21-8.24 (m, 2H), 7.90 (br s, 1H), 7.47 (dd, 1H J1=7.5, J$_2$=1.8 Hz), 7.11 (d, 1H, J=4.8 Hz), 6.75 (dd, 1H, J$_1$=7.5, J$_2$=5.1 Hz), 3.46-3.51 (m, 4H), 2.29 (s, 3H), 1.25 (t, 6H). MS [M+1]=285.

Intermediate C-3: 6,11-dihydro-5H-dipyrido[2,3-b:4',3'-f]azepin-5-one

N,N,N',N'-tetramethylethylenediamine (8.0 mL, 0.053 mol) and N,N-diisopropylamine (7.4 mL, 0.053 mol) were mixed in tetrahydrofuran (43 mL) and then cooled to −78° C. To the mixture was added 2.50 M of n-butyllithium in hexane (21 mL, 0.0525 mol) and stirred at −78° C. for 10 minutes then at 0° C. for 10 minutes. In a separate flask was added N,N-diethyl-2-[4-methylpyridin-3-yl)amino]nicotinamide (5.00 g, 0.0176 mol) in tetrahydrofuran (100 mL) and then cooled to 0° C. under an atmosphere of nitrogen. The mixture from the first flask was added to the second flask and the resulting mixture stirred at 0° C. for 30 minutes. The reaction was quenched with (aq)NH$_4$Cl and was extracted with ethyl acetate. The organic extracts were washed with brine, dried over MgSO$_4$, concentrated, and purified by column chromatography on silica gel (10% methanol 90% ethyl acetate) to give 3.34 g of the desired product. $^1$H NMR (300 MHz, CDCl$_3$): δ 8.49 (s, 1H), 8.41-8.45 (m, 2H), 8.34 (dd, 1H, J$_1$=7.8 Hz, J$_2$=1.5 Hz), 7.78 (br s, 1H), 7.24-7.26 (m, 1H), 6.97-7.25 (m, 1H), 3.89 (s, 2H). MS [M+H]=212.

Intermediate C-4: (6Z)-5H-dipyrido[2,3-b:4',3'-f]azepine-5,6(11H)-dione 6-oxime

A solution of sodium nitrite (3.3 g, 0.048 mol) in water (14.4 mL) was added dropwise to a solution of 6,11-dihydro-5H-dipyrido[2,3-b:4',3'-f]azepin-5-one (4.22 g, 0.02 mol) in acetic acid (80 mL) at room temperature. After the addition was completed, the reaction was stirred for 1.5 hours and 100 mL of water was then added. The mixture was stirred for additional 10 minutes, filtered and dried to give 4.18 g of the desired product. $^1$H NMR (400 MHz, CD$_3$OD): δ 8.70 (s, 1H), 8.48-8.51 (m, 2H), 8.32 (d, 1H, J=5.2 Hz), 7.56 (d, 1H, J=5.6 Hz), 7.07 (dd, 1H, J$_1$=8 Hz, J$_2$=4.8 Hz). MS [M+H]=241.

Intermediate C-5: [4-(3-hydroxy-3,8-dihydroimidazo[4,5-d]dipyrido[2,3-b:4',3'-f]azepin-2-yl)cyclohexyl]acetonitrile A mixture of (6Z)-5H-dipyrido[2,3-b:4',3'-f]azepine-5,6 (11H)-dione 6-oxime (4.83 g, 0.0201 mol), 4-(formylcyclohexyl)acetonitrile (5.0 g, 0.033 mol), ammonium acetate (31.0 g, 0.402 mol), water (7.24 mL) and acetic acid (45.7 mL) was stirred at 80° C. for 3 hrs. The reaction was concentrated, extracted with ethyl acetate, and the combined extracts were washed with brine (3×), dried over MgSO$_4$ and concentrated to give 7.0 g of crude product. The crude product was used in the next reaction without purification. MS [M+H]=373.20.

Product (Example 41): [4-(3,8-dihydroimidazo[4,5-d]dipyrido[2,3-b:4',3'-f]azepin-2-yl)cyclohexyl]acetonitrile A solution of [4-(3-hydroxy-3,8-dihydroimidazo[4,5-d]dipyrido[2,3-b:4',3'-f]azepin-2-yl)cyclohexyl]acetonitrile (7.0 g, 0.019 mol) and triisopropyl phosphite (20 mL, 0.08 mol) in N,N-dimethylacetamide (20 mL) was heated at 160° C. for 2 hours and was then concentrated in vacuo. The residue was purified by column chromatography on silica gel (5% trimethylamine 7.5% methanol and 87.5% ethyl acetate) yielding 4.10 g of product as a 9:1 mixture of the two diastereomers. The pure cis and trans isomers could be obtained by preparative HPLC. $^1$H NMR (300, DMSO-d$_6$): δ 12.73 and 12.01 (br s, 1H), 7.83-7.99 (m, 4H), 7.70 and 7.46 (m, 1H), 6.77 (m, 1H), 2.54-2.63 (m, 1H), 2.49 (m, 2H), 1.84-2.02 (m, 4H), 1.50-1.79 (m, 3H), 1.09-1.24 (m,2H).
$^1$H NMR (300, DMSO-d$_6$+TFA): δ 8.59 (br s, 1H), 8.10 (d, 1H, J=6.0 Hz), 7.96 (s, 1H), 7.91-7.93 (m, 2H), 7.57-7.64 (m, 2H), 6.84-6.89 (m, 1H), 2.59-3.05 (m, 1H), 2.49 (m, 2H), 1.84-2.03 (m, 4H), 1.51-1.79 (m, 3H), 1.06-1.23 (m, 2H). MS [M+H]=357.20

Preparation of Example 46

(6Z)-5H-dipyrido[2,3-b:4',3'-f]azepine-5,6(11H)-dione 6-oxime trifluoroacetate (4.0 g, 11.0 mmol), 3,5-dichloroisonicotinaldehyde (6.0 g, 34.0 mmol), and ammonium acetate (13.0 g, 170 mmol) were stirred in acetic acid (200 mL) and heated to 80° C. for 15 min. The acetic acid was then evaporated in vacuo and the dark red residue was triturated with water (500 mL) to give an orange suspension. The suspension was stirred for 1 hr, filtered, washed with water to give 4.5 g of the desired hydroxyimidazole intermediate.

The hydroxyimidazole intermediate (0.5 g) from above was stirred in acetonitrile (10 mL) and triisopropylphosphite (1 mL) was then added. The mixture was heated to 170° C. in the microwave for 20 min. The yellow precipitate was filtered and washed with acetonitrile to give 0.4 g of the desired product (97% purity). A sample was purified by LCMS to give the bis-TFA salt: $^1$H NMR (400 MHz, CD$_3$OD): δ 8.80 (s, 2H), 8.04 (d, 1H), 8.01 (d, 1H), 7.99 (s, 1H), 7.80 (d, 1H), 7.60 (d, 1H), 6.92 (m, 1H); MF=C$_{18}$H$_{10}$Cl$_2$N$_6$; LCMS calculated for C$_{18}$H$_{10}$Cl$_2$N$_6$ (M+H)=: m/z=381.0.

Preparation of Example 47

Step 1. 2-(2,6-Dichlorophenyl)imidazo[4,5-d]dipyrido[2,3-b:4',3'-f]azepin-3(8H)-ol (6Z)-5H-dipyrido[2,3-b:4',3'-f]azepine-5,6(11H)-dione 6-oxime (11.0 g, 0.0435 mol), ammonium acetate (50 g, 0.65 mol), 2,6-dichlorobenzaldehyde (15.2 g, 0.0870 mol) and acetic acid (200 mL) were heated at 90° C. for 30 minutes. The reaction was concentrated in vacuo to rigorously remove the acetic acid and then the residue was diluted with water (250 mL) and sodium bicarbonate saturated solution (250 mL) added to achieve a basic pH. Ethyl acetate (100 mL) and diethyl ether (300 mL) were then added. The desired product precipitated from the vigorously stirred mixture and was allowed to stand one hour prior to filtration that afforded the product as an off-yellow solid (16.1 g, 93%). This material was used without further purification in the next step. LCMS calculated for C$_{19}$H$_{12}$Cl$_2$N$_5$O (M+H)$^+$: m/z=396. Elemental Analysis calculated for C$_{19}$H$_{13}$Cl$_4$N$_5$; C, 50.36; H, 2.89; Cl, 31.29; N, 15.45. Found: C, 48.93; H, 2.81; Cl, 30.57; N. 14.94.

Step 2. 2-(2,6-Dichlorophenyl)-3,8-dihydroimidazo [4,5-d]dipyrido[2,3-b:4',3'-f]azepine dihydrochloride 2-(2,6-Dichlorophenyl)imidazo[4,5-d]dipyrido[2,3-b:4', 3'-f]azepin-3(8H)-ol (15.2 g, 0.0384 mol) in N,N-dimethylformamide (250 mL) was treated with triethyl phosphite (26.3 mL, 0.153 mol) and the solution was heated to reflux for 2.5 hours. The solution was allowed to cool to room temperature and was concentrated in vacuo. The residual yellow solid was collected by filtration (using 2 L of acetonitrile to wash). The yellow powder was then dissolved in 250 mL of 0.5 N aqueous hydrochloric acid and 50 mL of acetonitrile. The dark red solution was freeze dried for 16 hours to afford the desired product as an orange-red powder (14.0 g, 85%). $^1$H NMR (400 MHz, d$_6$-DMSO): δ 8.81 (s, 1H), 8.09 (d, J=6.2 Hz, 1H), 8.03 (s, 1H), 7.94 (dd, J=5.0, 1.6 Hz, 1H), 7.69-7.57 (m, 5H), 6.86 (dd, J=7.5, 4.9 Hz, 1H). LCMS calculated for C$_{19}$H$_{12}$Cl$_2$N$_5$ (M+H)$^+$: m/z=380.

Preparation of Example 171

Intermediate D-1: 2-Fluoronicotinaldehyde

A solution of n-butyllithium (77 mL, 2.5 M in hexane, 0.19 mol) was added to a solution of N,N-diisopropylamine (27 mL, 0.19 mol) in dry THF (400 mL) under an atmosphere of nitrogen at −78° C. After the addition, the mixture was warmed to 0° C. for 15 minutes and then cooled again to −78° C. 2-Fluoropyridine (15.0 mL, 0.174 mol) was added dropwise to the mixture and stirred at −78° C. After 45 minutes, a pale yellow precipitate formed. N,N-Dimethylformamide (27 mL, 0.35 mol) was added slowly via syringe maintaining temperature below −55° C. After ten minutes, the cooling bath was removed and the mixture slowly warmed to room temperature. The reaction was quenched with NH$_4$Cl/H$_2$O and then 4 M HCl to adjust the pH ~7. NaHCO$_3$/H$_2$O was then added to adjust the pH 9-10, and then extracted three times with Et$_2$O. The combined extracts were washed with brine, dried over MgSO$_4$, filtered and concentrated to a yellow oil. The residue was purified by chromatography on silica gel, eluting with 25% EtOAc/hexane to provide 2-fluoronicotinaldehyde as a pale yellow oil (10.0 g, 45%). $^1$H NMR (CDCl$_3$) δ 10.33 (s, 1H), 8.49 (m, 1H), 8.32 (m, 1H), 7.40 (m, 1H). LC/MS: 126 (M+H)$^+$.

Intermediate D-2: tert-Butyl (3-methylpyridin-4-yl)carbamate

Di-tert-butyldicarbonate (10.0 g, 0.0458 mol) was added slowly in portions to a solution of 3-methylpyridin-4-amine (4.13 g, 0.0382 mol) dissolved in tert-butyl alcohol (60 mL). Vigorous bubbling was observed during the addition. After stirring at room temperature overnight, the solvent was removed in vacuo to provide an oily residue which was partitioned between NaHCO$_3$/water and ethyl acetate. The mixture was extracted 3× with ethyl acetate and the combined extracts were washed with brine, dried over MgSO$_4$, filtered, and concentrated. The crude product was purified by chromatography on silica gel eluting with 75% ethyl acetate/hexane to 100% ethyl acetate to provide tert-butyl (3-methylpyridin-4-yl)carbamate as a white solid (7.90 g, 99%). $^1$H NMR (DMSO-d$_6$) δ 8.80 (bs, 1H), 8.25 (m, 2H), 7.65 (d, 1H), 2.19 (s, 3H), 1.49 (s, 9H). LC/MS: 209 (M+H)$^+$.

Intermediate D-3: tert-Butyl 3-[2-(2-fluoropyridin-3-yl)-2-hydroxyethyl]pyridin-4-ylcarbamate A solution of tert-butyl (3-methylpyridin-4-yl)carbamate (1.00 g, 4.80 mmol, Intermediate D-2) in THF (50 mL) was cooled to −78° C. under an atmosphere of nitrogen. A solution of n-butyllithium (4.80 mL, 2.5 M in hexane, 12.0 mmol) was added slowly maintaining the internal temperature below −65° C. After the addition, the mixture was warmed to 0° C. for 20 minutes (orange suspension turned homogeneous). The solution was then cooled to −78° C. and 2-fluoronicotinaldehyde (0.901 g, 7.20 mol, Intermediate D-1) in THF (5 mL) was added dropwise. After 10 minutes, the dark red/brown mixture was allowed to slowly warm to 0° C. After 30 minutes, the reaction was quenched with NH$_4$Cl/water. The mixture was further diluted with NaHCO$_3$/water and extracted three times with ethyl acetate. The combined extracts were washed with brine, dried over MgSO$_4$, filtered, and concentrated. The residue was purified by chromatography on silica gel eluting with 75% ethyl acetate/hexane. Pure fractions were combined, concentrated and then triturated with ethyl acetate to provide the desired product as a white solid (0.55 g, 34%). $^1$H NMR (DMSO-d$_6$) δ 9.09 (s, 1H), 8.23 (d, 1H), 8.09 (d, 1H), 8.02 (s, 1H), 7.85 (m, 1H), 7.67 (d, 1H), 7.29 (m, 1H), 6.32 (d, 1H), 5.03 (m, 1H), 3.00 (m, 2H), 1.47 (s, 9H). LC/MS: 334 (M+H)$^+$.

Intermediate D-4: 2-(4-Aminopyridin-3-yl)-1-(2-fluoropyridin-3-yl)ethanol tert-Butyl 3-[2-(2-fluoropyridin-3-yl)-2-hydroxyethyl]pyridin-4-ylcarbamate (2.00 g, 6.00 mmol, Intermediate D-3) was dissolved in methylene chloride (40 mL) and trifluoroacetic acid (40 mL). The solution was stirred at room temperature for one hour. The solution was concentrated in vacuo and the residue was dissolved in ethyl acetate and washed with NaHCO$_3$/water. The aqueous layer was then saturated with solid NaCl, and extracted with ethyl acetate repeatedly (8 times). The combined extracts were dried over MgSO$_4$, filtered, and concentrated to provide an oil which slowly solidified. The desired product was isolated as an off-white solid and was used directly in the next step without further purification. $^1$H NMR (DMSO-d$_6$) δ 8.10 (d, 1H), 8.01 (m, 1H), 7.90 (d, 1H), 7.77 (s, 1H), 7.34 (m, 1H), 7.18 (m, 1H), 6.59 (m, 2H), 5.80 (bs, 1H), 5.00 (m, 1H), 2.83 (m, 2H). LC/MS: 234 (M+H)$^+$.

Intermediate D-5: 6,11-Dihydro-5H-dipyrido[2,3-b:3',4'-f]azepin-5-ol 2-(4-Aminopyridin-3-yl)-1-(2-fluoropyridin-3-yl)ethanol (6.00 mmol, Intermediate D-4) was dissolved in THF (200 mL) under an atmosphere of nitrogen. The solution was cooled to −78° C., then a solution of potassium tert-butoxide (36.0 mL, 1.0 M in THF, 36.0 mmol) was added dropwise. The mixture turned orange/red, then became darker brown. After the addition, the mixture was slowly warmed to 0° C. After stirring for 3 hours at 0° C., the reaction mixture was poured into a cold solution of saturated NaCl/water and HCl (2.0 mL, 12 M, 24 mmol) and stirred (pH ~13) and then extracted 3× with ethyl acetate. The combined extracts were washed with brine, dried over Na$_2$SO$_4$, filtered, and concentrated. The crude product was adsorbed onto silica gel and then chromatographed on silica gel eluting with 10% methanol/CH$_2$Cl$_2$ to give the desired product as a white solid (1.15 g, 89%).
$^1$H NMR (DMSO-d$_6$) δ 9.63 (s, 1H), 8.12 (m, 1H), 8.09 (m, 2H), 7.72 (m, 1H), 7.07 (d, 1H), 6.87 (dd, 1H), 5.55 (d, 1H), 4.84 (m, 1H), 3.00 (m, 2H). LC/MS: 214 (M+H)$^+$.

Intermediate D-6: 6,11-Dihydro-5H-dipyrido[2,3-b:3',4'-f]azepin-5-one

Dess-Martin periodinane (0.810 g, 1.91 mmol) was added to a solution of 6,11-dihydro-5H-dipyrido[2,3-b:3',4'-f]azepin-5-ol (0.370 g, 1.74 mmol, Intermediate D-5) in dichloromethane (30 mL) under an atmosphere of nitrogen and stirred for 1 h. The yellow mixture was poured into a solution of sodium bisulfate in water and stirred for 5 minutes. The mixture was then diluted with dichloromethane and sodium bicarbonate was added to adjust the pH to 8-9. The mixture was extracted three times with dichloromethane and the combined extracts were dried over sodium sulfate, filtered, and concentrated. The crude product residue was adsorbed onto silica gel and chromatographed on a silica gel column eluting with 10% methanol/dichloromethane to provide the desired product as a light tan solid (330 mg, 90%). $^1$H NMR (DMSO-d$_6$): δ 10.55 (s, 1H), 8.51 (dd, 1H), 8.42 (s, 1H), 8.35 (d, 1H), 8.18 (dd, 1H), 7.33 (d, 1H), 7.06 (dd, 1H), 3.82 (s, 2H). LC/MS: 212 (M+H)$^+$.

Intermediate D-7: 5H-dipyrido[2,3-b:3',4'-f]azepine-5,6(11H)-dione 6-oxime

A solution of sodium nitrite (0.259 g, 3.75 mmol) in water (1.0 mL) was added dropwise to a solution of 6,11-dihydro-5H-dipyrido[2,3-b:3',4'-f]azepin-5-one (0.330 g, 1.56 mmol, Intermediate D-6) dissolved in acetic acid (6.0 mL). The mixture was stirred at room temperature for 90 minutes at which time a precipitate had formed. The yellow mixture was reduced to about half original volume in vacuo, and then diluted with 20 mL water and stirred for 30 minutes. A thick precipitate formed which was collected by suction filtration, washed with water and then dried in a vacuum oven at 50° C. overnight. The desired product was obtained as a yellow powder (224 mg, 60%). (2 peaks, ~2:1 ratio of oxime isomers). $^1$H NMR (DMSO-d$_6$, ~2:1 mixture of oxime isomers): δ 12.55 & 12.32 (bs, 1H), 11.41 & 11.18 (bs, 1H), 8.67 (m, 2H), 8.54-8.25 (m, 2H), 7.56 (m, 1H), 7.27 (m, 1H). LC/MS: 241 (M+H)$^+$ Intermediate D-8: 2-(3,5-dichloropyridin-4-yl)imidazo[4,5-d]dipyrido[2,3-b:3',4'-f]azepin-3(8H)-ol 5H-Dipyrido[2,3-b:3',4'-f]azepine-5,6(11H)-dione 6-oxime (0.100 g, 0.416 mmol, Intermediate D-7) ammonium acetate (0.60 g, 8.0 mmol), acetic acid (2 mL), water (0.2 mL) and 3,5-dichloroisonicotinaldehyde (0.293 g, 1.66 mmol) were combined in a capped vial and heated to 80° C. for 2 h. The mixture was cooled to room temperature, and diluted with aqueous NaHCO$_3$ and brine. The mixture was extracted three times with ethyl acetate and the combined extracts were washed with brine, dried over MgSO$_4$, filtered, and concentrated to provide the crude intermediate product as a dark oil which was used directly in the next step. LC/MS: 397, 399 (M+H)$^+$.

Product (Example 171): 2-(3,5-dichloropyridin-4-yl)-3,8-dihydroimidazo[4,5-d]dipyrido[2,3-b:3',4'-f]azepine The crude product from above, 2-(3,5-dichloropyridin-4-yl)imidazo[4,5-d]dipyrido[2,3-b:3',4'-f]azepin-3(8H)-ol, (0.416 mmol, Intermediate D-8) was dissolved in N,N-dimethylacetamide (1.50 mL) and triisopropyl phosphite (0.19 mL, 0.83 mmol) and heated to 160° C. for 1 h. The mixture was cooled to room temperature, then diluted with acetonitrile and water and the product isolated by preparative HPLC. The pure fractions were combined, concentrated, and then lyophilized to provide the desired product as a yellow powder. $^1$H NMR (DMSO-d$_6$, 2 tautomers) δ 13.01 (bs, 1H), 8.84 (s, 2H), 8.65 and 8.52 (bs, 1H), 8.42 and 8.15 (bs, 1H), 7.98 (m, 1H), 7.87 (m, 1H), 7.75 and 7.44 (d, 1H), 6.81 (m, 2H). LC/MS: 381, 383 (M+H)$^+$.

Preparation of Example A-9

Step 1: 4-bromo-5-methyl-1-(tetrahydro-2H-pyran-2-yl)-3-(trifluoromethyl)-1H-pyrazole A solution of 4-bromo-5-methyl-3-(trifluoromethyl)-1H-pyrazole (1.00 g, 4.37 mmol) and p-toluenesulfonic acid monohydrate (80 mg, 0.4 mmol) in CHCl$_3$ (3.5 mL) was cooled to 0° C. and dihydropyran (480 μL, 5.2 mmol) was added dropwise. The reaction was stirred at 0° C. for 1.5 h. The solvent was removed in vacuo and the residue was purified by column chromatography to obtain the desired product (1.18 g, 86%). $^1$H NMR (400 MHz, CDCl$_3$): δ 5.35 (dd, 1H), 3.98 (m, 1H), 3.65 (m, 1H), 2.40 (m, 1H), 2.37 (s, 3H), 2.12 (m, 1H), 1.96 (m, 1H), 1.64 (m, 3H).

Step 2: 5-methyl-1-(tetrahydro-2H-pyran-2-yl)-3-(trifluoromethyl)-1H-pyrazole-4-carbaldehyde A solution of 4-bromo-5-methyl-1-(tetrahydro-2H-pyran-2-yl)-3-(trifluoromethyl)-1H-pyrazole (1.17 g, 3.74 mmol) in THF (13 mL) was cooled to −78° C., then n-BuLi (1.6 M in hexane, 3.7 mL, 6.0 mmol) was added dropwise. The reaction was held at −78° C. for 10 minutes, then DMF (580 μL, 7.5 mmol) was added and the reaction was stirred at −78° C. for 1.5 h. The reaction was quenched at −78° C. by addition of sat'd NH$_4$Cl and ether, the phases were separated and the aqueous phase was washed with ether. The combined organic phase was washed with water, then sat'd NaCl, dried over MgSO$_4$ and reduced to dryness in vacuo to give the crude product, which was used without further purification (1.04 g). $^1$H NMR (400 MHz, CDCl$_3$): δ 10.0 (s, 1H), 5.41 (m, 1H), 4.00 (m, 1H), 3.66 (m, 1H), 2.68 (s, 3H), 2.41 (m, 1H), 2.17 (m, 1H), 2.00 (m, 1H), 1.69 (m, 3H).

Step 3: 2-[5-methyl-1-(tetrahydro-2H-pyran-2-yl)-3-(trifluoromethyl)-1H-pyrazol-4-yl]-3,8-dihydroimidazo[4,5-d]dipyrido[2,3-b:4',3'-f]azepine trifluoroacetate A mixture of (6Z)-5H-dipyrido[2,3-b:4',3'-f]azepine-5,6 (11H)-dione 6-oxime (930 mg, 3.9 mmol), ammonium acetate (5.58 g, 72.4 mmol) and 5-methyl-1-(tetrahydro-2H-pyran-2-yl)-3-(trifluoromethyl)-1H-pyrazole-4-carbaldehyde (2.03 g, 7.74 mmol) in acetic acid (5.6 mL) was stirred at 80° C. for 2 h. The reaction was cooled to ambient temperature and partitioned between water and 3:1 CHCl$_3$:isopropanol. The phases were separated and the aqueous phase was washed with additional solvent. The combined organic phase was washed with water, sat'd NaHCO$_3$, then sat'd NaCl, dried over MgSO$_4$ and reduced to dryness in vacuo to leave 2-[5-methyl-1-(tetrahydro-2H-pyran-2-yl)-3-(trifluoromethyl)-1H-pyrazol-4-yl]imidazo[4,5-d]dipyrido[2,3-b:4',3'-f]azepin-3(8H)-ol, which was used without further purification. MS (EI) m/z=484.2 (M+H).

To a solution of 2-[5-methyl-1-(tetrahydro-2H-pyran-2-yl)-3-(trifluoromethyl)-1H-pyrazol-4-yl]imidazo[4,5-d]dipyrido[2,3-b:4',3'-f]azepin-3(8H)-ol (1.9 g, 3.9 mmol) in N,N-dimethylacetamide (21.8 mL) was added triisopropyl phosphite (3.6 mL, 16 mmol) and the solution was heated to 160° C. for 45 min. The reaction was partitioned between water and EtOAc and the aqueous phase was washed with additional EtOAc. The combined organic phase was washed with water, then sat'd NaCl, dried over MgSO$_4$ and reduced to dryness in vacuo to give the crude product. The compound was purifed by preparative LCMS to obtain the desired product as a TFA salt (1.45 g, 64%). $^1$H NMR (400 MHz, DMSO-d$_6$): δ 8.68 (bs, 1H), 8.12 (d, 1H), 8.04 (s, 1H), 7.94 (dd, 1H), 7.64 (m, 2H), 6.87 (dd, 1H), 5.63 (dd, 1H), 3.90 (m, 1H), 3.71 (m, 1H), 2.40 (s, 3H), 2.24 (m, 1H), 1.96 (m, 2H), 1.70 (m, 1H), 1.55 (m, 2H). MS (EI) m/z=468.1 (M+H).

Step 4: 2-[5-methyl-3-(trifluoromethyl)-1H-pyrazol-4-yl]-3,8-dihydroimidazo[4,5-d]dipyrido[2,3-b:4',3'-f]azepine bis(trifluoroacetate)

To a solution of 2-[5-methyl-1-(tetrahydro-2H-pyran-2-yl)-3-(trifluoromethyl)-1H-pyrazol-4-yl]-3,8-dihydroimidazo[4,5-d]dipyrido[2,3-b:4',3'-f]azepine trifluoroacetate (715 mg, 1.23 mmol) in methanol (16 mL) was added 1.25 mL concentrated HCl and the reaction was stirred at 50° C. for 3 h. The reaction was reduced in vacuo and then purified by preparative LCMS to obtain the desired product as a bis-TFA salt (548 mg, 73%). $^1$H NMR (400 MHz, DMSO-d$_6$): δ 13.8 (bs, 1H), 8.60 (bs, 1H), 8.10 (d, 1H), 8.01 (s, 1H), 7.94 (dd, 1H), 7.61 (m, 2H), 6.88 (dd, 1H), 2.35 (s, 3H). $^{19}$F NMR (400 MHz, DMSO-d$_6$): δ-59.476 (3F), -74.791 (6F). MS (EI) m/z=384. (M+H).

Preparation of Example A-10

Step 1: 5-(difluoromethyl)-3-methyl-4,5-dihydro-1H-pyrazol-5-ol

To a solution of 1,1-difluoropentane-2,4-dione (2.5 g, 0.018 mol) in tetrahydrofuran (32 mL) was added hydrazine hydrate (0.98 mL, 0.020 mol) in tetrahydrofuran (32 mL) dropwise. The reaction was stirred at 25° C. for 16 hours and then concentrated in vacuo. The residue was used in the next reaction without further purification. $^1$H NMR (CDCl$_3$): δ 5.68-5.96 (t, 1H), 5.50-5.80 (br s, 1H), 2.98 (dd, 1H), 2.68 (dd, 1H), 2.01 (s, 3H).

Step 2: 4-bromo-3-(difluoromethyl)-5-methyl-1H-pyrazole

To a solution of 5-(difluoromethyl)-3-methyl-4,5-dihydro-1H-pyrazol-5-ol (1.00 g, 6.66 mmol) in methylene chloride (20 mL) was added bromine (0.43 mL, 8.3 mmol) dropwise. The reaction was stirred at 25° C. for 3 h. and then quenched with a Na$_2$S$_2$O$_4$ solution and neutralized with NaHCO$_3$. The reaction was extracted with dichloromethane and the organic extracts were washed with water, brine, dried (MgSO$_4$), and concentrated in vacuo. $^1$H NMR (CDCl$_3$): δ 6.56-6.82 (t, 1H), 2.33 (s, 3H). Mass spec(EI) m/z=211&213 (M+1).

Step 3: 4-bromo-3-(difluoromethyl)-5-methyl-1-(tetrahydro-2H-pyran-2-yl)-1H-pyrazole To a solution of 4-bromo-3-(difluoromethyl)-5-methyl-1H-pyrazole (1.40 g, 6.63 mmol) in chloroform (30.0 mL, 0.375 mol) was added p-toluenesulfonic acid monohydrate (0.13 g, 0.66 mol) at 0° C. Dihydropyran (0.91 mL, 0.010 mol) was added and stirred at 25° C. for 2 h. The reaction was extracted with ethyl acetate and the organic extracts were washed with NaHCO$_3$, water, saturated NaCl, dried (MgSO$_4$) and concentrated in vacuo. The compound was chromatographed on silica gel using 10% EtOAc/hexanes to give the desired product. $^1$H NMR (CDCl$_3$): δ 6.51-6.78 (t, 1H), 5.31 (dd, 1H), 4.01(m, 1H), 3.65 (m, 1H), 2.40 (m, 1H), 2.35 (s, 3H), 2.21 (m, 1H), 1.95 (m, 1H), 1.50-1.70 (m, 3H).

Step 4: 3-(difluoromethyl)-5-methyl-1-(tetrahydro-2H-pyran-2-yl)-1H-pyrazole-4-carbaldehyde A solution of 4-bromo-3-(difluoromethyl)-5-methyl-1-(tetrahydro-2H-pyran-2-yl)-1H-pyrazole (0.60 g, 2.0 mmol) in tetrahydrofuran (7.00 mL, 86.3 mmol) was cooled at -78° C. Into the reaction was added 1.6 M of n-butyllithium in hexane (2.00 mL) and was stirred at -78° C. for 5 min. N,N-Dimethylformamide (0.31 mL, 4.1 mmol) was added and stirred at -78° C. for 1 h. The reaction was extracted with ethyl acetate and the organic extracts were washed with water, saturated NaCl, dried (MgSO$_4$) and concentrated in vacuo. The crude product was used in the next reaction without further purification. $^1$H NMR (CDCl$_3$): δ 10.12 (s, 1H), 6.81-6.95 (t, 1H), 5.38 (m, 1H), 4.03 (m, 1H), 3.68 (m, 1H), 2.66 (s, 3H), 2.42 (m, 1H), 2.14 (m, 1H), 1.96 (m, 1H), 1.50-1.75 (m, 3H).

Step 5: 2-[3-(difluoromethyl)-5-methyl-1-(tetrahydro-2H-pyran-2-yl)-1H-pyrazol-4-yl]imidazo[4,5-d]dipyrido[2,3-b:4',3'-f]azepin-3(8H)-ol A mixture of (6Z)-5H-dipyrido[2,3-b:4',3'-f]azepine-5,6 (11H)-dione 6-oxime (1.00 g, 4.16 mmol), ammonium acetate (6.00 g, 77.8 mmol) and 3-(difluoromethyl)-5-methyl-1-(tetrahydro-2H-pyran-2-yl)-1H-pyrazole-4-carbaldehyde (2.50 g, 8.19 mmol) in acetic acid (6.0 mL, 0.106 mol) was stirred at 80° C. for 2 h. The reaction was partitioned between dichloromethane/isopropanol (5:1) and water and the organic extract was washed with NaHCO$_3$, brine, dried (MgSO$_4$) and concentrated in vacuo. The residue was used in the next reaction without purification. Mass spec: (EI) m/z=466 (M+1).

Step 6: 2-[3-(difluoromethyl)-5-methyl-1-(tetrahydro-2H-pyran-2-yl)-1H-pyrazol-4-yl]-3,8-dihydroimidazo[4,5-d]dipyrido[2,3-b:4',3'-f]azepine A solution of 2-[3-(difluoromethyl)-5-methyl-1-(tetrahydro-2H-pyran-2-yl)-1H-pyrazol-4-yl]imidazo[4,5-d]dipyrido[2,3-b:4',3'-f]azepin-3 (8H)-ol (1.94 g, 4.17 mmol) in N,N-dimethylacetamide (30 mL, 0.3226 mol) was heated at 160° C. for 2.5 hours with triisopropyl phosphite (4.0 mL, 0.0174 mol). The reaction was allowed to cool and then poured into 50 mL water. The reaction was extracted with ethyl acetate and the organic extracts were washed with water, saturated NaCl, dried (MgSO$_4$) and concentrated in vacuo. The reaction was chromatographed on silica gel using 3% Et$_3$N with ethyl acetate, and 3% MeOH/ethyl acetate to give the desired product. $^1$H NMR (CDCl$_3$): δ 9.52 and 9.45 (brs, 1H), 7.87-8.11 (m, 4H), 6.74-7.61 (m, 3H), 6.10 and 6.13 (br s, 1H), 5.40 (dd, 1H), 4.11 (m, 1H), 3.71 (m, 1H), 2.80 (s, 3H), 2.44 (m, 1H), 2.17 (m, 1H), 1.95 (m, 1H), 1.60-1.80 (m, 3H). Mass spec(EI) m/z=450 (M+1).

Step 7: 2-[3-(difluoromethyl)-5-methyl-1H-pyrazol-4-yl]-3,8-dihydroimidazo[4,5-d]dipyrido[2,3-b:4',3'-f]azepine 2-[3-(difluoromethyl)-5-methyl-1-(tetrahydro-2H-pyran-2-yl)-1H-pyrazol-4-yl]-3,8-dihydroimidazo[4,5-d]dipyrido[2,3-b:4',3'-f]azepine (1.69 g, 3.76 mmol) was dissolved in methanol (50.00 mL, 1.234 mol) and concentrated HCl (2.00 mL) was added. The reaction was stirred at 25° C. for 20 h. The reaction was neutralized with NaHCO$_3$ and was extracted with ethyl acetate and the organic extracts were washed with water, saturated NaCl, dried (MgSO$_4$), concentrated in vacuo to a reduced volume and crystallized from MeOH/EtOAc to give the desired product (1.10 g). A portion of this (0.70 g) was suspended in methanol and 1.00 M of HCl in ether (6.00 mL) was added at which time the compound was completely dissolved. The reaction was concentrated in vacuo to reduce solvent to a minimal volume and ether was added. The crystallized solid was washed with ether and dried to give the bis hydrochloride salt (0.82 mg). Free base $^1$H NMR (DMSO-d$_6$): δ 8.72 (br s, 1H), 8.14 (d, 1H), 8.01 (s, 1H), 7.95 (dd, 1H), 7.80 (m, 1H), 7.76 (d, 1H), 7.11-7.38 (t, 1H), 6.90 (dd, 1H), 2.48 (s, 3H). Mass spec (EI) m/z=366 (M+1).

Preparation of Example A-98

Step 1: [(3,5-dichlorobenzyl)oxy](triisopropyl)silane

To a solution of (3,5-dichlorophenyl)methanol (10.0 g, 56.5 mmol) in methylene chloride (100 mL) at 0° C. was added 2,6-lutidine (16.4 mL, 141 mmol) followed by triisopropylsilyl triflate (19.7 mL, 73.4 mmol), and was stirred at 0° C. for 2 hours. The reaction was diluted with water and the organic layer was separated, washed with brine, dried over Na$_2$SO$_4$, filtered and concentrated. The residue was purified by chromatography on silica gel, eluting with hexane to provide the desired product (14.8 g, 79%). LC/MS: 333 (M+H)$^+$, $^1$H NMR (CDCl$_3$) δ 7.23 (s, 3H), 4.78 (s, 2H), 1.18 (m, 3H), 1.03 (s, 18H).

Step 2: 2,6-dichloro-4-[(triisopropylsilyl)oxy]methylbenzaldehyde

[(3,5-Dichlorobenzyl)oxy](triisopropyl)silane (14.8 g, 44.4 mmol) was stirred in tetrahydrofuran (30 mL) and cooled to −78° C. A solution of n-butyllithium (30.5 mL, 1.6 M in hexane, 48.8 mmol) was added dropwise and the mixture was stirred at −78° C. for 1 hour. N,N-dimethylformamide (4.47 mL, 57.7 mmol) was added and the mixture was allowed to warm to room temperature. A solution of 1 N HCl saturated with NaCl (15 mL) was added. The organic layer was separated and concentrated. The crude product was purified by chromatography on silica gel eluting with hexane to 10% ethyl acetate/hexane. Pure fractions were combined and concentrated to provide the desired product as a white solid (13.0 g, 81%). $^1$H NMR (CDCl$_3$) δ 10.43 (s, 1H), 7.39 (s, 2H), 4.80 (s, 2H), 1.18 (m, 3H), 1.03 (s, 18H). LC/MS: 361 (M+H)$^+$.

Step 3: 2-(2,6-dichloro-4-[(triisopropylsilyl)oxy]methylphenyl)imidazo[4,5-d]dipyrido[2,3-b:4',3'-f]azepin-3(8H)-ol A solution of (6Z)-5H-dipyrido[2,3-b:4',3'-f]azepine-5,6(11H)-dione 6-oxime trifluoroacetate (1.0 g, 2.82 mmol), 2,6-dichloro-4-[(triisopropylsilyl)oxy]methylbenzaldehyde (2.04 g, 5.64 mmol) and ammonium acetate (3.3 g, 42 mmol) was stirred in acetic acid (30 mL) and heated in a microwave for 5 minutes at 130° C. Evaporation gave the crude product (1.6 g, 100%) which was used without further purification in the next step. LC/MS: 582 (M+H)$^+$.

Step 4: [3,5-dichloro-4-(3,8-dihydroimidazo[4,5-d]dipyrido[2,3-b:4',3'-f]azepin-2-yl)phenyl]methanol bis(trifluoroacetate)

2-(2,6-Dichloro-4-[(triisopropylsilyl)oxy]methylphenyl)imidazo[4,5-d]dipyrido[2,3-b:4',3'-f]azepin-3(8H)-ol (1.60 g, 2.80 mmol) was stirred in acetonitrile (60 mL) and triisopropyl phosphite (6.66 mL, 29.0 mmol) was added. The suspension was heated twice in the microwave at 175° C. for 20 minutes. Purification by preparative LCMS gave the desired product (0.48 g, 26%). $^1$H NMR (DMSO-d$_6$) δ 8.60 (s, 1H), 8.05 (d, 1H), 8.02 (s, 1H), 7.92 (d, 1H), 7.60 (m, 4H), 6.85 (m, 1H), 4.60 (s, 2H). LC/MS: 410 (M+H)$^+$.

Preparation of Example A-101

5-Chloro-4(3,8-dihydroimidazo[4,5-d]dipyrido[2,3-b:4',3'-f]azepine-2yl)nicotinonitrile tris(trifluoroacetate)

2-(3,5-Dichloropyridin-4-yl)-3,8-dihydroimidazo[4,5-d]dipyrido[2,3-b:4',3'-f]azepine bis(trifluoroacetate) (200 mg, 0.3 mmol), zinc cyanide (231 mg, 1.97 mmol), and tetrakis-(triphenylphosphine)palladium(0) (190 mg, 0.16 mmol) were stirred in N,N-dimethylformamide and degassed for 10 minutes by bubbling with nitrogen gas. The mixture was heated in a microwave for 20 minutes at 175° C. Purification by preparative LCMS gave the desired product (25 mg, 13%). $^1$H NMR (DMSO-d$_6$): δ 9.20 (d, 2H), 8.60 (m, 1H), 8.0 (m, 1H), 7.65 (m, 1H), 6.90 (m, 1H). LC/MS: 372 (M+H)$^+$.

Preparation of Example A-123

Step 1: 2-[2,6-dichloro-4-(chloromethyl)phenyl]-3,8-dihydroimidazo[4,5-d]dipyrido[2,3-b:4',3'-f]azepine To a solution of [3,5-dichloro-4-(3,8-dihydroimidazo[4,5-d]dipyrido[2,3-b:4',3'-f]azepin-2-yl)phenyl]methanol bis (trifluoroacetate) (20.0 g, 0.03 mmol) in toluene (1.0 mL) was added triethylamine (11 µL, 0.08 mmol) and stirred for 5 minutes, followed by the addition of thionyl chloride (5.0 µL, 0.06 mmol) at room temperature for 16 hours. The reaction mixture was diluted with methanol and purified by preparative LCMS at pH 10 to give the desired product (8.7 mg, 65%). LC/MS: 428 (M+H)$^+$.

Step 2: [3,5-dichloro-4-(3,8-dihydroimidazo[4,5-d]dipyrido[2,3-b:4',3'-f]azepin-2-yl)phenyl]acetonitrile A solution of 2-[2,6-dichloro-4-(chloromethyl)phenyl]-3,8-dihydroimidazo[4,5-d]dipyrido[2,3-b:4',3'-f]azepine (8.7 mg, 0.02 mmol), sodium cyanide (2.0 mg, 0.04 mmol) in dimethyl sulfoxide (1.0 mL) was stirred at 25° C. for 1 hour. The reaction mixture was diluted with methanol and purified on preparative LCMS at pH 10 to give the desired product (3.8 mg, 45%). LC/MS: 419 (M+H)$^+$.

Preparation of Example A-129

1-[3,5-dichloro-4-(3,8-dihydroimidazo[4,5-d]dipyrido[2,3-b:4',3'-f]azepin-2-yl)phenyl]-N,N-dimethylmethanamine A solution of dimethylamine (23 µL, 2.0 M in tetrahydrofuran) was dissolved in N,N-dimethylformamide (0.5 mL) and cooled to 0° C. Sodium hydride (1.1 mg, 0.05 mmol) was added and the mixture was stirred for 15 minutes. 2-[2,6-dichloro-4-(chloromethyl)phenyl]-3,8-dihydroimidazo[4,5-d]dipyrido[2,3-b:4',3'-f]azepine (10.0 mg, 0.02 mmol) was added and the mixture was stirred at room temperature for 16 hours. The reaction mixture was diluted with methanol and purified on preparative LCMS at pH 10 to give the desired product (3.2 mg, 31%). LC/MS: 437 (M+H)$^+$.

Preparation of Example A-133

Step 1: 3,5-dichlorophenyl ethyl sulfide

A solution of 3,5-dichlorobenzenethiol (1.50 g, 8.4 mmol), iodoethane (1.34 mL, 16.8 mmol), potassium carbonate (1.74 g, 12.6 mmol) and methylene chloride (10 mL) was stirred at 25° C. for 30 minutes. The reaction was diluted with water and extracted with ethyl acetate three times, dried over sodium sulfate, filtered and concentrated. The residue was purified by chromatography on silica gel to give the desired product (1.69 g, 97%). LC/MS: 207 (M+H)$^+$.

Step 2: 2,6-dichloro-4-(ethylthio)benzaldehyde

A solution of 3,5-dichlorophenyl ethyl sulfide (1.0 g, 4.8 mmol) in tetrahydrofuran (4 mL) was cooled to −78° C. A solution of n-butyllithium (4.5 mL, 1.6 M in hexane) was added dropwise and the mixture was stirred at −78° C. for 45 minutes. N,N-dimethylformamide (4.47 mL, 57.7 mmol) was added and the mixture was stirred at −78° C. for 1 hour. The mixture was stirred at room temperature for 2 hours. The mixture was quenched with ice water and extracted three times with ethyl acetate. The combined extracts were dried with sodium sulfate, filtered and concentrated. The residue was purified by chromatography on silica gel to give the desired product (1.1 g, 97%). $^1$H NMR (CDCl$_3$) δ 10.40 (s, 1H), 7.20 (s, 2H), 3.00 (m, 2H), 1.4 (m, 3H). LC/MS: 235 (M+H)$^+$.

Step 3: 2-[2,6-dichloro-4-(ethylthio)phenyl]-3,8-dihydroimidazo[4,5-d]dipyrido[2,3-b:4',3'-f]azepine bis(trifluoroacetate)

A solution of (6Z)-5H-dipyrido[2,3-b:4',3'-f]azepine-5,6(11H)-dione 6-oxime trifluoroacetate (200 mg, 0.4 mmol), 2,6-dichloro-4-(ethylthio)benzaldehyde (200 mg, 0.85 mmol) and ammonium acetate (0.60 g, 8.0 mmol) were stirred in acetic acid (3 mL) and heated in a microwave for 5 minutes at 130° C. Evaporation gave the crude product which was dissolved in acetonitrile (1.0 mL) and triisopropyl phosphate (100 µL, 0.4 mmol) and heated in a microwave for 5 minutes at 180° C. Purification by preparative LCMS gave the desired product LC/MS: 440 (M+H)$^+$.

Preparation of Example A-135 and A-136

2-[2,6-dichloro-4-(ethylsulfinyl)phenyl]-3,8-dihydroimidazo[4,5-d]dipyrido[2,3-b:4',3'-f]azepine bis (trifluoroacetate) and 2-[2,6-dichloro-4- (ethylsulfonyl)phenyl]-3,8-dihydroimidazo[4,5-d]dipyrido[2,3-b:4',3'-f]azepine bis(trifluoroacetate)

A solution of 2-[2,6-dichloro-4-(ethylthio)phenyl]-3,8-dihydroimidazo[4,5-d]dipyrido[2,3-b:4',3'-f]azepine bis(trifluoroacetate) (70 mg, 0.105 mmol), m-chloroperbenzoic acid (14.4 mg, 0.084 mmol) and 1,4-dioxane (2 mL) was stirred at 25° C. for 15 minutes. The reaction mixture was diluted with methanol and purified by preparative LCMS to give the desired sulfoxide A-135 (27 mg, 38%) LC/MS: 456 (M+H)$^+$ and the desired sulfone A-136 (26 mg, 40%) LC/MS: 472 (M+H)$^+$.

Preparation of Example A-146

A solution of 3,5-dichloro-4-(3,8-dihydroimidazo[4,5-d]dipyrido[2,3-b:4',3'-f]azepin-2-yl)phenol (17.4 mg, 0.04 mmol), potassium carbonate (12 mg, 0.09 mmol) and bromoacetonitrile (8.8 µL, 0.13 mmol) in N,N-dimethylformamide (1.0 mL) was stirred at room temperature for 1 hour. Purification by preparative LCMS gave the desired product (11.6 mg, 40%). $^1$H NMR (DMSO-d$_6$): δ 8.60 (s, 1H), 8.10 (m, 1H), 8.00 (s, 1H), 7.92 (m, 1H), 7.60 (s, 1H), 7.50 (s, 2H), 6.85 (m, 1H), 5.35 (s, 2H). LC/MS: 435 (M+H)$^+$.

Preparation of Example A-158

2-(3,8-dihydroimidazo[4,5-d]dipyrido[2,3-b:4',3'-f]azepin-2-yl)isophthalonitrile dihydrochloride A solution of 2-(2,6-dichlorophenyl)-3,8-dihydroimidazo[4,5-d]dipyrido[2,3-b:4',3'-f]azepine hydrochloride (4.0 g, 9.6 mmol) and copper cyanide (4.3 g, 48 mmol) in N-methylpyrrolidinone (200 mL) was heated in the microwave at 230° C. for 60 min. The reaction mixture was added to a 5% solution of [10% solution of NH$_4$Cl in 30% NH$_4$OH] in water (200 mL per 20 mL reaction). The aqueous layer was neutralized with concentrated HCl (~8 mL per 20 mL reaction) and the precipitate was collected. This crude solid was purified as A first pass through a large capacity C18 reverse phase column. A second purication by preparative LCMS gave the desired product as a TFA salt. The product was dissolved in acetonitrile and treated with saturated sodium bicarbonate. The free base, which precipitated from the solution, was collected, dissolved in 0.1 N HCl and acetonitrile, and lyophilized to give the desired dihydrochloride salt (600 mg, 14%) as a red solid. $^1$H NMR (300 MHz, CD$_3$OD): δ 8.27-

8.19 (m, 3 H), 8.09-8.04 (m, 2 H), 8.00 (d, J=6.2 Hz, 1 H), 7.93-7.83 (m, 2 H), 7.07 (dd, J=7.6, 5.3 Hz, 1 H); MF=$C_{21}H_{13}Cl_2N_7$; LCMS calculated for $C_{21}H_{12}N_7(M+H)^+$: m/z=362.1.

Preparation of Example A-162

3Chloro-2-(3,8-dihydroimidazo[4,5-d]dipyrido[2,3-b:4',3'-f]azepin-2-yl)benzonitrile dihydrochloride A solution of 2-(2,6-dichlorophenyl)-3,8-dihydroimidazo[4,5-d]dipyrido[2,3-b:4',3'-f]azepine hydrochloride (4.0 g, 9.6 mmol) and copper cyanide (4.3 g, 48 mmol) in N-methylpyrrolidinone (200 mL) was heated in the microwave at 230° C. for 30 min. Purification by preparative LCMS gave the desired product as a TFA salt. The product was dissolved in acetonitrile and treated with saturated sodium bicarbonate. The free base, which precipitated from the solution, was collected, dissolved in 1.0 N HCl and acetonitrile, and lyophilized to give the desired dihydrochloride salt (580 mg, 14%) as a red/orange solid. $^1$H NMR (300 MHz, $CD_3OD$): δ 8.18 (d, J=6.2 Hz, 1 H), 8.08-8.05 (m, 2 H), 7.98-7.92 (m,3 H), 7.80 (dd, J=7.6, 1.5 Hz, 1 H); 7.74 (dd, J=8.2, 7.9 Hz, 1 H), 7.04 (dd, J=7.6, 5.0 Hz, 1 H); MF=$C_{20}H_{13}Cl_3N_6$; LCMS calculated for $C_{20}H_{12}ClN_6(M+H)^+$: m/z=371.1.

Preparation of Example A-170

Step 1: tert-butyl (4-formylpyridin-3-yl)carbamate

A solution of tert-butyl pyridin-3-ylcarbamate (17.7 g, 91.1 mmol) in THF (300 mL) was cooled to −78° C. and treated with 1.70 M tert-butyllithium in pentane (129 mL). Upon completion of the addition, the reaction was stirred at −78° C. for an additional 15 min and then at −20° C. for 1.5 h. 1-piperidinecarboxaldehyde (30.4 mL, 0.273 mol) was added while the temperature was maintained below at −15° C., and then the mixture was allowed to stir at room temperature overnight. The solution was cooled to 0° C. and was quenched by the addition of 1 M HCl to bring the pH to 2. Solid $Na_2CO_3$ was then added to adjust the pH to 7. The solution was extracted with ethyl acetate three times, and the combined organic solutions were washed with water (3×) and brine. The organic layer was dried, filtered, and volatiles evaporated. The residue was purified by silica gel chromatography (50% ethyl acetate/hexanes) to give the desired product as a yellow solid (12.2 g, 60%). LCMS for $C_{11}H_{15}N_2O_3(M+H)^+$: m/z=223.1.

Step 2: tert-butyl [4-(3-hydroxy-3,8-dihydroimidazo[4,5-d]dipyrido[2,3-b:4',3'-f]azepin-2-yl)pyridin-3-yl]carbamate A mixture of (6Z)-5H-dipyrido[2,3-b:4',3'-f]azepine-5,6(11H)-dione 6-oxime (80.0 mg, 0.333 mmol), tert-butyl-(4fprmylpyridin-3yl)carbamate lammonium acetate (0.513 g, 6.66 mmol), water (0.12 mL) and acetic acid (0.76 mL) was stirred at 80° C. for 3 h. The solution was diluted with ethyl acetate and water, the organic solution was washed with brine, dried over $MgSO_4$ and concentrated. The crude residue was purified by preparative LCMS to yield the desired product (102 mg, 69%). LCMS for $C_{23}H_{22}N_7O_3(M+H)^+$: m/z=444.2.

Preparation of Example A-171

Step 1: 4-bromo-3,5-dimethylpyridine 1-oxide

To a solution of 3,5-dimethylpyridine 1-oxide (6.1 g, 50 mmol) in acetic acid (30 mL) was added thallium(III) triacetate (5.0 g, 13 mmol) and bromine (2.6 mL, 50 mmol). The resulting solution was heated at 60° C. overnight. The reaction was concentrated in vacuo, diluted with water and ethyl acetate. The organic layer was concentrated and residue was purified by silica gel chromatography to afford the desired product (5.40 g, 54%). $^1$H NMR (400 MHz, $CDCl_3$): δ 7.96 (s, 2 H), 2.38 (s, 6 H).

Step 2: 4-bromo-3,5-dimethylpyridine

To a microwave tube was added 4-bromo-3,5-dimethylpyridine 1-oxide (2.00 g, 9.90 mmol), triphenylphosphine (3.12 g, 11.9 mmol) and toluene (10 mL). The tube was sealed and heated at 180° C. overnight. The reaction solution was diluted with ethyl acetate, and filtered. The filtrate was concentrated and purified by flash chromatography (10% to 40% ethyl acetate in hexanes) to afford the desired product as a yellow oil (700 mg, 38%). $^1$H NMR (400 MHz, $CDCl_3$): δ 8.22 (s, 2 H), 2.38 (s, 6 H); LCMS calculated for $C_7H_9BrN(M+H)^+$: m/z=186.0.

Step 3: 3,5-dimethylisonicotinaldehyde

A solution of 4-bromo-3,5-dimethylpyridine (0.70 g, 3.76 mmol) in ether (10 mL) was cooled to −78° C. and then 2.50 M n-butyllithium in hexane (1.50 mL) was added to the reaction flask dropwise. After stirring at −78° C. for 1 h, DMF (1.75 mL, 22.6 mmol) was added to the reaction flask slowly. The reaction solution was allowed to warm to room temperature overnight. The reaction was quenched with 10 mL saturated $NH_4Cl$ solution and diluted with ethyl acetate. The aqueous layer was extracted with ethyl acetate once. The combined organic solutions were dried over $Na_2SO_4$, filtered and concentrated. The residue was purified by silica gel chromatography (40% to 50% ethyl acetate/hexanes) to afford the desired product as a solid. (280 mg, 55%). $^1$H NMR (400 MHz, $CDCl_3$): δ 10.62 (s, 1 H), 8.43 (s, 2 H), 2.57 (s, 6 H).

Step 4: 2-(3,5-dimethylpyridin-4-yl)-3,8-dihydroimidazo[4,5-d]dipyrido[2,3-b:4',3'-f]azepine 6(Z)-5H-dipyrido[2,3-b:4',3'-f]azepine-5,6(11H)-dione 6-oxime (23.0 mg, 0.0957 mmol) 3,5-dimethylisonicotinaldehyde (38.8 mg, 0.287 mmol) ammonium acetate (110 mg, 1.4 mmol) acetic acid (2 mL) were heated at 130° C. for 5 min in a microwave. The acetic acid was evaporated and the residue was stirred in acetonitrile (3 mL) and triisopropyl phosphite (88 μL, 0.38 mmol) was added. The brown solution was heated at 180° C. for 5 min in the microwave. The mixture was purified with preparative LCMS to give the desired product. (20 mg, 61%). LCMS for $C_{20}H_{12}N_6(M+H)^+$: m/z=341.1.

Preparation of Example A-172

Step 1: (3,5-dichlorophenoxy)(triisopropyl)silane

To a solution of 3,5-dichloro-phenol (5.9 g, 36 mmol) in methylene chloride (50 mL,) was added 2,6-lutidine (8.38 mL, 72.4 mmol) and triisopropylsilyl triflate (9.7 mL, 36 mmol) at 0° C. The resulting mixture was stirred at 0° C. for 4 h. The reaction was quenched with 0.1 N HCl and diluted with ethyl acetate. The organic solution was washed with brine, dried over $Na_2SO_4$ and concentrated in vacuo. The residue was purified with flash chromatography (5% ethyl acetate/hexanes) to give the desired product as a colorless oil (10.5 g, 91%). $^1$H NMR (400 MHz, CDCl$_3$): δ 6.95 (t, J=1.8 Hz, 1 H), 6.76 (d, J=1.8 Hz, 2 H), 1.26 (m, 3 H), 1.09 (d, J=7.0 Hz, 18 H).

Step 2: 2,6-dichloro-4-hydroxybenzaldehyde

A solution of 2.50 M n-butyllithium in hexane (13.3 mL) was added to a stirred solution of (3,5-dichlorophenoxy)(triisopropyl)silane (10.1 g, 31.6 mmol) in THF (40 mL) under an atmosphere of nitrogen at −78° C. After stirring for 45 min at −78° C., DMF (5 mL) was added slowly. The mixture was allowed to warm to −10° C. After hydrolysis with 2 N HCl, the layers were separated and the aqueous layer separated and extracted with ethyl acetate twice. The combined organic solutions were dried over Na$_2$SO$_4$, filtered and concentrated. To the residue was added hexane (30 mL) and the precipitate was filtered and washed with hexane to give the desired product as a white precipitate. (5.50 g, 91%). LCMS for C$_7$H$_5$Cl$_2$O$_2$(M+H)$^+$: m/z=191.

Step 3: 3,5-dichloro-4-(3,8-dihydroimidazo[4,5-d]dipyrido[2,3-b:4',3'-f]azepin-2-yl)phenol 6Z)-5H-dipyrido[2,3-b:4',3'-f]azepine-5,6(11H)-dione 6-oxime (26.0 mg, 0.108 mmol) 2,6-dichloro-4-hydroxybenzaldehyde (62.0 mg, 0.325 mmol) ammonium acetate (120 mg, 1.6 mmol) acetic acid (2 mL) were heated at 130° C. for 5 min in a microwave. The acetic acid was evaporated and the residue was stirred in acetonitrile (3 mL) and triisopropyl phosphite (100 µL, 0.43 mmol) was added. The brown solutions were heated at 180° C. for 5 min. in a microwave. The solution was purified with preparative LCMS to give the desired product (15 mg, 35%). LCMS for C$_{19}$H$_{12}$Cl$_2$N$_5$O (M+H)$^+$: m/z=396.

Preparation of Example A-173

Step 1: 2,6-dichloro-4-methoxybenzaldehyde

To a solution of 2,6-dichloro-4-hydroxybenzaldehyde (225 mg, 1.18 mmol) in DMF (2.0 mL) was added potassium carbonate (0.81 g, 5.9 mmol) and methyl iodide (1.47 mL, 23.6 mmol). The resulting mixture was heated at 80° C. for 3 h. Reaction was diluted with water and ethyl acetate. The organic layer was separated and dried over Na$_2$SO$_4$, filtered and concentrated. The residue was purified by flash chromatography (20% ethyl acetate/hex) to give the desired product as a white solid (210 mg, 87%). LCMS for C$_8$H$_7$Cl$_2$O$_2$(M+H)$^+$: m/z=205.

Step 2: 2-(2,6-dichloro-4-methoxyphenyl)-3,8-dihydroimidazo[4,5-d]dipyrido[2,3-b:4',3'-f]azepine bis(trifluoroacetate)

This compound was prepared according to the procedure of Example A-98, steps 3 and 4 using (6Z)-5h-dipyrido[2,3-b:4',3'-f]azepine-5,6(11h)-dione 6-oxime and 2,6-dichloro-4-methoxybenzaldehyde as the starting materials. LCMS calculated for C$_{20}$H$_{13}$C$_{12}$N$_5$O (M+H)$^+$: m/z=410.1.

Preparation of Example A-175

This compound was prepared according to the procedure for preparing Example A-98 Step 3 and 4 using (6E)-5 H-dipyrido[2,3-b:3',4'-f]azepine-5,6(11 H)-dione 6-oxime and 2,6-dichloro-4-isopropoxy-benzaldehyde as the starting materials. LCMS for C$_{22}$H$_{18}$Cl$_2$N$_5$O (M+H)$^+$: m/z=438.1.

Preparation of Example A-176

Step 1: 1,3-dichloro-2-iodo-5-(trifluoromethoxy)benzene 2,6-Dichloro-4-(trifluoromethoxy)aniline (4.65 g, 13.2 mmol) suspended in 1 M of HCl solution (100 mL) was treated at 0° C. with sodium nitrite (0.913 g, 13.2 mmol) in water dropwise. After 15 minutes at 0° C., potassium iodide (2.20 g, 13.2 mmol) in water was added and the solution was heated at 40° C. for 15 min. The solution was quenched with saturated aq. Na$_2$S$_2$O$_3$ solution (100 mL), and extracted with ethyl acetate (300 mL). The organic phase was washed with 0.1 N HCl solution satd. aq. NaHCO$_3$ sol. (500 mL), and dried over sodium sulfate. Purification by silica gel chromatography (10-40% EtOAc/hexanes) afforded the desired product as a yellow solid.

Step 2: 2,6-dichloro-4-(trifluoromethoxy)benzaldehyde

This compound was prepared according to the procedure for Example A-98, Step 2 using 1,3-dichloro-2-iodo-5-(trifluoromethoxy)benzene as a starting material. LCMS for C$_8$H$_4$Cl$_2$F$_3$O$_2$(M+H)$^+$: m/z=259.

Step 3: 2-[2,6-dichloro-4-(trifluoromethoxy)phenyl]-3,8-dihydroimidazo[4,5-d]dipyrido[2,3-b:4',3'-f]azepine bis(trifluoroacetate)

This compound was prepared according to the procedure of Example A-98, Steps 3 and 4 using (6Z)-5H-dipyrido[2,3-b:4',3'-f]azepine-5,6(11 H)-dione 6oxime and 2,6-dichloro-4-(trifluoromethoxy)benzaldehyde as the starting materials. LCMS for C$_{20}$H$_{11}$C$_{12}$F$_3$N$_5$O (M+H-2TFA)$^+$: m/z=464.0.

Preparation of Example A-188

2-(2,6-Dichloro-4-methoxyphenyl)-3,8-dihydroimidazo[4,5-d]dipyrido[2,3-b:4',3'-f]azepine bis(trifluoroacetate) (51.0 mg, 0.0799 mmol), zinc cyanide (93.8 mg, 0.799 mmol), tris(dibenzylideneacetone)dipalladium(0) (18 mg, 0.020 mmol), [1,1'-bis(diphenylphosphino)ferrocene]dichloropalladium(II), complex with dichloromethane (1:1) (16 mg, 0.020 mmol) were dissolved in DMF (1.0 mL) and the solution was degassed. The reaction was stirred in a microwave for 15 min at 190° C. The reaction was diluted with methanol, filtered and purified by preparative LCMS to give the desired product (15 mg, 48%). LCMS calculated for C$_{22}$H$_{14}$N$_7$O(M+H)$^+$: m/z=392.1.

Preparation of Example A-192

This compound was prepared according to the procedure of Example A-188 using 2-(2,6-dichloro-4-isopropoxyphenyl)-3,8-dihydroimidazo[4,5-d]dipyrido[2,3-b:3',4'-f]azepine bis(trifluoroacetate) as the starting material. LCMS for C$_{24}$H$_{18}$N$_7$O(M+H)$^+$: m/z=420.1.

Preparation of Example 186

Intermediate E-1: 6-[(Dimethylamino)methylene]-6,11-dihydro-5H-dipyrido[2,3-b:3',4'-f]azepin-5-one A solution of 6,11-dihydro-5H-dipyrido[2,3-b:3',4'-f]azepin-5-one (0.440 g, 2.08 mmol, Intermediate D-6) and 1,1-dimethoxy-N,N-dimethylmethanamine (2.49 mL, 18.7 mmol) in THF (30 mL) was stirred for three days under an atmosphere of nitrogen. The mixture was concentrated in vacuo to give the desired product as an orange solid which was used directly for the next step. LC/MS: 267 (M+H)$^+$.

Product (Example 186):2-(2,6-Dichlorophenyl)-2,8-dihydropyrazolo[3,4-d]dipyrido[2,3-b:3',4'-f]azepine (2,6-Dichlorophenyl)hydrazine hydrochloride (168 mg, 0.788 mmol) was added to a solution of 6-[(dimethylamino)methylene]-6,11-dihydro-5H-dipyrido[2,3-b:3',4'-f]azepin-5-one (105 mg, 0.394 mmol, Intermediate E-1) in ethanol (4 mL) and stirred at room temperature. After 30 minutes, the mixture was heated to 60° C. overnight. The reaction was then cooled to room temperature and the major product from the reaction mixture was isolated using preparative LC/MS to provide the desired product as a white powder. $^1$H NMR (DMSO-d$_6$) δ 8.77 (bs, 1H), 8.45 (bs, 1H), 8.40 (bs, 1H), 8.04 (m, 2H), 7.94 (d, 1H), 7.75 (m, 2H), 7.62 (m, 1H), 6.95 (m, 1H), 6.87 (m, 1H). LC/MS: 380 (M+H)$^+$.

Example A

In vitro JAK Kinase Assay

Compounds herein were tested for inhibitory activity of Jak targets according to the following in vitro assay described in Park et al., *Analytical Biochemistry* 1999, 269, 94-104. The catalytic domains of human Jak1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). IC$_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/mL (0.01%) BSA. The ATP concentration in the reactions was 90 μM for Jak1, 30 μM for Jak2 and 3 μM for Jak3. Reactions were carried out at room temperature for 1 hr and then stopped with 20 μL 45 mM EDTA, 300 nM SA-APC, 6 nM Eu—Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). Compounds having an IC$_{50}$ of 10 μM or less for any of the above-mentioned Jak targets were considered active.

Example B

Cellular Assays

One or more compounds herein were tested for inhibitory activity of Jak targets according to at least one of the following cellular assays.

Cancer cell lines dependent on cytokines and hence Jak/STAT signal transduction, for growth, were plated at 6000 cells per well (96 well plate format) in RPMI 1640, 10% Free BaseS, and 1 nG/mL of appropriate cytokine. Compounds were added to the cells in DMSO/media (final concentration 0.2% DMSO) and incubated for 72 hours at 37° C., 5% CO$_2$. The effect of compound on cell viability was assessed using the CellTiter-Glo Luminescent Cell Viability Assay (Promega) followed by TopCount (Perkin Elmer, Boston, Mass.) quantitation. Potential off-target effects of compounds were measured in parallel using a non-Jak driven cell line with the same assay readout. Compounds having an IC$_{50}$ of 10 μM or less with selectivity for Jak driven proliferation were considered active. All experiments were performed in duplicate.

The above cell lines can also be used to examine the effects of compounds on phoshporylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein have been or can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 μg/ml streptomycin) at a density of 2×10$^6$ cells/ml at 37° C. for up to 2 days. For IL-2 stimulated cell proliferation analysis, T-cells are first treated with Phytohemagglutinin (PHA) at a final concentration of 10 μg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. Hematol J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting Jak targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFree Base). On day 5, ears are measured for thickness using an engineer's micrometer. This measurement is recorded and used as a baseline. Both of the animals' ears are then challenged by a topical application of DNFree Base in a total of 20 µL (10 µL on the internal pinna and 10 µL on the external pinna) at a concentration of 0.2%. Twenty-four to seventy-two hours after the challenge, ears are measured again. Treatment with the test compounds was given throughout the sensitization and challenge phases (day −1 to day 7) or prior to and throughout the challenge phase (usually afternoon of day 4 to day 7). Treatment of the test compounds (in different concentration) was administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the Jak-STAT pathways) of the test compounds can be confirmed by immunohistochemical analysis. Activation of the Jak-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be or have been evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; Methods in Molecular Biology: Vol. 225, Inflammation Protocols., Winyard, P. G. and Willoughby, D. A., Humana Press, 2003.).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A method of treating a disease associated with JAK activity in a patient, wherein said disease is allograft rejection, graft versus host disease, rheumatoid arthritis, psoriasis, polycythemia vera (PV), essential thrombocythemia (ET), or myeloid metaplasia with myelofibrosis, comprising administering to said patient a therapeutically effective amount of a compound of Formula Ia, Ib, or Ic:

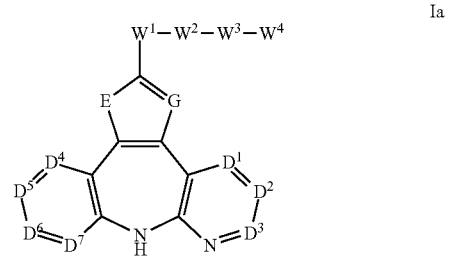

Ia

-continued

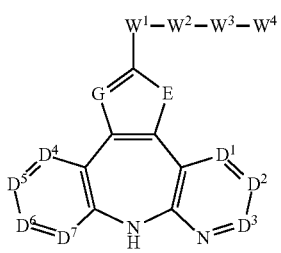
Ib

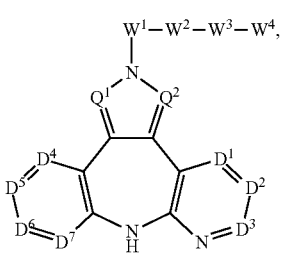
Ic or a pharmaceutically acceptable salt thereof, wherein:

$D^1$, $D^2$, $D^3$, $D^4$, $D^5$, $D^6$ and $D^7$ are, independently, $CR^1$ or N;

E is O, S, SO, $SO_2$, or $NR^{2a}$;

G is N or $CR^{2b}$;

$Q^1$ and $Q^2$ are each, independently, N or $CR^{2c}$;

$W^1$ is absent, $C_{1-6}$ alkyl, $C_{2-6}$ alkenyl, $C_{2-6}$ alkynyl, O, S, $NR^3$, CO, COO, $CONR^3$, SO, $SO_2$, $SONR^3$, $SO_2NR^3$, or $NR^3CONR^4$, wherein said $C_{1-6}$ alkyl, $C_{2-6}$ alkenyl or $C_{2-6}$ alkynyl is optionally substituted by 1, 2 or 3 substituents independently selected from halo, OH, $C_{1-4}$ alkoxy, $C_{1-4}$ haloalkoxy, amino, $C_{1-4}$ alkylamino and $C_{2-8}$ dialkylamino;

$W^2$ is absent, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2, or 3 substituents independently selected from halo, CN, $NO_2$, OH, =NH, =NOH, =NO—($C_{1-4}$ alkyl), —$NR^3C(O)O$—($C_{1-4}$ alkyl), $NR^3C(O)$—($C_{1-4}$ alkyl), —$C(O)O$—($C_{1-4}$ alkyl), $C_{1-4}$ haloalkyl, $C_{1-4}$ cyanoalkyl, pentahalosulfanyl, $C_{1-4}$ hydroxylalkyl, $C_{1-4}$ alkylthio, $C_{1-4}$ haloalkylthio, $C_{1-4}$ alkoxy, $C_{1-4}$ haloalkoxy, amino, $C_{1-4}$ alkylamino and $C_{2-8}$ dialkylamino;

$W^3$ is absent, $C_{1-6}$ alkyl, $C_{2-6}$ alkenyl, $C_{2-6}$ alkynyl, O, S, $NR^3$, =N—, =N—O—, =N—O—($C_{1-4}$ alkyl)-, O—($C_{1-4}$ alkyl), S—($C_{1-4}$ alkyl), $NR^3$—($C_{1-4}$ alkyl), ($C_{1-4}$ alkyl)-O—($C_{1-4}$ alkyl), ($C_{1-4}$ alkyl)-S—($C_{1-4}$ alkyl), ($C_{1-4}$ alkyl)-$NR^3$—($C_{1-4}$ alkyl), CO, COO, C(O)—($C_{1-4}$ alkyl), C(O)O—($C_{1-4}$ alkyl), C(O)—($C_{1-4}$ alkyl)-C(O), $NR^3C(O)$—($C_{1-4}$ alkyl), $C(O)NR^3$—($C_{1-4}$ alkyl), $NR^3C(O)O$—($C_{1-4}$ alkyl), $NR^3C(O)O$, $CONR^3$, SO, $SO_2$, $SONR^3$, $SO_2NR^3$, or $NR^3CONR^4$, wherein said $C_{1-6}$ alkyl, $C_{2-6}$ alkenyl or $C_{2-6}$ alkynyl is optionally substituted by 1, 2 or 3 substituents independently selected from halo, OH, CN, $C_{1-4}$ alkoxy, $C_{1-4}$ haloalkoxy, amino, $C_{1-4}$ alkylamino and $C_{2-8}$ dialkylamino;

$W^4$ is H, $NR^3R^4$, CN, $C_{1-6}$ alkyl, $C_{2-6}$ alkenyl, $C_{2-6}$ alkynyl, aryl, cycloalkyl, heteroaryl or heterocycloalkyl, wherein each of said $C_{1-6}$ alkyl, $C_{2-6}$ alkenyl, $C_{2-6}$ alkynyl, aryl, cycloalkyl, heteroaryl or heterocycloalkyl is optionally substituted by 1, 2, 3, 4 or 5 substituents independently selected from halo, OH, CN, $C_{1-4}$ alkoxy, =NH, =NOH, =NO—($C_{1-4}$ alkyl), $C_{1-4}$ haloalkyl, $C_{1-4}$ haloalkoxy, pentahalosulfanyl, COOH, $CONH_2$, COO—($C_{1-4}$ alkyl), amino, $C_{1-4}$ alkylamino and $C_{2-8}$ dialkylamino;

$R^1$ is, independently, H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $NR^cC(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $NR^cS(O)NR^cR^d$, pentahalosulfanyl, $S(O)_2R^b$, or $S(O)_2NR^cR^d$;

$R^{2a}$ is H, $C_{1-4}$ alkyl, $C_{2-4}$ alkenyl, $C_{2-4}$ alkynyl, OH, $C_{1-4}$ alkoxy, $C(O)R^b$, $C(O)NR^cR^d$, $S(O)R^b$, $S(O)NR^cR^d$, $S(O)_2R^b$, or $S(O)_2NR^cR^d$;

$R^{2b}$ and $R^{2c}$ are each, independently, H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cC(O)NR^cR^d$, $NR^cR^d$, $NR^cC(O)R^d$, $NR^cC(O)OR^a$, $S(O)R^b$, $S(O)NR^cR^d$, $NR^cS(O)NR^cR^d$, $S(O)_2R^b$, or $S(O)_2NR^cR^d$;

$R^3$ and $R^4$ are each, independently, H, $C_{1-6}$ alkyl, $C_{2-6}$ alkenyl, $C_{2-6}$ alkynyl, aryl, cycloalkyl, arylalkyl, cycloalkylalkyl, $COOR^{a'}$, $COR^{b'}$, $SOR^{b'}$, or $SO_2R^{b'}$ wherein each of said $C_{1-6}$ alkyl, $C_{2-6}$ alkenyl, $C_{2-6}$ alkynyl, aryl, cycloalkyl, arylalkyl, or cycloalkylalkyl is optionally substituted by 1, 2 or 3 substituents selected from halo, $C_{1-4}$ alkyl, $C_{1-4}$ haloalkyl, OH, $C_{1-4}$ alkoxy, $C_{1-4}$ haloalkoxy, amino, $C_{1-4}$ alkylamino, $C_{2-8}$ dialkylamino, aminocarbonyl, $C_{1-4}$ alkylaminocarbonyl, $C_{2-8}$ dialkylaminocarbonyl, CN and $NO_2$;

or $R^3$ and $R^4$ together with the N atom to which they are attached form a heterocycloalkyl group optionally substituted by 1, 2 or 3 substituents selected from halo, $C_{1-4}$ alkyl, $C_{1-4}$ haloalkyl, OH, $C_{1-4}$ alkoxy, $C_{1-4}$ haloalkoxy, amino, $C_{1-4}$ alkylamino, $C_{2-8}$ dialkylamino, aminocarbonyl, $C_{1-4}$ alkylaminocarbonyl, and $C_{2-8}$ dialkylaminocarbonyl;

$R^a$ and $R^{a'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$ and $R^{b'}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; and $R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

provided that when $D^7$ is N, E is O or S, and G is N; then -$W^1$-$W^2$-$W^3$-$W^4$ is other than H.

2. The method of claim 1, wherein the compound is a compound having Formula Ia, or a pharmaceutically acceptable salt thereof.

3. The method of claim 1, wherein the compound is a compound having Formula Ib, or pharmaceutically acceptable salt thereof.

4. The method of claim 1, wherein the compound is a compound having Formula Ic, or pharmaceutically acceptable salt thereof.

5. The method of claim 1, wherein E is $NR^{2a}$.

6. The method of claim 1, wherein E is NH or NOH.

7. The method of claim 1, wherein G is N.

8. The method of claim 1, wherein E is NH or NOH and G is N.

9. The method of claim 1, wherein E is NH and G is N.

10. The method of claim 1, wherein the compound is a compound having Formula Ia, or a pharmaceutically acceptable salt thereof, wherein:
E is NH or NOH; and
G is N.

11. The method of claim 1, wherein $Q^1$ is N and $Q^2$ is $CR^{2c}$.

12. The method of claim 1, wherein $Q^1$ is $CR^{2c}$ and $Q^2$ is N.

13. The method of claim 1, wherein each of $D^1$, $D^2$, and $D^3$ is $CR^1$.

14. The method of claim 1, wherein each of $D^1$, $D^2$, and $D^3$ is CH.

15. The method of claim 1, wherein each of $D^4$, $D^5$, $D^6$, and $D^7$ is $CR^1$.

16. The method of claim 1, wherein each of $D^4$, $D^5$, and $D^7$ is $CR^1$ and $D^6$ is N.

17. The method of claim 1, wherein each of $D^4$ and $D^7$ is CH.

18. The method of claim 1, wherein $D^5$ is $CR^1$ and $R^1$ is H or halo.

19. The method of claim 1, wherein $D^6$ is $CR^1$ and $R^1$ is halo.

20. The method of claim 1, wherein $D^6$ is CF.

21. The method of claim 1, wherein $D^6$ is N.

22. The method of claim 1, wherein $D^5$ is CH or CF.

23. The method of claim 1, wherein $-W^1-W^2-W^3-W^4$ is $C_{1-6}$ alkyl, aryl, arylalkyl, cycloalkyl, cycloalkylalkyl, heteroaryl, heteroarylalkyl, heterocycloalkyl or heterocycloalkylalkyl, each optionally substituted by 1, 2, or 3 halo, $C_{1-4}$ alkyl, $C_{1-4}$ haloalkyl, $C_{1-4}$ haloalkylcarbonyl, aryl, cycloalkyl, heteroaryl, heterocycloalkyl, —COOH, —COO—($C_{1-4}$ alkyl), OH, $C_{1-4}$ alkoxy, $C_{1-4}$ haloalkoxy, hydroxyalkyl, CN, cyanoalkyl, alkylthio, arylthio, haloalkylthio, alkylsulfinyl, alkylsulfonyl, arylsulfinyl, arylsulfonyl, aryloxy, cycloalkyloxy, arylalkyloxy, aminocarbonyl, aminocarbonylalkyl, cyanoalkylcarbonyl, formyl, alkylcarbonyl, amino, alkylamino, alkylcarbonylamino, alkyloxycarbonylamino, or dialkylamino optionally substituted by CN.

24. The method of claim 1, wherein $-W^1-W^2-W^3-W^4$ is $C_{1-6}$ alkyl, aryl, arylalkyl, cycloalkyl, heteroaryl, heterocycloalkyl, or heterocycloalkylalkyl, each optionally substituted by 1, 2, or 3 halo, $C_{1-4}$ alkyl, $C_{1-4}$ haloalkyl, $C_{1-4}$ haloalkylcarbonyl, aryl, —COO—($C_{1-4}$ alkyl), OH, $C_{1-4}$ alkoxy, $C_{1-4}$ haloalkoxy, hydroxyalkyl, CN, cyanoalkyl, alkylthio, haloalkylthio, alkylsulfinyl, alkylsulfonyl, aryloxy, aminocarbonyl, aminocarbonylalkyl, cyanoalkylcarbonyl, formyl, alkylcarbonyl, alkyloxycarbonylamino, alkylcarbonylamino, or dialkylamino optionally substituted by CN.

25. The method of claim 1, wherein $-W^1-W^2-W^3-W^4$ is methyl, ethyl, propyl, butyl, pentyl, hexyl, phenyl, naphthyl, biphenyl, benzyl, phenylethyl, phenylpropyl, cyclopropyl, cyclohexyl, cyclohexenyl, bicyclo[2.2.1]hept-2-enyl, cyclopentyl, pyridyl, pyrryl, imidazolyl, isoxazolyl, thiazolyl, quinolinyl, piperidinyl, tetrahydrofuranyl, pyrrolidinyl, benzo[1,3]dioxolyl, (piperidin-4-yl)methyl, (piperidin-3-yl)methyl, (tetrahydropyran-4-yl)-methyl, (tetrahydrothiopyran-4-yl)-methyl, each optionally substituted by 1, 2, or 3 halo, $C_{1-4}$ alkyl, $C_{1-4}$ haloalkyl, $C_{1-4}$ haloalkylcarbonyl, aryl, —COO—($C_{1-4}$ alkyl), OH, $C_{1-4}$ alkoxy, $C_{1-4}$ haloalkoxy, hydroxyalkyl, CN, cyanoalkyl, cyanoalkylcarbonyl, alkylthio, haloalkylthio, alkylsulfinyl, alkylsulfonyl, arylalkyloxy, aminocarbonyl, aminocarbonylalkyl, cyanoalkylcarbonyl, formyl, alkylcarbonyl, alkyloxycarbonylamino, alkylcarbonylamino, or dialkylamino optionally substituted by CN.

26. The method of claim 1, wherein $-W^1-W^2-W^3-W^4$ is phenyl, pyrazyl, pyrindyl, pyrryl, indolyl, furyl, thienyl, or benzothienyl, each optionally substituted by 1, 2, 3, 4, or 5 halo, $C_{1-4}$ alkyl, $C_{1-4}$ haloalkyl, aryl, OH, $C_{1-4}$ alkoxy, hydroxyalkyl, CN, cyanoalkyl, alkylthio, haloalkylthio, alkylsulfinyl, alkylsulfonyl, cycloalkyl, heterocycloalkyl, cycloalkylalkyl, heterocyclyoalkylalkyl, amino, dialkylamino, aminoalkyl, or aminosulfonyl.

27. The method of claim 1, wherein $-W^1-W^2-W^3-W^4$ is phenyl optionally substituted by 1, 2, 3, 4, or 5 halo, $C_{1-4}$ alkyl, $C_{1-4}$ haloalkyl, aryl, OH, $C_{1-4}$ alkoxy, hydroxyalkyl, CN, cyanoalkyl, alkylthio, haloalkylthio, alkylsulfinyl, alkylsulfonyl, cycloalkyl, heterocycloalkyl, cycloalkylalkyl, heterocyclyoalkylalkyl, amino, dialkylamino, aminoalkyl, or aminosulfonyl.

28. The method of claim 1, wherein $-W^1-W^2-W^3-W^4$ is phenyl optionally substituted by 1, 2, 3, 4, or 5 halo, $C_{1-4}$ alkyl, $C_{1-4}$ haloalkyl, aryl, OH, $C_{1-4}$ alkoxy, CN, cyanoalkyl, alkylthio, or amino.

29. The method of claim 1, wherein the compound is a compound having Formula IIa or IIb:

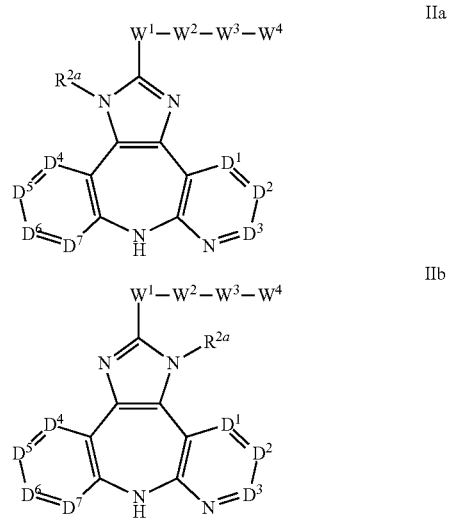

or pharmaceutically acceptable salt thereof.

30. The method of claim 1, wherein the compound is selected from:
2-tert-butyl-10-fluoro-3,8-dihydroimidazo[4,5-d]pyrido[2,3-b][1]benzazepine;
2-cyclopropyl-10-fluoro-3,8-dihydroimidazo[4,5-d]pyrido[2,3-b][1]benzazepine;
2-cyclohexyl-10-fluoro-3,8-dihydroimidazo[4,5-d]pyrido[2,3-b][1]benzazepine;
10-fluoro-2-isobutyl-3,8-dihydroimidazo[4,5-d]pyrido[2,3-b][1]benzazepine;
2-cyclopentyl-10-fluoro-3,8-dihydroimidazo[4,5-d]pyrido[2,3-b][1]benzazepine;
10-fluoro-2-(tetrahydrofuran-3-yl)-3,8-dihydroimidazo[4,5-d]pyrido[2,3-b][1]benzazepine;
2-cyclohex-3-en-1-yl-10-fluoro-3,8-dihydroimidazo[4,5-d]pyrido[2,3-b][1]benzazepine;
Trans ethyl (1R,S)-2-(10-fluoro-3,8-dihydroimidazo[4,5-d]pyrido[2,3-b][1]benzazepin-2-yl)cyclopropanecarboxylate;
2-bicyclo[2.2.1]hept-5-en-2-yl-10-fluoro-3,8-dihydroimidazo[4,5-d]pyrido[2,3-b][1]benzazepine;

[(1S)-2-(10-fluoro-3,8-dihydroimidazo[4,5-d]pyrido[2,3-b][1]benzazepin-2-yl)cyclopropyl]methanol;
2-(1-ethylpentyl)-10-fluoro-3,8-dihydroimidazo[4,5-d]pyrido[2,3-b][1]benzazepine;
4-ethyl-4-(10-fluoro-3,8-dihydroimidazo[4,5-d]pyrido[2,3-b][1]benzazepin-2-yl)hexanenitrile;
2-cyclopentyl-10,11-difluoro-3,8-dihydroimidazo[4,5-d]pyrido[2,3-b][1]benzazepine;
2-(1-ethylpentyl)-10,11-difluoro-3,8-dihydroimidazo[4,5-d]pyrido[2,3-b][1]benzazepine;
3-[1-(10-fluoro-3,8-dihydroimidazo[4,5-d]pyrido[2,3-b][1]benzazepin-2-yl)cyclohexyl]propanenitrile;
4-(10-fluoro-3,8-dihydroimidazo[4,5-d]pyrido[2,3-b][1]benzazepin-2-yl)-4-methylpentanenitrile;
2-(1-ethylpropyl)-10-fluoro-3,8-dihydroimidazo[4,5-d]pyrido[2,3-b][1]benzazepine;
10-fluoro-2-[2-(methylthio)ethyl]-3,8-dihydroimidazo[4,5-d]pyrido[2,3-b][1]benzazepine;
10-fluoro-2-[2-(methylsulfinyl)ethyl]-3,8-dihydroimidazo[4,5-d]pyrido[2,3-b][1]benzazepine;
2-[(benzyloxy)methyl]-10-fluoro-3,8-dihydroimidazo[4,5-d]pyrido[2,3-b][1]benzazepine;
Cis-[4-(10-fluoro-3,8-dihydroimidazo[4,5-d]pyrido[2,3-b][1]benzazepin-2-yl)cyclohexyl]methanol;
Trans-[4-(10-fluoro-3,8-dihydroimidazo[4,5-d]pyrido[2,3-b][1]benzazepin-2-yl)cyclohexyl]methanol;
Cis-4-(10-fluoro-3,8-dihydroimidazo[4,5-d]pyrido[2,3-b][1]benzazepin-2-yl)cyclohexanol;
Trans-4-(10-fluoro-3,8-dihydroimidazo[4,5-d]pyrido[2,3-b][1]benzazepin-2-yl)cyclohexanol;
Trans-[4-(10-fluoro-3,8-dihydroimidazo[4,5-d]pyrido[2,3-b][1]benzazepin-2-yl)cyclohexyl]acetonitrile;
2-[4-(10-fluoro-3,8-dihydroimidazo[4,5-d]pyrido[2,3-b][1]benzazepin-2-yl)cyclohexyl]acetamide;
tert-butyl 4-(10-fluoro-3,8-dihydroimidazo[4,5-d]pyrido[2,3-b][1]benzazepin-2-yl)piperidine-1-carboxylate;
10-fluoro-2-piperidin-4-yl-3,8-dihydroimidazo[4,5-d]pyrido[2,3-b][1]benzazepine;
3-[4-(10-fluoro-3,8-dihydroimidazo[4,5-d]pyrido[2,3-b][1]benzazepin-2-yl)piperidin-1-yl]-3-oxopropanenitrile;
2-(1-acetylpiperidin-4-yl)-10-fluoro-3,8-dihydroimidazo[4,5-d]pyrido[2,3-b][1]benzazepine;
10-fluoro-2-[1-(methylsulfonyl)piperidin-4-yl]-3,8-dihydroimidazo[4,5-d]pyrido[2,3-b][1]benzazepine;
[4-(10-fluoro-3,8-dihydroimidazo[4,5-d]pyrido[2,3-b][1]benzazepin-2-yl)piperidin-1-yl]acetonitrile;
ethyl [4-(10-fluoro-3,8-dihydroimidazo[4,5-d]pyrido[2,3-b][1]benzazepin-2-yl)piperidin-1-yl]acetate;
2-[4-(10-fluoro-3,8-dihydroimidazo[4,5-d]pyrido[2,3-b][1]benzazepin-2-yl)piperidin-1-yl]ethanol;
3-[4-(10-fluoro-3,8-dihydroimidazo[4,5-d]pyrido[2,3-b][1]benzazepin-2-yl)piperidin-1-yl]propan-1-ol;
4-[4-(10-fluoro-3,8-dihydroimidazo[4,5-d]pyrido[2,3-b][1]benzazepin-2-yl)piperidin-1-yl]butanenitrile;
10-fluoro-2-[3-methyl-5-(trifluoromethyl)-1H-pyrazol-4-yl]-3,8-dihydroimidazo[4,5-d]pyrido[2,3-b][1]benzazepine;
2-[3-(difluoromethyl)-5-methyl-1H-pyrazol-4-yl]-10-fluoro-3,8-dihydroimidazo[4,5-d]pyrido[2,3-b][1]benzazepine;
2-(3,5-dimethyl-1H-pyrazol-4-yl)-10-fluoro-3,8-dihydroimidazo[4,5-d]pyrido[2,3-b][1]benzazepine;
2-(3,5-diethyl-1H-pyrazol-4-yl)-10-fluoro-3,8-dihydroimidazo[4,5-d]pyrido[2,3-b][1]benzazepine;
[4-(10-fluoro-3,8-dihydroimidazo[4,5-d]pyrido[2,3-b][1]benzazepin-2-yl)-5-methyl-3-(trifluoromethyl)-1H-pyrazol-1-yl]acetonitrile;
2-(2-chloro-6-methylphenyl)-10-fluoro-3,8-dihydroimidazo[4,5-d]pyrido[2,3-b][1]benzazepine;
2-(10-fluoro-3,8-dihydroimidazo[4,5-d]pyrido[2,3-b][1]benzazepin-2-yl)-3-methylbenzonitrile;
2-(2,6-dimethylphenyl)-10-fluoro-3,8-dihydroimidazo[4,5-d]pyrido[2,3-b][1]benzazepine;
2-(3,5-dichloropyridin-4-yl)-10-fluoro-3,8-dihydroimidazo[4,5-d]pyrido[2,3-b][1]benzazepine; and
2-(2,4-dimethylpyridin-3-yl)-10-fluoro-3,8-dihydroimidazo[4,5-d]pyrido[2,3-b][1]benzazepine;
or a pharmaceutically acceptable salt thereof.

31. The method of claim 1, wherein the compound is selected from:
4-(3,8-dihydroimidazo[4,5-d]dipyrido[2,3-b:4',3'-f]azepin-2-yl)-4-ethylhexanenitrile;
2-[4-(hydroxymethyl)-cyclohexyl]-imidazo[4,5-d]dipyrido[2,3-b:4',3'-f]azepin-3(8H)-ol;
[4-(3,8-dihydroimidazo[4,5-d]dipyrido[2,3-b:4',3'-f]azepin-2-yl)cyclohexyl]methanol;
[4-(3-hydroxy-3,8-dihydroimidazo[4,5-d]dipyrido[2,3-b:4',3'-f]azepin-2-yl)cyclohexyl]acetonitrile;
[4-(3,8-dihydroimidazo[4,5-d]dipyrido[2,3-b:4',3'-f]azepin-2-yl)cyclohexyl]acetonitrile;
3-(3,8-dihydroimidazo[4,5-d]dipyrido[2,3-b:4',3'-f]azepin-2-yl)-3-methylbutanenitrile;
3-(3,8-dihydroimidazo[4,5-d]dipyrido[2,3-b:4',3'-f]azepin-2-yl)-3-ethylpentanenitrile;
[3-(3,8-dihydroimidazo[4,5-d]dipyrido[2,3-b:4',3'-f]azepin-2-yl)cyclopentyl]acetonitrile;
3-(3,8-dihydroimidazo[4,5-d]dipyrido[2,3-b:4',3'-f]azepin-2-yl)cyclopentanecarbonitrile;
2-(3,5-dichloropyridin-4-yl)-3,8-dihydroimidazo[4,5-d]dipyrido[2,3-b:4',3'-f]azepine;
2-(2,6-dichlorophenyl)-3,8-dihydroimidazo[4,5-d]dipyrido[2,3-b:4',3'-f]azepine;
2-(2,6-dimethylphenyl)-3,8-dihydroimidazo[4,5-d]dipyrido[2,3-b:4',3'-f]azepine;
2-(2-fluoro-6-methoxyphenyl)-3,8-dihydroimidazo[4,5-d]dipyrido[2,3-b:4',3'-f]azepine;
2-(6-chloro-2-fluoro-3-methylphenyl)-3,8-dihydroimidazo[4,5-d]dipyrido[2,3-b:4',3'-f]azepine;
2-[2-fluoro-6-(trifluoromethyl)phenyl]-3,8-dihydroimidazo[4,5-d]dipyrido[2,3-b:4',3'-f]azepine;
2-(2-chloro-6-fluoro-3-methylphenyl)-3,8-dihydroimidazo[4,5-d]dipyrido[2,3-b:4',3'-f]azepine;
2-[3-chloro-2-fluoro-6-(trifluoromethyl)phenyl]-3,8-dihydroimidazo[4,5-d]dipyrido[2,3-b:4',3'-f]azepine;
2-(2-chloro-6-fluorophenyl)-3,8-dihydroimidazo[4,5-d]dipyrido[2,3-b:4',3'-f]azepine;
2-[2-chloro-5-(trifluoromethyl)phenyl]-3,8-dihydroimidazo[4,5-d]dipyrido[2,3-b:4',3'-f]azepine;
2-(2,6-difluorophenyl)-3,8-dihydroimidazo[4,5-d]dipyrido[2,3-b:4',3'-f]azepine;
2-(2,5-dichlorophenyl)-3,8-dihydroimidazo[4,5-d]dipyrido[2,3-b:4',3'-f]azepine;
2-(3,5-dibromopyridin-4-yl)-3,8-dihydroimidazo[4,5-d]dipyrido[2,3-b:4',3'-f]azepine;
2-(2-bromophenyl)-3,8-dihydroimidazo[4,5-d]dipyrido[2,3-b:4',3'-f]azepine;
2-(2-methylphenyl)-3,8-dihydroimidazo[4,5-d]dipyrido[2,3-b:4',3'-f]azepine;
2-(2-chlorophenyl)-3,8-dihydroimidazo[4,5-d]dipyrido[2,3-b:4',3'-f]azepine;

2-(2-ethylphenyl)-3,8-dihydroimidazo[4,5-d]dipyrido[2,3-b:4',3'-f]azepine;
2-(2,5-dimethylphenyl)-3,8-dihydroimidazo[4,5-d]dipyrido[2,3-b:4',3'-f]azepine;
2-[2-chloro-3-(trifluoromethyl)phenyl]-3,8-dihydroimidazo[4,5-d]dipyrido[2,3-b:4',3'-f]azepine;
2-[2,5-bis(trifluoromethyl)phenyl]-3,8-dihydroimidazo[4,5-d]dipyrido[2,3-b:4',3'-f]azepine;
2-(3-chloro-2,6-difluorophenyl)-3,8-dihydroimidazo[4,5-d]dipyrido[2,3-b:4',3'-f]azepine;
2-[2-(trifluoromethyl)phenyl]-3,8-dihydroimidazo[4,5-d]dipyrido[2,3-b:4',3'-f]azepine;
2-(2,3-dichlorophenyl)-3,8-dihydroimidazo[4,5-d]dipyrido[2,3-b:4',3'-f]azepine;
3-[[4-(3,8-dihydroimidazo[4,5-d]dipyrido[2,3-b:4',3'-f]azepin-2-ylphenyl](ethyl)amino]propanenitrile;
2-(2-chloro-3,6-difluorophenyl)-3,8-dihydroimidazo[4,5-d]dipyrido[2,3-b:4',3'-f]azepine;
2-(3-bromopyridin-4-yl)-3,8-dihydroimidazo[4,5-d]dipyrido[2,3-b:4',3'-f]azepine;
2-(5-bromo-2,3-dimethoxyphenyl)-3,8-dihydroimidazo[4,5-d]dipyrido[2,3-b:4',3'-f]azepine;
2-[3-chloro-2-fluoro-5-(trifluoromethyl)phenyl]-3,8-dihydroimidazo[4,5-d]dipyrido[2,3-b:4',3'-f]azepine;
2-(3-chloropyridin-4-yl)-3,8-dihydroimidazo[4,5-d]dipyrido[2,3-b:4',3'-f]azepine;
2-(2,3-dimethylphenyl)-3,8-dihydroimidazo[4,5-d]dipyrido[2,3-b:4',3'-f]azepine;
2-[2-fluoro-3-(trifluoromethyl) phenyl]-3,8-dihydroimidazo[4,5-d]dipyrido[2,3-b:4',3'-f]azepine;
2-(3-fluoro-2-methylphenyl)-3,8-dihydroimidazo[4,5-d]dipyrido[2,3-b:4',3'-f]azepine;
2-(2-fluorophenyl)-3,8-dihydroimidazo[4,5-d]dipyrido[2,3-b:4',3'-f]azepine;
2-(5-bromo-2-methoxyphenyl)-3,8-dihydroimidazo[4,5-d]dipyrido[2,3-b:4',3'-f]azepine;
2-[2-fluoro-5-(trifluoromethyl)phenyl]-3,8-dihydroimidazo[4,5-d]dipyrido[2,3-b:4',3'-f]azepine;
2-(2-fluoro-3-methoxyphenyl)-3,8-dihydroimidazo[4,5-d]dipyrido[2,3-b:4',3'-f]azepine;
2-(2-fluoro-5-methoxyphenyl)-3,8-dihydroimidazo[4,5-d]dipyrido[2,3-b:4',3'-f]azepine;
2-(2,3-difluorophenyl)-3,8-dihydroimidazo[4,5-d]dipyrido[2,3-b:4',3'-f]azepine;
2-quinolin-4-yl-3,8-dihydroimidazo[4,5-d]dipyrido[2,3-b:4',3'-f]azepine;
2-(5-fluoro-2-methoxyphenyl)-3,8-dihydroimidazo[4,5-d]dipyrido[2,3-b:4',3'-f]azepine;
2-(5-bromo-2-fluorophenyl)-3,8-dihydroimidazo[4,5-d]dipyrido[2,3-b:4',3'-f]azepine;
2-(2,5-dimethoxyphenyl)-3,8-dihydroimidazo[4,5-d]dipyrido[2,3-b:4',3'-f]azepine;
2-(2,5-difluorophenyl)-3,8-dihydroimidazo[4,5-d]dipyrido[2,3-b:4',3'-f]azepine;
2-(3,5-dimethyl-1H-pyrrol-2-yl)-3,8-dihydroimidazo[4,5-d]dipyrido[2,3-b:4',3'-f]azepine;
2-(2,6-dimethoxyphenyl)-3,8-dihydroimidazo[4,5-d]dipyrido[2,3-b:4',3'-f]azepine;
2-(4-methyl-1H-imidazol-5yl)-3,8-dihydroimidazo[4,5-d]dipyrido[2,3-b:4',3'-f]azepine;
4-(3,8-dihydroimidazo[4,5-d]dipyrido[2,3-b:4',3'-f]azepin-2-yl)-3,5-dimethoxyphenol;
2-(2-pentafluoroethyl)-3,8-dihydroimidazo[4,5-d]dipyrido[2,3-b:4',3'-f]azepine;
2-(5-bromo-1,3-benzodioxol-4-yl)-3,8-dihydroimidazo[4,5-d]dipyrido[2,3-b:4',3'-f]azepine;

4-(3,8-dihydroimidazo[4,5-d]dipyrido[2,3-b:4',3'-f]azepin-2-yl)-4-phenylpentanenitrile;
2-[2-fluoro-4-(trifluoromethyl)phenyl]-3,8-dihydroimidazo[4,5-d]dipyrido[2,3-b:4',3'-f]azepine;
2-(cyclohexylmethyl)-3,8-dihydroimidazo[4,5-d]dipyrido[2,3-b:4',3'-f]azepine;
3-bromo-2-(3,8-dihydroimidazo[4,5-d]dipyrido[2,3-b:4',3'-f]azepin-2-yl)-6-methoxyphenol;
2-(2-fluoropyridin-4-yl)-3,8-dihydroimidazo[4,5-d]dipyrido[2,3-b:4',3'-f]azepine;
2-biphenyl-2-yl-3,8-dihydroimidazo[4,5-d]dipyrido[2,3-b:4',3'-f]azepine;
methyl-4-(3,8-dihydroimidazo[4,5-d]dipyrido[2,3-b:4',3'-f]azepin-2-yl)benzoate;
2-[2-(ethylthio)phenyl]-3,8-dihydroimidazo[4,5-d]dipyrido[2,3-b:4',3'-f]azepine;
2-(1H-pyrrol-2-yl)-3,8-dihydroimidazo[4,5-d]dipyrido[2,3-b:4',3'-f]azepine;
2-{4-[(trifluoromethyl)thio]phenyl}-3,8-dihydroimidazo[4,5-d]dipyrido[2,3-b:4',3'-f]azepine;
2-(2-naphthyl)-3,8-dihydroimidazo[4,5-d]dipyrido[2,3-b:4',3'-f]azepine;
tert-butyl[1-(3,8-dihydroimidazo[4,5-d]dipyrido[2,3-b:4',3'-f]azepin-2-yl)-2-phenethyl]carbamate;
2-pyrrolidin-2-yl-3,8-dihydroimidazo[4,5-d]dipyrido[2,3-b:4',3'-f]azepine;
2-(2-chloro-6-methoxyquinolin-3-yl)-3,8-dihydroimidazo[4,5-d]dipyrido[2,3-b:4',3'-f]azepine;
2-(1-acetylpyrrolidin-2-yl)-3,8-dihydroimidazo[4,5-d]dipyrido[2,3-b:4',3'-f]azepine;
2-(1,3-thiazol-2-yl)-3,8-dihydroimidazo[4,5-d]dipyrido[2,3-b:4',3'-f]azepine;
1-acetyl-5-(3,8-dihydroimidazo[4,5-d]dipyrido[2,3-b:4',3'-f]azepin-2-yl)pyrrolidin-3-ol;
N-[1-(3,8-dihydroimidazo[4,5-d]dipyrido[2,3-b:4',3'-f]azepin-2-yl)ethyl]acetamide;
tert-butyl 2-(3,8-dihydroimidazo[4,5-d]dipyrido[2,3-b:4',3'-f]azepin-2-yl)-4-hydroxypyrrolidine-1-carboxylate;
N-[4-(3,8-dihydroimidazo[4,5-d]dipyrido[2,3-b:4',3'-f]azepin-2-yl)phenyl]acetamide;
2-[4-(difluoromethoxy)phenyl]-3,8-dihydroimidazo[4,5-d]dipyrido[2,3-b:4',3'-f]azepine;
2-(6-chloropyridin-3-yl)-3,8-dihydroimidazo[4,5-d]dipyrido[2,3-b:4',3'-f]azepine;
6-(3,8-dihydroimidazo[4,5-d]dipyrido[2,3-b:4',3'-f]azepin-2-yl)-2-(methylthio)nicotinonitrile;
2-(3-fluoropyridin-4-yl)-3,8-dihydroimidazo[4,5-d]dipyrido[2,3-b:4',3'-f]azepine;
2-(6-methoxypyridin-3-yl)-3,8-dihydroimidazo[4,5-d]dipyrido[2,3-b:4',3'-f]azepine;
2-(6-bromopyridin-3-yl)-3,8-dihydroimidazo[4,5-d]dipyrido[2,3-b:4',3'-f]azepine;
2-(6-bromopyridin-2-yl)-3,8-dihydroimidazo[4,5-d]dipyrido[2,3-b:4',3'-f]azepine;
2-(1H-imidazol-4-yl)-3,8-dihydroimidazo[4,5-d]dipyrido[2,3-b:4',3'-f]azepine;
2-(3-methoxyphenyl)-3,8-dihydroimidazo[4,5-d]dipyrido[2,3-b:4',3'-f]azepine;
2-(4-methoxyphenyl)-3,8-dihydroimidazo[4,5-d]dipyrido[2,3-b:4',3'-f]azepine;
2-[2-(methylthio)ethyl]-3,8-dihydroimidazo[4,5-d]dipyrido[2,3-b:4',3'-f]azepine;
2-(piperidin-4-yl)-3,8-dihydroimidazo[4,5-d]dipyrido[2,3-b:4',3'-f]azepine;
3-[4-(3,8-dihydroimidazo[4,5-d]dipyrido[2,3-b:4',3'-f]azepin-2-yl)piperidin-1-yl]-3-oxopropanenitrile;

3-[3-(3,8-dihydroimidazo[4,5-d]dipyrido[2,3-b:4',3'-f]azepin-2-yl)piperidin-1-yl]-3-oxopropanenitrile;
3-(4-((3,8-dihydroimidazo[4,5-d]dipyrido[2,3-b:4',3'-f]azepin-2-yl)methyl)piperidin-1-yl)-3-oxopropanenitrile;
3-(3-((3,8-dihydroimidazo[4,5-d]dipyrido[2,3-b:4',3'-f]azepin-2-yl)methyl)piperidin-1-yl)-3-oxopropanenitrile;
2-[1-(trifluoroacetyl)piperidin-4-yl]3,8-dihydroimidazo[4,5-d]dipyrido[2,3-b:4',3'-f]azepine;
2-[1-(trifluoroacetyl)piperidin-3-yl]3,8-dihydroimidazo[4,5-d]dipyrido[2,3-b:4',3'-f]azepine;
2-{[1-(trifluoroacetyl)piperidin-4-yl]methyl}-3,8-dihydroimidazo[4,5-d]dipyrido[2,3-b:4',3'-f]azepine;
2-{[1-(trifluoroacetyl)piperidin-3-yl]methyl}-3,8-dihydroimidazo[4,5-d]dipyrido[2,3-b:4',3'-f]azepine;
2-(1-acetylpiperidin-4-yl)-3,8-dihydroimidazo[4,5-d]dipyrido[2,3-b:4',3'-f]azepine;
3-(3,8-dihydroimidazo[4,5-d]dipyrido[2,3-b:4',3'-f]azepin-2-yl)piperidine-1-carbaldehyde;
2-[(1-acetylpiperidin-4-yl)methyl]-3,8-dihydroimidazo[4,5-d]dipyrido[2,3-b:4',3'-f]azepine;
2-[(1-acetylpiperidin-3-yl)methyl]-3,8-dihydroimidazo[4,5-d]dipyrido[2,3-b:4',3'-f]azepine;
2-(1-methylpiperidin-3-yl)-3,8-dihydroimidazo[4,5-d]dipyrido[2,3-b:4',3'-f]azepine;
4-(3,8-dihydroimidazo[4,5-d]dipyrido[2,3-b:4',3'-f]azepin-2-yl)benzonitrile;
4-(3-hydroxy-3,8-dihydroimidazo[4,5-d]dipyrido[2,3-b:4',3'-f]azepin-2-yl)benzonitrile;
3-(3,8-dihydroimidazo[4,5-d]dipyrido[2,3-b:4',3'-f]azepin-2-yl)benzonitrile;
2-pyridin-3-yl-3,8-dihydroimidazo[4,5-d]dipyrido[2,3-b:4',3'-f]azepine;
2-pyridin-3-ylimidazo[4,5-d]dipyrido[2,3-b:4',3'-f]azepin-3(8H)-ol;
2-pyridin-2-ylimidazo[4,5-d]dipyrido[2,3-b:4',3'-f]azepin-3(8H)-ol;
2-pyridin-4-yl-3,8-dihydroimidazo[4,5-d]dipyrido[2,3-b:4',3'-f]azepine;
2-pyridin-4-ylimidazo[4,5-d]dipyrido[2,3-b:4',3'-f]azepin-3(8H)-ol;
2-piperidin-3-yl-3,8-dihydroimidazo[4,5-d]dipyrido[2,3-b:4',3'-f]azepine;
2-[4-(trifluoromethyl)phenyl]-3,8-dihydroimidazo[4,5-d]dipyrido[2,3-b:4',3'-f]azepine;
2-[6-(trifluoromethyl)pyridine-3-yl]-3,8-dihydroimidazo[4,5-d]dipyrido[2,3-b:4',3'-f]azepine;
2-[3-(trifluoromethyl)phenyl]-3,8-dihydroimidazo[4,5-d]dipyrido[2,3-b:4',3'-f]azepine;
2-(3,5-dimethylisoxazol-4-yl)imidazo[4,5-d]dipyrido[2,3-b:4',3'-f]azepin-3(8H)-ol;
2-[4-(methylthio)phenyl]-3,8-dihydroimidazo[4,5-d]dipyrido[2,3-b:4',3'-f]azepine;
2-[4-(methylthio)phenyl]imidazo[4,5-d]dipyrido[2,3-b:4',3'-f]azepin-3(8H)-ol;
2-[4-(methylsulfonyl)phenyl]-3,8-dihydroimidazo[4,5-d]dipyrido[2,3-b:4',3'-f]azepine;
2-(1H-imidazol-2-yl)-3,8-dihydroimidazo[4,5-d]dipyrido[2,3-b:4',3'-f]azepine;
2-(1-methyl-1H-imidazol-2-yl)-3,8-dihydroimidazo[4,5-d]dipyrido[2,3-b:4',3'-f]azepine;
2-phenyl-3,8-dihydroimidazo[4,5-d]dipyrido[2,3-b:4',3'-f]azepine;
2-phenylimidazo[4,5-d]dipyrido[2,3-b:4',3'-f]azepin-3(8H)-ol;
2-benzyl-3,8-dihydroimidazo[4,5-d]dipyrido[2,3-b:4',3'-f]azepine;
2-benzylimidazo[4,5-d]dipyrido[2,3-b:4',3'-f]azepin-3(8H)-ol;
2-(2-phenethyl)-3,8-dihydroimidazo[4,5-d]dipyrido[2,3-b:4',3'-f]azepine;
2-(2-phenethyl)imidazo[4,5-d]dipyrido[2,3-b:4',3'-f]azepin-3(8H)-ol;
2-piperidin-4-yl-3,8-dihydroimidazo[4,5-d]dipyrido[2,3-b:4',3'-f]azepine;
2-piperidin-4-yl imidazo[4,5-d]dipyrido[2,3-b:4',3'-f]azepin-3(8H)-ol;
2-(piperidin-4-ylmethyl)-3,8-dihydroimidazo[4,5-d]dipyrido[2,3-b:4',3'-f]azepine;
2-(piperidin-4-ylmethyl)imidazo[4,5-d]dipyrido[2,3-b:4',3'-f]azepin-3(8H)-ol;
2-(piperidin-3-ylmethyl)-3,8-dihydroimidazo[4,5-d]dipyrido[2,3-b:4',3'-f]azepine;
2-(tetrahydro-2H-pyran-4-ylmethyl)-3,8-dihydroimidazo[4,5-d]dipyrido[2,3-b:4',3'-f]azepine;
2-(tetrahydro-2H-pyran-4-ylmethyl)imidazo[4,5-d]dipyrido[2,3-b:4',3'-f]azepin-3(8H)-ol;
2-(tetrahydro-2H-thiopyran-4-ylmethyl)-3,8-dihydroimidazo[4,5-d]dipyrido[2,3-b:4',3'-f]azepine;
2-(tetrahydro-2H-thiopyran-4-ylmethyl)imidazo[4,5-d]dipyrido[2,3-b:4',3'-f]azepin-3(8H)-ol;
2-[5-methyl-3-(trifluoromethyl)-1H-pyrazol-4-yl]-3,8-dihydroimidazo[4,5-d]dipyrido[2,3-b:4',3'-f]azepine;
2-[3-(difluoromethyl)-5-methyl-1H-pyrazol-4-yl]-3,8-dihydroimidazo[4,5-d]dipyrido[2,3-b:4',3'-f]azepine;
2-[1-(4-methoxybenzyl)-5-methyl-3-(trifluoromethyl)-1H-pyrazol-4-yl]-3,8-dihydroimidazo[4,5-d]dipyrido[2,3-b:4',3'-f]azepine;
2-[1,5-dimethyl-3-(trifluoromethyl)-1H-pyrazol-4-yl]-3,8-dihydroimidazo[4,5-d]dipyrido[2,3-b:4',3'-f]azepine;
2-[1-ethyl-5-methyl-3-(trifluoromethyl)-1H-pyrazol-4-yl]-3,8-dihydroimidazo[4,5-d]dipyrido[2,3-b:4',3'-f]azepine;
2-[1-(cyclopropylmethyl)-5-methyl-3-(trifluoromethyl)-1H-pyrazol-4-yl]-3,8-dihydroimidazo[4,5-d]dipyrido[2,3-b:4',3'-f]azepine;
2-[3-methyl-5-(pentafluoroethyl)-1H-pyrazol-4-yl]-3,8-dihydroimidazo[4,5-d]dipyrido[2,3-b:4',3'-f]azepine;
4-(3,8-dihydroimidazo[4,5-d]dipyrido[2,3-b:4',3'-f]azepin-2-yl)-N,N,5-trimethyl-3-(trifluoromethyl)-1H-pyrazole-1-sulfonamide;
2-[3-[chloro(difluoro)methyl]-5-methyl-1-(tetrahydro-2H-pyran-2-yl)-1H-pyrazol-4-yl]-3,8-dihydroimidazo[4,5-d]dipyrido[2,3-b:4',3'-f]azepine;
2-[3-(difluoromethyl)-5-methyl-1-(tetrahydro-2H-pyran-2-yl)-1H-pyrazol-4-yl]-3,8-dihydroimidazo[4,5-d]dipyrido[2,3-b:4',3'-f]azepine;
2-(3,5-dimethyl-1H-pyrazol-4-yl)-3,8-dihydroimidazo[4,5-d]dipyrido[2,3-b:4',3'-f]azepine;
2-(3-isobutyl-5-methyl-1H-pyrazol-4-yl)-3,8-dihydroimidazo[4,5-d]dipyrido[2,3-b:4',3'-f]azepine;
2-(3-ethyl-5-methyl-1H-pyrazol-4-yl)-3,8-dihydroimidazo[4,5-d]dipyrido[2,3-b:4',3'-f]azepine;
2-(3-butyl-5-methyl-1H-pyrazol-4-yl)-3,8-dihydroimidazo[4,5-d]dipyrido[2,3-b:4',3'-f]azepine;
2-(3,5-diethyl-1H-pyrazol-4-yl)-3,8-dihydroimidazo[4,5-d]dipyrido[2,3-b:4',3'-f]azepine;
2-(5-cyclopropyl-3-methyl-1H-pyrazol-4-yl)-3,8-dihydroimidazo[4,5-d]dipyrido[2,3-b:4',3'-f]azepine;
2-(2-chloro-6-methylphenyl)-3,8-dihydroimidazo[4,5-d]dipyrido[2,3-b:4',3'-f]azepine;

2-(3,8-dihydroimidazo[4,5-d]dipyrido[2,3-b:4',3'-f]azepin-2-yl)-3-methylbenzonitrile;
2-(2,4-dimethyl-3-thienyl)-3,8-dihydroimidazo[4,5-d]dipyrido[2,3-b:4',3'-f]azepine;
2-[4-methylsulfinyl)phenyl]-3,8-dihydroimidazo[4,5-d]dipyrido[2,3-b:4',3'-f]azepine;
2-[4-(ethylthio)phenyl]-3,8-dihydroimidazo[4,5-d]dipyrido[2,3-b:4',3'-f]azepine;
2-[2-(5-methyl-2-furyl)propyl]-3,8-dihydroimidazo[4,5-d]dipyrido[2,3-b:4',3'-f]azepine;
2-(1-benzothien-5-yl)-3,8-dihydroimidazo[4,5-d]dipyrido[2,3-b:4',3'-f]azepine;
2-(2,4-dimethyl-1,3-thiazol-5-yl)-3,8-dihydroimidazo[4,5-d]dipyrido[2,3-b:4',3'-f]azepine;
2-(5-methyl-3-phenylisoxazol-4-yl)-3,8-dihydroimidazo[4,5-d]dipyrido[2,3-b:4',3'-f]azepine;
2-(4-chloro-1-methyl-1H-pyrazol-3-yl)-3,8-dihydroimidazo[4,5-d]dipyrido[2,3-b:4',3'-f]azepine;
2-(1,3,5-trimethyl-1H-pyrazol-4-yl)-3,8-dihydroimidazo[4,5-d]dipyrido[2,3-b:4',3'-f]azepine;
2-(5-chloro-1,3-dimethyl-1H-pyrazol-4-yl)-3,8-dihydroimidazo[4,5-d]dipyrido[2,3-b:4',3'-f]azepine;
2-(3,5-dimethylisoxazol-4-yl)-3,8-dihydroimidazo[4,5-d]dipyrido[2,3-b:4',3'-f]azepine;
2-[1-(2-methoxyethyl)-2,5-dimethyl-1H-pyrrol-3-yl]-3,8-dihydroimidazo[4,5-d]dipyrido[2,3-b:4',3'-f]azepine;
2-(1-cyclopropyl-2,5-dimethyl-1H-pyrrol-3-yl)-3,8-dihydroimidazo[4,5-d]dipyrido[2,3-b:4',3'-f]azepine;
2-[2,5-dimethoxy-4-(methylthio)phenyl]-3,8-dihydroimidazo[4,5-d]dipyrido[2,3-b:4',3'-f]azepine;
2-(trifluoromethyl)-3,8-dihydroimidazo[4,5-d]dipyrido[2,3-b:4',3'-f]azepine;
2-(2,4-dimethoxy-3-methylphenyl)-3,8-dihydroimidazo[4,5-d]dipyrido[2,3-b:4',3'-f]azepine;
2-[2-(methylthio)phenyl]-3,8-dihydroimidazo[4,5-d]dipyrido[2,3-b:4',3'-f]azepine;
2-(2-ethoxyphenyl)-3,8-dihydroimidazo[4,5-d]dipyrido[2,3-b:4',3'-f]azepine;
2-(2,4-dimethoxyphenyl)-3,8-dihydroimidazo[4,5-d]dipyrido[2,3-b:4',3'-f]azepine;
2-(2,3,4,5,6-pentamethylphenyl)-3,8-dihydroimidazo[4,5-d]dipyrido[2,3-b:4',3'-f]azepine;
2-(2-chloro-4-methoxyphenyl)-3,8-dihydroimidazo[4,5-d]dipyrido[2,3-b:4',3'-f]azepine;
2-(2-methyl-4-methoxyphenyl)-3,8-dihydroimidazo[4,5-d]dipyrido[2,3-b:4',3'-f]azepine;
2-(3,8-dihydroimidazo[4,5-d]dipyrido[2,3-b:4',3'-f]azepin-2-yl)phenol;
2-(2,5-dimethyl-4-methoxyphenyl)-3,8-dihydroimidazo[4,5-d]dipyrido[2,3-b:4',3'-f]azepine;
2-(2-chloro-3,4-dimethoxyphenyl)-3,8-dihydroimidazo[4,5-d]dipyrido[2,3-b:4',3'-f]azepine;
2-(2,3-dimethyl-4-methoxyphenyl)-3,8-dihydroimidazo[4,5-d]dipyrido[2,3-b:4',3'-f]azepine;
2-(2,6-dichloro-3,4-dimethoxyphenyl)-3,8-dihydroimidazo[4,5-d]dipyrido[2,3-b:4',3'-f]azepine;
2,4-dichloro-3-(3,8-dihydroimidazo[4,5-d]dipyrido[2,3-b:4',3'-f]azepin-2-yl)-6-methoxyphenol;
2-(2,4,5-trimethylphenyl)-3,8-dihydroimidazo[4,5-d]dipyrido[2,3-b:4',3'-f]azepine;
2-(2,4-dichlorophenyl)-3,8-dihydroimidazo[4,5-d]dipyrido[2,3-b:4',3'-f]azepine;
2-(2-chloro-4-fluorophenyl)-3,8-dihydroimidazo[4,5-d]dipyrido[2,3-b:4',3'-f]azepine;
2-(2,4-dimethylphenyl)-3,8-dihydroimidazo[4,5-d]dipyrido[2,3-b:4',3'-f]azepine;
2-[2-(trifluoromethoxy)phenyl]-3,8-dihydroimidazo[4,5-d]dipyrido[2,3-b:4',3'-f]azepine;
2-[2-(difluoromethoxy)phenyl]-3,8-dihydroimidazo[4,5-d]dipyrido[2,3-b:4',3'-f]azepine;
2-(2-methoxypyridin-3-yl)-3,8-dihydroimidazo[4,5-d]dipyrido[2,3-b:4',3'-f]azepine;
2-[4-fluoro-2-(trifluoromethyl)phenyl]-3,8-dihydroimidazo[4,5-d]dipyrido[2,3-b:4',3'-f]azepine;
2-(2-methoxyphenyl)-3,8-dihydroimidazo[4,5-d]dipyrido[2,3-b:4',3'-f]azepine;
2-(2,4,6-trimethylphenyl)-3,8-dihydroimidazo[4,5-d]dipyrido[2,3-b:4',3'-f]azepine;
2-chloro-3-(3,8-dihydroimidazo[4,5-d]dipyrido[2,3-b:4',3'-f]azepin-2-yl)-6-methoxyphenol;
2-(3-methylpyridin-2-yl)-3,8-dihydroimidazo[4,5-d]dipyrido[2,3-b:4',3'-f]azepine;
4-(3,8-dihydroimidazo[4,5-d]dipyrido[2,3-b:4',3'-f]azepin-2-yl)-3-ethoxy-N,N-diethylaniline;
2-(2,5-dimethoxy-4-bromophenyl)-3,8-dihydroimidazo[4,5-d]dipyrido[2,3-b:4',3'-f]azepine;
2-(2-isobutoxyphenyl)-3,8-dihydroimidazo[4,5-d]dipyrido[2,3-b:4',3'-f]azepine;
3-(3,8-dihydroimidazo[4,5-d]dipyrido[2,3-b:4',3'-f]azepin-2-yl)pyridine-2-amine;
2-(1H-indol-4-yl)-3,8-dihydroimidazo[4,5-d]dipyrido[2,3-b:4',3'-f]azepine;
2-{2-[(trifluormethyl)thio]phenyl}-3,8-dihydroimidazo[4,5-d]dipyrido[2,3-b:4',3'-f]azepine;
4-bromo-3-(3,8-dihydroimidazo[4,5-d]dipyrido[2,3-b:4',3'-f]azepin-2-yl)phenol;
2-[2-chloro-4-(methylsulfonyl)phenyl]-3,8-dihydroimidazo[4,5-d]dipyrido[2,3-b:4',3'-f]azepine;
2-(2,2-difluoro-1,3-benzodioxol-4-yl)-3,8-dihydroimidazo[4,5-d]dipyrido[2,3-b:4',3'-f]azepine;
4-(3,8-dihydroimidazo[4,5-d]dipyrido[2,3-b:4',3'-f]azepin-2-yl)-3,5-dimethylphenol;
2-(2-chloro-4,6-dimethoxyphenyl)-3,8-dihydroimidazo[4,5-d]dipyrido[2,3-b:4',3'-f]azepine;
2-(3-chlorophenyl)-3,8-dihydroimidazo[4,5-d]dipyrido[2,3-b:4',3'-f]azepine;
2-[3-fluoro-5-(trifluoromethyl)phenyl]-3,8-dihydroimidazo[4,5-d]dipyrido[2,3-b:4',3'-f]azepine;
2-(3,5-dichlorophenyl)-3,8-dihydroimidazo[4,5-d]dipyrido[2,3-b:4',3'-f]azepine;
2-(3-chloro-4-methoxyphenyl)-3,8-dihydroimidazo[4,5-d]dipyrido[2,3-b:4',3'-f]azepine;
2-(6-chloro-1,3-benzodioxol-5-yl)-3,8-dihydroimidazo[4,5-d]dipyrido[2,3-b:4',3'-f]azepine;
2-(4-chloro-2,6-difluorophenyl)-3,8-dihydroimidazo[4,5-d]dipyrido[2,3-b:4',3'-f]azepine;
2-(6-chloro-2,3-difluorophenyl)-3,8-dihydroimidazo[4,5-d]dipyrido[2,3-b:4',3'-f]azepine;
2-(2,6-dichloro-3-fluorophenyl)-3,8-dihydroimidazo[4,5-d]dipyrido[2,3-b:4',3'-f]azepine;
2-(2-chloro-6-fluoro-3-methoxyphenyl)-3,8-dihydroimidazo[4,5-d]dipyrido[2,3-b:4',3'-f]azepine;
2-(2,4,6-trifluorophenyl)-3,8-dihydroimidazo[4,5-d]dipyrido[2,3-b:4',3'-f]azepine;
2-[2-methoxy-4-(trifluoromethoxy)phenyl]-3,8-dihydroimidazo[4,5-d]dipyrido[2,3-b:4',3'-f]azepine;
2-(3-chloro-4-fluorophenyl)-3,8-dihydroimidazo[4,5-d]dipyrido[2,3-b:4',3'-f]azepine;
2-(4-fluoro-2-methylphenyl)-3,8-dihydroimidazo[4,5-d]dipyrido[2,3-b:4',3'-f]azepine;
2-(2,4-dichloro-6-methoxyphenyl)-3,8-dihydroimidazo[4,5-d]dipyrido[2,3-b:4',3'-f]azepine;

2-(2,6-dichloro-3-methoxyphenyl)-3,8-dihydroimidazo [4,5-d]dipyrido[2,3-b:4',3'-f]azepine;
2-(2,6-dichloro-4-methylthiophenyl)-3,8-dihydroimidazo [4,5-d]dipyrido[2,3-b:4',3'-f]azepine;
2-[2,6-dichloro-4-(methylsulfinyl)phenyl]-3,8-dihydroimidazo[4,5-d]dipyrido[2,3-b:4',3'-f]azepine;
2-[2,6-dichloro-4-(methylsulfonyl)phenyl]-3,8-dihydroimidazo[4,5-d]dipyrido[2,3-b:4',3'-f]azepine;
2-(6-chloro-2-fluoro-3-methoxyphenyl)-3,8-dihydroimidazo[4,5-d]dipyrido[2,3-b:4',3'-f]azepine;
2-(2-chloro-6-fluoro-4-methoxyphenyl)-3,8-dihydroimidazo[4,5-d]dipyrido[2,3-b:4',3'-f]azepine;
[3,5-dichloro-4-(3,8-dihydroimidazo[4,5-d]dipyrido[2,3-b:4',3'-f]azepin-2-yl)phenyl]methanol;
[3,5-difluoro-4-(3,8-dihydroimidazo[4,5-d]dipyrido[2,3-b:4',3'-f]azepin-2-yl)phenyl]methanol;
3,5-dichloro-2-(3,8-dihydroimidazo[4,5-d]dipyrido[2,3-b:4',3'-f]azepin-2-yl)phenol;
5-chloro-4-(3,8-dihydroimidazo[4,5-d]dipyrido[2,3-b:4',3'-f]azepin-2-yl)nicotinonitrile;
4-(3,8-dihydroimidazo[4,5-d]dipyrido[2,3-b:4',3'-f]azepin-2-yl)pyridine-3,5-dicarbonitrile;
2-(3,8-dihydroimidazo[4,5-d]dipyrido[2,3-b:4',3'-f]azepin-2-yl)-3-fluoro-6-methylbenzonitrile;
4-(3,8-dihydroimidazo[4,5-d]dipyrido[2,3-b:4',3'-f]azepin-2-yl)nicotinonitrile;
2-(3,8-dihydroimidazo[4,5-d]dipyrido[2,3-b:4',3'-f]azepin-2-yl)-3,6-difluorobenzonitrile;
3-(3,8-dihydroimidazo[4,5-d]dipyrido[2,3-b:4',3'-f]azepin-2-yl)-2-fluoro-4-(trifluoromethyl)benzonitrile;
3-(3,8-dihydroimidazo[4,5-d]dipyrido[2,3-b:4',3'-f]azepin-2-yl)-4-methoxybenzonitrile;
6-(3,8-dihydroimidazo[4,5-d]dipyrido[2,3-b:4',3'-f]azepin-2-yl)-2,3-dimethoxybenzonitrile;
2-(3,8-dihydroimidazo[4,5-d]dipyrido[2,3-b:4',3'-f]azepin-2-yl)-4,5-dimethoxyisophthalonitrile;
2-(3,8-dihydroimidazo[4,5-d]dipyrido[2,3-b:4',3'-f]azepin-2-yl)-4-hydroxy-5-methoxyisophthalonitrile;
4-(3,8-dihydroimidazo[4,5-d]dipyrido[2,3-b:4',3'-f]azepin-2-yl)-2,5-dimethoxybenzonitrile;
2-(3,8-dihydroimidazo[4,5-d]dipyrido[2,3-b:4',3'-f]azepin-2-yl)-5-(methylsulfonyl)benzonitrile;
2-(3,8-dihydroimidazo[4,5-d]dipyrido[2,3-b:4',3'-f]azepin-2-yl)-3,5-dimethoxybenzonitrile;
2-(3,8-dihydroimidazo[4,5-d]dipyrido[2,3-b:4',3'-f]azepin-2-yl)-3,5-difluorobenzonitrile;
2-(3,8-dihydroimidazo[4,5-d]dipyrido[2,3-b:4',3'-f]azepin-2-yl)-3,4-difluorobenzonitrile;
2-(3,8-dihydroimidazo[4,5-d]dipyrido[2,3-b:4',3'-f]azepin-2-yl)-3-fluoro-6-methoxybenzonitrile;
5-(3,8-dihydroimidazo[4,5-d]dipyrido[2,3-b:4',3'-f]azepin-2-yl)-2-fluorobenzonitrile;
2-(3,8-dihydroimidazo[4,5-d]dipyrido[2,3-b:4',3'-f]azepin-2-yl)-3-fluoro-4-methoxybenzonitrile;
2-(3,8-dihydroimidazo[4,5-d]dipyrido[2,3-b:4',3'-f]azepin-2-yl)-3-fluoro-5-methoxybenzonitrile;
2-(3,8-dihydroimidazo[4,5-d]dipyrido[2,3-b:4',3'-f]azepin-2-yl)-5-(methylthio)isophthalonitrile;
2-(3,8-dihydroimidazo[4,5-d]dipyrido[2,3-b:4',3'-f]azepin-2-yl)-5-(hydroxymethyl)isophthalonitrile;
2-(3,8-dihydroimidazo[4,5-d]dipyrido[2,3-b:4',3'-f]azepin-2-yl)-5-(hydroxymethyl)benzonitrile;
[3,5-dichloro-4-(3,8-dihydroimidazo[4,5-d]dipyrido[2,3-b:4',3'-f]azepin-2-yl)phenyl]acetonitrile;
5-(cyanomethyl)-2-(3,8-dihydroimidazo[4,5-d]dipyrido[2,3-b:4',3'-f]azepin-2-yl)isophthalonitrile;
5-(cyanomethyl)-2-(3,8-dihydroimidazo[4,5-d]dipyrido[2,3-b:4',3'-f]azepin-2-yl)benzonitrile;
2-(3,8-dihydroimidazo[4,5-d]dipyrido[2,3-b:4',3'-f]azepin-2-yl)-5-(methylsulfinyl)benzonitrile;
2-(3,8-dihydroimidazo[4,5-d]dipyrido[2,3-b:4',3'-f]azepin-2-yl)5-(methylsulfonyl)isophthalonitrile;
2-(3,8-dihydroimidazo[4,5-d]dipyrido[2,3-b:4',3'-f]azepin-2-yl)-5-hydroxybenzonitrile;
1-[3,5-dichloro-4-(3,8-dihydroimidazo[4,5-d]dipyrido[2,3-b:4',3'-f]azepin-2-yl)phenyl]-N,N-dimethylmethanamine;
2-[2,6-dichloro-4-(morpholin-4-ylmethyl)phenyl]-3,8-dihydroimidazo[4,5-d]dipyrido[2,3-b:4',3'-f]azepine;
2-[2,6-dichloro-4-(thiomorpholin-4-ylmethyl)phenyl]-3,8-dihydroimidazo[4,5-d]dipyrido[2,3-b:4',3'-f]azepine;
2-[2,6-dichloro-4-(methoxymethyl)phenyl]-3,8-dihydroimidazo[4,5-d]dipyrido[2,3-b:4',3'-f]azepine;
2-[2,6-dichloro-4-(ethylthio)phenyl]-3,8-dihydroimidazo [4,5-d]dipyrido[2,3-b:4',3'-f]azepine;
2-[2,6-dichloro-4-(isopropylthio)phenyl]-3,8-dihydroimidazo[4,5-d]dipyrido[2,3-b:4',3'-f]azepine;
2-[2,6-dichloro-4-(ethylsulfinyl)phenyl]-3,8-dihydroimidazo[4,5-d]dipyrido[2,3-b:4',3'-f]azepine;
2-[2,6-dichloro-4-(ethylsulfonyl)phenyl]-3,8-dihydroimidazo[4,5-d]dipyrido[2,3-b:4',3'-f]azepine;
2-[2,6-dichloro-4-(isopropylsulfinyl)phenyl]-3,8-dihydroimidazo[4,5-d]dipyrido[2,3-b:4',3'-f]azepine;
2-[2,6-dichloro-4-(isopropylsulfonyl)phenyl]-3,8-dihydroimidazo[4,5-d]dipyrido[2,3-b:4',3'-f]azepine;
2-(3,8-dihydroimidazo[4,5-d]dipyrido[2,3-b:4',3'-f]azepin-2-yl)-5-(isopropylsulfonyl)benzonitrile;
2-(3,8-dihydroimidazo[4,5-d]dipyrido[2,3-b:4',3'-f]azepin-2-yl)-5-(ethylthio)isophthalonitrile;
3-chloro-2-(3,8-dihydroimidazo[4,5-d]dipyrido[2,3-b:4',3'-f]azepin-2-yl)-5-(ethylthio)benzonitrile;
2-(3,8-dihydroimidazo[4,5-d]dipyrido[2,3-b:4',3'-f]azepin-2-yl)-5-(isopropylthio)isophthalonitrile;
3-chloro-2-(3,8-dihydroimidazo[4,5-d]dipyrido[2,3-b:4',3'-f]azepin-2-yl)-5-(isopropylthio)benzonitrile;
2-(3,8-dihydroimidazo[4,5-d]dipyrido[2,3-b:4',3'-f]azepin-2-yl)-5-(isopropylsulfinyl)isophthalonitrile;
3-chloro-2-(3,8-dihydroimidazo[4,5-d]dipyrido[2,3-b:4',3'-f]azepin-2-yl)-5-(isopropylsulfinyl)benzonitrile;
2-[3,5-dichloro-4-(3,8-dihydroimidazo[4,5-d]dipyrido[2,3-b:4',3'-f]azepin-2-yl)phenoxy]acetonitrile;
2-[3,5-dichloro-4-(3,8-dihydroimidazo[4,5-d]dipyrido[2,3-b:4',3'-f]azepin-2-yl)phenoxy]propanenitrile;
5-(1-cyanoethoxy)-2-(3,8-dihydroimidazo[4,5-d]dipyrido[2,3-b:4',3'-f]azepin-2-yl)isophthalonitrile;
5-(1-cyanoethoxy)-2-(3,8-dihydroimidazo[4,5-d]dipyrido[2,3-b:4',3'-f]azepin-2-yl)benzonitrile;
5-(cyanomethoxy)-2-(3,8-dihydroimidazo[4,5-d]dipyrido[2,3-b:4',3'-f]azepin-2-yl)isophthalonitrile;
2-[3,5-dichloro-4-(3,8-dihydroimidazo[4,5-d]dipyrido[2,3-b:4',3'-f]azepin-2-yl)phenoxy]propanamide;
2-[3,5-dicyano-4-(3,8-dihydroimidazo[4,5-d]dipyrido[2,3-b:4',3'-f]azepin-2-yl)phenoxy]propanamide;
5-(2-amino-1-methyl-2-oxoethoxy)-3-cyano-2-(3,8-dihydroimidazo[4,5-d]dipyrido[2,3-b:4',3'-f]azepin-2-yl)benzamide;
5-(2-amino-1-methyl-2-oxoehtoxy)-2-(3,8-dihydroimidazo[4,5-d]dipyrido[2,3-b:4',3'-f]azepin-2-yl)isophthalamide;
2-[3,5-dichloro-4-(3,8-dihydroimidazo[4,5-d]dipyrido[2,3-b:4',3'-f]azepin-2-yl)phenoxy]acetamide;
2-[3,5-dicyano-4-(3,8-dihydroimidazo[4,5-d]dipyrido[2,3-b:4',3'-f]azepin-2-yl)phenoxy]acetamide;

2-cyano-2-[3,5-dichloro-4-(3,8-dihydroimidazo[4,5-d]
dipyrido[2,3-b:4',3'-f]azepin-2-yl)phenoxy]-N,N-dimethylacetamide;
2-(3,8-dihydroimidazo[4,5-d]dipyrido[2,3-b:4',3'-f]
azepin-2-yl)isophthalonitrile;
2-(3,8-dihydroimidazo[4,5-d]dipyrido[2,3-b:4',3'-f]
azepin-2-yl)benzonitrile;
2-(3,8-dihydroimidazo[4,5-d]dipyrido[2,3-b:4',3'-f]
azepin-2-yl)-4-hydroxybenzonitrile;
4-(3,8-dihydroimidazo[4,5-d]dipyrido[2,3-b:4',3'-f]
azepin-2-yl)-1,3-benzodioxole-5-carbonitrile;
3-chloro-2-(3,8-dihydroimidazo[4,5-d]dipyrido[2,3-b:4',
3'-f]azepin-2-yl)benzonitrile;
3-fluoro-4-methyl-2-(3,8-dihydroimidazo[4,5-d]dipyrido
[2,3-b:4',3'-f]azepin-2-yl)benzonitrile;
3-fluoro-2-(3,8-dihydroimidazo[4,5-d]dipyrido[2,3-b:4',
3'-f]azepin-2-yl)benzonitrile;
3-methoxy-2-(3,8-dihydroimidazo[4,5-d]dipyrido[2,3-b:
4',3'-f]azepin-2-yl)benzonitrile;
5-fluoro-2-(3,8-dihydroimidazo[4,5-d]dipyrido[2,3-b:4',
3'-f]azepin-2-yl)benzonitrile;
3-chloro-6-methoxy-2-(3,8-dihydroimidazo[4,5-d]dipyrido[2,3-b:4',3'-f]azepin-2-yl)benzonitrile;
2-(3,8-dihydroimidazo[4,5-d]dipyrido[2,3-b:4',3'-f]
azepin-2-yl)-4-methoxyisophthalonitrile;
tert-butyl [4-(3,8-dihydroimidazo[4,5-d]dipyrido[2,3-b:
4',3'-f]azepin-2-yl)pyridine-3-yl]carbamate;
tert-butyl [4-(3-hydroxy-3,8-dihydroimidazo[4,5-d]dipyrido[2,3-b:4',3'-f]azepin-2-yl)pyridin-3-yl]carbamate;
2-(3,5-dimethylpyridin-4-yl)-3,8-dihydroimidazo[4,5-d]
dipyrido[2,3-b:4',3'-f]azepine;
3,5-dichloro-4-(3,8-dihydroimidazo[4,5-d]dipyrido[2,3-b:4',3'-f]azepin-2-yl)phenol;
2-(2,6-dichloro-4-methoxyphenyl)-3,8-dihydroimidazo
[4,5-d]dipyrido[2,3-b:4',3'-f]azepine;
2-(2,6-dichloro-4-ethoxyphenyl)-3,8-dihydroimidazo[4,
5-d]dipyrido[2,3-b:4',3'-f]azepine;
2-(2,6-dichloro-4-isopropoxyphenyl)-3,8-dihydroimidazo[4,5-d]dipyrido[2,3-b:4',3'-f]azepine;
2-[2,6-dichloro-4-(trifluoromethoxy)phenyl]-3,8-dihydroimidazo[4,5-d]dipyrido[2,3-b:4',3'-f]azepine;
2-(3-methylpyridin-4-yl)-3,8-dihydroimidazo[4,5-d]
dipyrido[2,3-b:4',3'-f]azepine;
2-(2-methylpyridin-3-yl)-3,8-dihydroimidazo[4,5-d]
dipyrido[2,3-b:4',3'-f]azepine;
2-(2,4-dimethylpyridin-3-yl)-3,8-dihydroimidazo[4,5-d]
dipyrido[2,3-b:4',3'-f]azepine;
2-(5-chloro-2-ethoxyphenyl)-3,8-dihydroimidazo[4,5-d]
dipyrido[2,3-b:4',3'-f]azepine;
2-(5-chloro-2-methoxyphenyl)-3,8-dihydroimidazo[4,5-d]dipyrido[2,3-b:4',3'-f]azepine;
2-(5-bromo-2-ethoxyphenyl)-3,8-dihydroimidazo[4,5-d]
dipyrido[2,3-b:4',3'-f]azepine;
2-(2,3-difluoro-6-methoxyphenyl)-3,8-dihydroimidazo[4,
5-d]dipyrido[2,3-b:4',3'-f]azepine;
2-[2,6-dichloro-4-(trifluoromethyl)phenyl]-3,8-dihydroimidazo[4,5-d]dipyrido[2,3-b:4',3'-f]azepine;
3,5-dichloro-4-(3,8-dihydroimidazo[4,5-d]dipyrido[2,3-b:4',3'-f]azepin-2-yl)-N,N-dimethylaniline;
2-(2,6-dichloro-4-fluorophenyl)-3,8-dihydroimidazo[4,5-d]dipyrido[2,3-b:4',3'-f]azepine;
3-chloro-2-(3,8-dihydroimidazo[4,5-d]dipyrido[2,3-b:4',
3'-f]azepin-2-yl)-5-methoxybenzonitrile;
2-(3,8-dihydroimidazo[4,5-d]dipyrido[2,3-b:4',3'-f]
azepin-2-yl)-5-methoxyisophthalonitrile;
3-chloro-2-(3,8-dihydroimidazo[4,5-d]dipyrido[2,3-b:4',
3'-f]azepin-2-yl)-5-ethoxybenzonitrile;
2-(3,8-dihydroimidazo[4,5-d]dipyrido[2,3-b:4',3'-f]
azepin-2-yl)-5-ethoxyisophthalonitrile;
3-chloro-2-(3,8-dihydroimidazo[4,5-d]dipyrido[2,3-b:4',
3'-f]azepin-2-yl)-5-isopropoxybenzonitrile;
2-(3,8-dihydroimidazo[4,5-d]dipyrido[2,3-b:4',3'-f]
azepin-2-yl)-5-isopropoxyisophthalonitrile;
2-(3,8-dihydroimidazo[4,5-d]dipyrido[2,3-b:4'3'4]
azepin-2-yl)-5-(trifluoromethoxy)isophthalonitrile;
3-chloro-2-(3,8-dihydroimidazo[4,5-d]dipyrido[2,3-b:4',
3'-f]azepin-2-yl)-5-(trifluoromethyl)benzonitrile;
3-chloro-2-(3,8-dihydroimidazo[4,5-d]dipyrido[2,3-b:4',
3'-f]azepin-2-yl)-5-(dimethylamino)benzonitrile; and
3-chloro-2-(3,8-dihydroimidazo[4,5-d]dipyrido[2,3-b:4',
3'-f]azepin-2-yl)-5-fluorobenzonitrile;
or a pharmaceutically acceptable salt thereof.

32. The method of claim 1, wherein the compound is selected from:
2-(3,5-dichloropyridin-4-yl)-3,8-dihydroimidazo[4,5-d]
dipyrido[2,3-b:3',4'-f]azepine;
2-(2,6-dichlorophenyl)-3,8-dihydroimidazo[4,5-d]dipyrido[2,3-b:3',4'-f]azepine;
2-(2,6-difluorophenyl)-3,8-dihydroimidazo[4,5-d]dipyrido[2,3-b:3',4'-f]azepine;
2-(2-chloro-6-fluorophenyl)-3,8-dihydroimidazo[4,5-d]
dipyrido[2,3-b:3',4'-f]azepine;
2-(2,6-dimethylphenyl)-3,8-dihydroimidazo[4,5-d]dipyrido[2,3-b:3',4'-f]azepine;
4-(3,8-dihydroimidazo[4,5-d]dipyrido[2,3-b:3',4'-f]
azepin-2-yl)-4-ethylhexanenitrile;
2-[1-(4-methoxybenzyl)-5-methyl-3-(trifluoromethyl)-
1H-pyrazol-4-yl]imidazo[4,5-d]dipyrido[2,3-b:3',4'-f]
azepin-3(8H)-ol;
2-[1-(4-methoxybenzyl)-5-methyl-3-(trifluoromethyl)-
1H-pyrazol-4-yl]-3,8-dihydroimidazo[4,5-d]dipyrido
[2,3-b:3',4'-f]azepine;
2-[5-methyl-3-(trifluoromethyl)-1H-pyrazol-4-yl]imidazo[4,5-d]dipyrido[2,3-b:3',4'-f]azepin-3(8H)-ol;
2-[5-methyl-3-(trifluoromethyl)-1H-pyrazol-4-yl]-3,8-dihydroimidazo[4,5-d]dipyrido[2,3-b:3',4'-f]azepine;
2-(2,3-dimethylphenyl)imidazo[4,5-d]dipyrido[2,3-b:3',
4'-f]azepin-3(8H)-ol;
2-(2,3-dimethylphenyl)-3,8-dihydroimidazo[4,5-d]dipyrido[2,3-b:3',4'-f]azepine;
2-[2-(dimethylamino)-pyridin-3-yl]imidazo[4,5-d]dipyrido[2,3-b:3',4'-f]azepin-3(8H)-ol;
3-(3,8-dihydroimidazo[4,5-d]dipyrido[2,3-b:3',4'-f]
azepin-2-yl)-N,N-dimethylpyridin-2-amine; and
2-(3,8-dihydroimidazo[4,5-d]dipyrido[2,3-b:3',4'-f]
azepin-2-yl)-3-fluorobenzonitrile;
or a pharmaceutically acceptable salt thereof.

33. The method of claim 1, wherein the compound is 2-(2,6-dichlorophenyl)-2,8-dihydropyrazolo[3,4-d]dipyrido[2,3-b:3',4'-f]azepine, or pharmaceutically acceptable salt thereof.

* * * * *